United States Patent
Liang et al.

(10) Patent No.: US 12,172,946 B2
(45) Date of Patent: Dec. 24, 2024

(54) COMPOUND CONTAINING DIPHENYLMETHANE STRUCTURE AND USE THEREOF

(71) Applicant: GUANGZHOU TROJAN PHARMATEC LTD., Guangdong (CN)

(72) Inventors: Weizhou Liang, Guangzhou (CN); Qingquan Zheng, Guangzhou (CN); Qi Tang, Guangzhou (CN)

(73) Assignee: GUANGZHOU TROJAN PHARMATEC LTD., Guangdong (CN)

( * ) Notice: Subject to any disclaimer, the term of this patent is extended or adjusted under 35 U.S.C. 154(b) by 640 days.

(21) Appl. No.: 17/421,316

(22) PCT Filed: Dec. 13, 2019

(86) PCT No.: PCT/CN2019/125136
§ 371 (c)(1),
(2) Date: Jul. 7, 2021

(87) PCT Pub. No.: WO2020/143392
PCT Pub. Date: Jul. 16, 2020

(65) Prior Publication Data
US 2022/0002230 A1   Jan. 6, 2022

(30) Foreign Application Priority Data
Jan. 7, 2019 (CN) .......................... 201910012866.7

(51) Int. Cl.
| C07C 235/60 | (2006.01) |
| C07C 233/18 | (2006.01) |
| C07C 233/22 | (2006.01) |
| C07C 233/47 | (2006.01) |
| C07C 235/34 | (2006.01) |
| C07C 235/50 | (2006.01) |
| C07C 235/52 | (2006.01) |
| C07K 1/06   | (2006.01) |

(52) U.S. Cl.
CPC .......... *C07C 235/60* (2013.01); *C07C 233/18* (2013.01); *C07C 233/22* (2013.01); *C07C 233/47* (2013.01); *C07C 235/34* (2013.01); *C07C 235/50* (2013.01); *C07C 235/52* (2013.01); *C07K 1/061* (2013.01)

(58) Field of Classification Search
None
See application file for complete search history.

(56) References Cited

U.S. PATENT DOCUMENTS

2010/0249374 A1   9/2010   Takahashi

FOREIGN PATENT DOCUMENTS

| CN | 107406480 A | 11/2017 |
| CN | 109678751 A | 4/2019 |
| CN | 110194724 A | 9/2019 |

OTHER PUBLICATIONS

Subra et al. (Tet. Let., 2002, 43, 9221). (Year: 2002).*
International Search Report issue in corresponding International Application No. PCT/CN2019/125136; China National Intellectual Property Administration; mailed Mar. 19, 2020; 6 pgs.
Written Opinion of the International Searching Authority issued in corresponding International Application No. PCT/CN2019/125136; China National Intellectual Property Administration; mailed Mar. 19, 2020; 9 pgs.
First Office Action issued in corresponding Chinese Application No. 201910476362.0; The State Intellectual Property Office of the People's Republic of China, mailed Jul. 1, 2020; 23 pgs.
Second Office Action issued in corresponding Chinese Application No. 201910476362.0; The State Intellectual Property Office of the People's Republic of China, mailed Oct. 20, 2020; 13 pgs.

* cited by examiner

*Primary Examiner* — Sudhakar Katakam
*Assistant Examiner* — Jennifer C Sawyer
(74) *Attorney, Agent, or Firm* — HAUPTMAN HAM, LLP

(57) ABSTRACT

A structure of the compound containing a diphenylmethane structure of the present invention is represented by General Formula (1). The compound containing a diphenylmethane structure of the present invention contains a hydroxyl group, an amino group, a substituted amino group, and an active group, and can be used as an amino acid or peptide C-terminal protection reagent. A peptide synthesis reaction using this protection carrier has a fast reaction speed and a high reagent utilization rate in a suitable solvent system; post-treatment is carried out by means of simple liquid-liquid extraction separation, i.e. effective purification can be carried out, and finally, a product with a high purity can be obtained; and during a synthesis process, the change in solubility is small and an operation process has a strong universality, and therefore, the present method can be developed into a universal production method.

19 Claims, No Drawings

COMPOUND CONTAINING DIPHENYLMETHANE STRUCTURE AND USE THEREOF

RELATED APPLICATIONS

The present application is a U.S. National Phase of International Application Number PCT/CN2019/125136 filed Dec. 13, 2019 and claims priority to Chinese Application Number 201910012866.7 filed Jan. 7, 2019.

TECHNICAL FIELD

The present invention relates to the technical field of compound and polypeptide synthesis, and particularly, to a compound containing a diphenylmethane structure and use thereof.

BACKGROUND ART

Synthetic methods for producing peptides can be mainly classified into three types at present: solid-phase carrier synthesis method, conventional liquid-phase synthesis method and liquid phase carrier synthesis method.

The solid-phase carrier synthesis method can complete the work of separation and purification through a simple solid-liquid separation, and has the advantages of strong universality, short development period and the like. The solid-liquid two-phase reaction has a serious problem of mass transfer due to the poor affinity between a solvent and a solid phase carrier and the spatial structure of the carrier and the like, and the reaction speed is limited. In order to compensate for the low reactivity, the reaction reagent needs to be in large excess under a conventional reaction condition. The intermediate is attached to the solid-phase carrier, so a conventional analysis is difficult to perform, and a purification process cannot be performed, and generally, the final product can be purified only by the reversed-phase liquid preparative chromatography.

The conventional liquid-phase synthesis method is generally a homogeneous reaction and has good reactivity, an intermediate can be purified by means of extraction and washing, crystallization and the like, and the purity of a final product is high. However, the properties of a product and impurity of each reaction have large differences, so that a universal method for separation and purification cannot be found, the development period is long, and the manufacturing steps are complex.

The liquid-phase carrier synthesis method is a new peptide synthesis method developed in the last decade for improving the above two types of methods. Among them, a representative example includes Molecular Hiving™ technique by JITSUBO Co. and Ajiphase technique by Ajinomoto Co.

The Molecular Hiving™ technique by JITSUBO Co. uses a long-chain alkoxybenzyl alcohol such as 3,5-di(docosyloxy)benzyl alcohol, 2,4-di(docosyloxy)benzyl alcohol, 3,4,5-tri(octadecyloxy)benzyl alcohol and the like as a liquid-phase carrier. The carrier is used as a C-terminal protective reagent to perform the synthesis of peptide, the reaction is carried out in a homogeneous phase, the product is precipitated by changing the solvent composition or the temperature change, and the separation and purification are realized by the steps of precipitating-filtrating-washing. This method has the following problems: ① the solubility of the carrier in solvents such as acetate, toluene and the like which has a medium or low polarity is not large, the reaction concentration is low, and it is not favorable for amplification production; ② the procedure of changing the solvent composition can be completed only by operations of quantitative distillation and the like, which is complex; ③ as changing the solvent system, the precipitate is generally an amorphous solid, and the filtrating-washing is very difficult, the impurity removing effect is poor and it consumes a long time. Therefore, it cannot to say that this method is an universal peptide synthesis method with a good reproducibility.

The Ajiphase technique by Ajinomoto Co. has made an improvement of the former, which uses a multi-branched alkyl instead of a straight-chain alkyl, the solubility of the carrier in solvents such as isopropyl acetate is effectively improved, the reaction can be carried out at a higher concentration, and a separation and purification can be realized by using water & organic polar solvent for extraction and washing. This method has the following problems: ① the reaction time is long—the Examples of the Patent Publication No. CN107011132A use isopropyl acetate or methyl cyclopentyl ether as a solvent, the condensation needs to be reacted overnight, the deprotection needs 4-6 hours, while the condensation reaction using chloroform as a solvent in other published literature materials needs more than 3 hours, so the reaction time is long, leading to an increased impurities; ② due to the difference of a two-phase polarity is small during the liquid-liquid separation, the impurities are difficult to remove and the purity of a product is low; ③ during the process of synthesizing a peptide by using this type of carrier, the solubility is reduced rapidly, and generally, the gelation phenomenon occurs when the number of amino acids of a peptide chain is more than 4. Therefore, it is also difficult to say that this method is a universal peptide synthesis method with a good reproducibility.

Therefore, it is of great significance to synthesize a universal protective carrier compound for liquid-phase synthetic, and further obtain a universal peptide synthesis method with a good reproducibility.

DISCLOSURE OF INVENTION

The purpose of the present invention is to overcome the above shortcomings of the prior art and to provide a compound containing a diphenylmethane structure and use thereof. By using the compound as a protective carrier for peptide liquid-phase synthesis, in a homogeneous or heterogeneous solvent system, especially in a heterogeneous solvent system, it can increase the reaction speed and the reagent utilization, simplify the post-treatment operation, improve the purity of product, improve the universality of operation process, and it can be developed into a universal production method.

In order to achieve the above objective, the technical solution adopted by the present invention is: a compound containing a diphenylmethane structure, and the structure of the compound is as shown in General Formula (1):

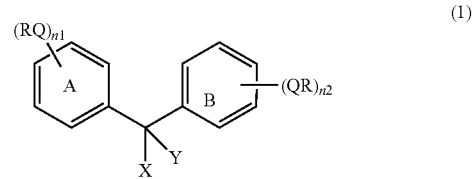

wherein,

X is selected from OH, halogen, sulfonate or $NHR_a$, and $R_a$ is selected from hydrogen, alkyl group or aralkyl group;

Y is selected from hydrogen, phenyl group or substituted phenyl group;

ring A and ring B may contain a substituent selected from halogen atom, $C_1$~$C_5$ alkyl group substituted with halogen atom, $C_1$~$C_5$ alkyl group unsubstituted with halogen atom, $C_1$~$C_5$ alkoxy group substituted with halogen atom, or $C_1$~$C_5$ alkoxy group unsubstituted with halogen atom, in addition to the RQ substituent;

Q is independently selected from O, NH, NHCO, CO, CONH, S, SO or $SO_2$;

$n_1$ and $n_2$ represents an integer of 0~3, respectively, and $n_1$ and $n_2$ are not 0 at the same time;

R is independently selected from the group represented by General Formula (2):

$$R_1 \underset{\underset{R_2}{|}}{\overset{\overset{O}{\|}}{C}} -N-L-* \quad (2)$$

in the General Formula (2), * represents connected with Q;

$R_1$ is selected from $C_1$~$C_{25}$ alkyl group or a group represented by General Formula (3):

$$\underset{m}{(R_3O)} - \underset{C}{\phenyl} - \underset{k}{CH}_2 -* \quad (3)$$

in the General Formula (3), * represents connected with carbonyl;

m represents an integer of 1~3;

$R_3$ is selected from $C_6$~$C_{25}$ alkyl group, and a total carbon number of m $R_3$s is not less than 8;

k represents an integer of 0~3;

ring C may contain a substituent selected from halogen atom, $C_1$~$C_5$ alkyl group substituted with halogen atom, $C_1$~$C_5$ alkyl group unsubstituted with halogen atom, $C_1$~$C_5$ alkoxy group substituted with halogen atom, $C_1$~$C_5$ alkoxy group unsubstituted with halogen atom, in addition to m $R_3O$ substituents;

$R_2$ is selected from hydrogen, $C_1$~$C_{25}$ alkyl group or a group represented by General Formula (4):

$$(R_7O)_{m2} - \underset{D}{\phenyl} - \underset{k}{CH}_2 -* \quad (4)$$

in the General Formula (4), * represents connected with N; $m_2$ represents an integer of 0~3;

$R_7$ is selected from $C_6$~$C_{25}$ alkyl group;

$k_7$ represents an integer of 1~6;

ring D may contain a substituent selected from halogen atom, $C_1$~$C_5$ alkyl group substituted with halogen atom, $C_1$~$C_5$ alkyl group unsubstituted with halogen atom, $C_1$~$C_5$ alkoxy group substituted with halogen atom, $C_1$~$C_5$ alkoxy group unsubstituted with halogen atom, in addition to $m_2$ $R_7O$ substituents;

L is selected from $C_2$~$C_{15}$ organic chain group containing O, N or S heteroatoms, or $C_2$~$C_{15}$ organic chain group not containing O, N or S heteroatoms, and when L is selected from the $C_2$~$C_{15}$ organic chain group not containing O, N or S heteroatoms, $R_2 \neq H$.

As a preferred embodiment of the compound containing a diphenylmethane structure of the present invention, preferably, the above-mentioned X is selected from OH or $NHR_a$, $R_a$ is selected from hydrogen, alkyl or aralkyl; Y is selected from hydrogen, phenyl group or halogenated phenyl group.

As a preferred embodiment of the compound containing a diphenylmethane structure of the present invention, the above-mentioned R is independently selected from a group represented by General Formula (5):

$$R_1 \underset{\underset{R_2}{|}}{\overset{\overset{O}{\|}}{C}} -N - CH_2CH_2 - [O - CH_2CH_2]_{k1} -* \quad (5)$$

wherein,

* represents connected with Q;

k1 represents an integer of 0~3, and when k1=0, $R_2 \neq H$; preferably, k1 represents 1 or 2.

As a preferred embodiment of the compound containing a diphenylmethane structure of the present invention, the above-mentioned R is independently selected from a group represented by General Formula (6):

$$R_1 \underset{\underset{R_2}{|}}{\overset{\overset{O}{\|}}{C}} -N - (CH_2)_{k2} - \underset{\underset{R_4}{|}}{N} - \overset{\overset{O}{\|}}{C} - (CH_2)_{k3}-* \quad (6)$$

wherein,

* represents connected with Q;

$R_4$ is selected from hydrogen, $C_1$~$C_{25}$ alkyl group or a group represented by the General Formula (4) above;

k2 represents an integer of 1~4;

k3 represents an integer of 1~4.

As a preferred embodiment of the compound containing a diphenylmethane structure of the present invention, the above-mentioned R is independently selected from a group represented by General Formula (7):

$$R_1 \overset{\overset{O}{\|}}{C} -\underset{\underset{R_5}{|}}{N} - (CH)_{k4} - \underset{\underset{R_6}{|}}{N} - \overset{\overset{O}{\|}}{C} - CH_2CH_2 [O-CH_2CH_2]_{k5} -* \quad (7)$$

wherein,

* represents connected with Q;

$R_6$ is selected from hydrogen, $C_1$~$C_{25}$ alkyl group or a group represented by the General Formula (4) above;

k4 represents an integer of 0~3;

k5 represents an integer of 0~3;

$R_5$ is selected from hydrogen, a side chain group of natural amino acid, an alkyl group or a group represented by General Formula (8):

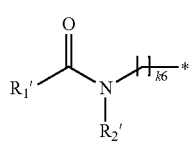

in the General Formula (8), k6 represents an integer of 1~4;

$R_{2'}$ is selected from hydrogen, $C_1$~$C_{25}$ alkyl group or a group represented by the General Formula (4) above;

$R_{1'}$ is selected from $C_1$~$C_{25}$ alkyl group or a group represented by the General Formula (3) above.

Preferably, the above-mentioned $R_a$ is selected from hydrogen, methyl, ethyl, propyl, benzyl or methoxybenzyl.

Preferably, the above-mentioned Y is selected from hydrogen, phenyl, 2-chlorophenyl, 3-chlorophenyl, 4-chlorophenyl, 2-methylphenyl, 3-methylphenyl, 4-methyl-benzene, 2-fluorophenyl, 3-fluorophenyl, 4-fluorophenyl, 2-methoxybenzene, 3-methoxyphenyl or 4-methoxyphenyl.

Preferably, $n_1+n_2$ is not greater than 5, and more preferably, $n_1+n_2$ is not greater than 3.

Preferably, the above-mentioned Q is selected from oxygen atom.

Preferably, the above-mentioned $R_1$ is selected from $C_1$~$C_{18}$ alkyl group or a group represented by General Formula (3) above.

Preferably, the above-mentioned m is selected from 2 or 3, and a total carbon number of m $R_3$s is 8~60.

Preferably, the above-mentioned $R_3$ is selected from $C_8$~$C_{22}$ alkyl group.

Preferably, k represents 0 or 1.

Preferably, the above-mentioned $m_2$ is selected from 2 or 3, and a total carbon number of $m_2$ $R_7$s is 8~60.

Preferably, $k_7$ represents 1 or 2.

Preferably, the above-mentioned $R_7$ is selected from $C_8$~$C_{22}$ alkyl group.

Preferably, the above-mentioned $R_2$ is selected from hydrogen, methyl, ethyl, propyl, isopropyl, isooctyl, benzyl or 4-methoxybenzyl.

Preferably, the above-mentioned $R_4$ is selected from hydrogen, methyl, ethyl, propyl, isopropyl, benzyl or 4-methoxybenzyl; $R_2$ and $R_4$ may jointly form a divalent alkyl group, such as ethylene, propylene, butylene and the like.

Preferably, k2 represents 2 or 3.

Preferably, when k2 is 2, $R_2$ and $R_4$ jointly form an ethylene group, and the General Formula (6) comprises a piperazine ring.

Preferably, k3 represents 2 or 3.

Preferably, $R_6$ is selected from hydrogen, methyl, ethyl, propyl, isopropyl, benzyl or 4-methoxybenzyl.

Preferably, k4 represents 0 or 1.

Preferably, k5 represents 1 or 2.

Preferably, $R_5$ is selected from hydrogen, a side chain group of natural amino acid, a $C_1$~$C_6$ alkyl group other than the side chain group of natural amino acid, or a group represented by General Formula (8).

Preferably, $R_5$ is selected from hydrogen, methyl, ethyl, isobutyl, isopropyl or a group represented by General Formula (8).

Preferably, $R_{1'}$ is selected from a $C_1$~$C_{18}$ alkyl group or a group represented by General Formula (3).

Preferably, $R_{2'}$ is selected from hydrogen, methyl, ethyl, propyl, isopropyl, benzyl or 4-methoxybenzyl.

As a preferred embodiment of the compound comprising a diphenylmethane structure of the present invention, the structure of the above-mentioned compound is selected from the following:

DPA-001

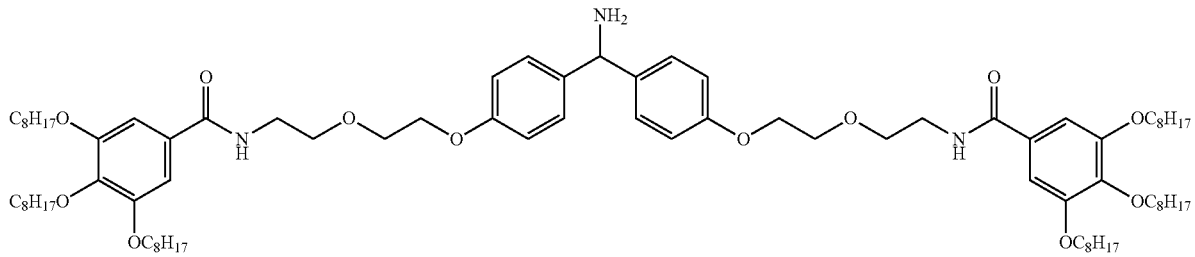

DPA-002

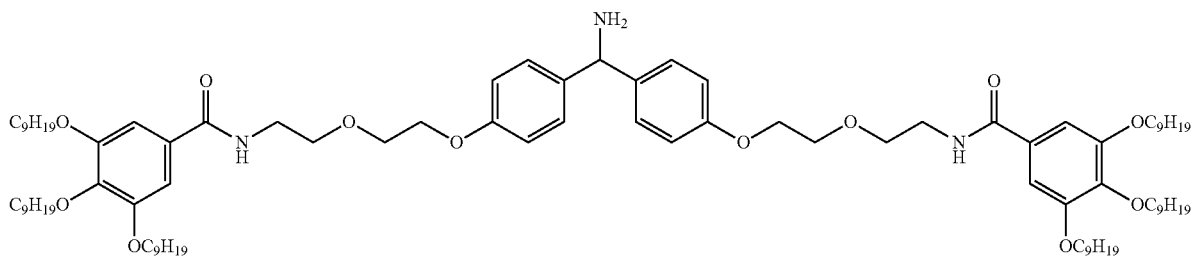

-continued
DPA-003
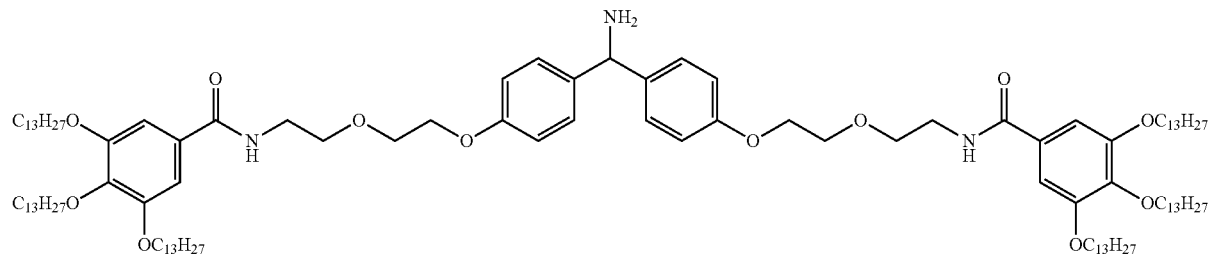
DPA-004
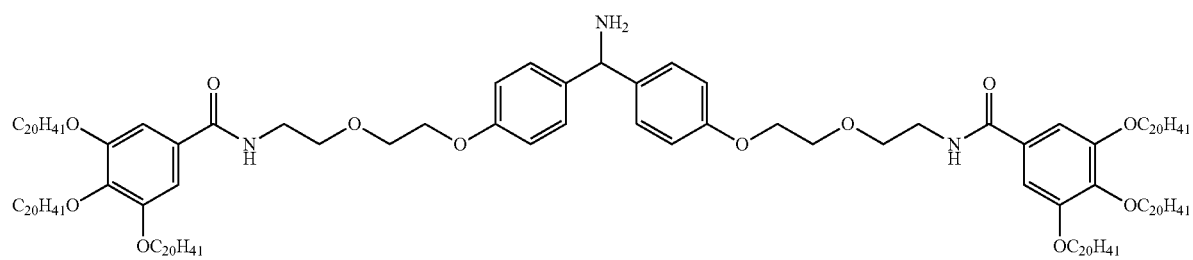
DPA-005
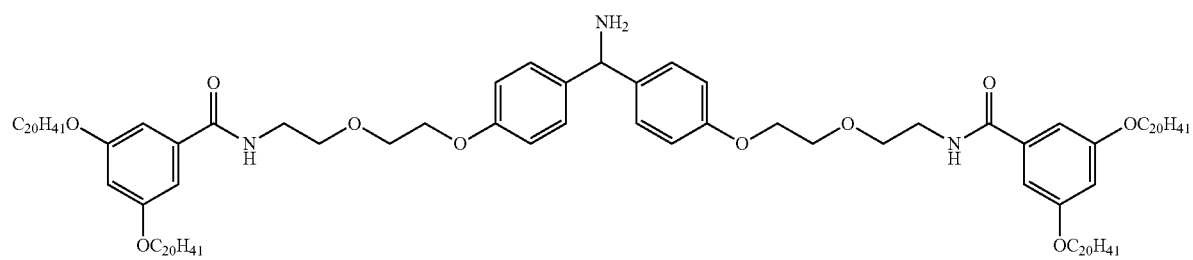
DPA-006 DPA-007
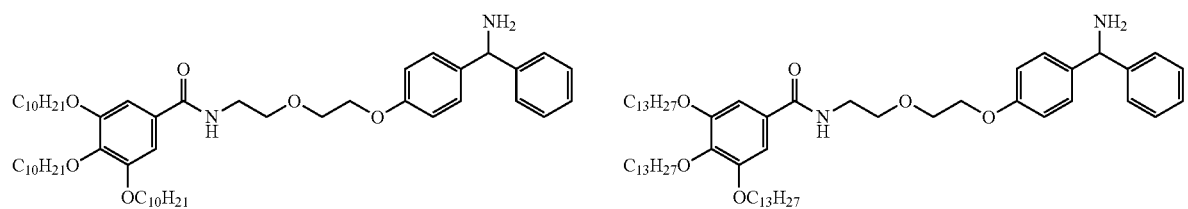
DPA-008
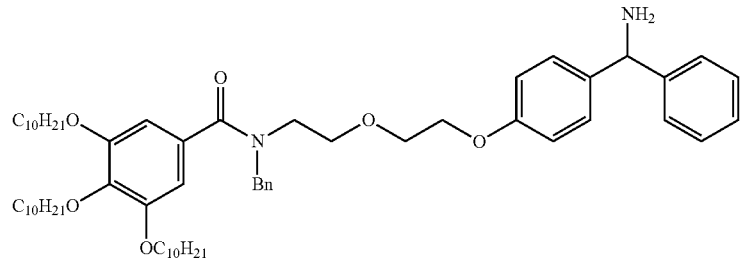

-continued
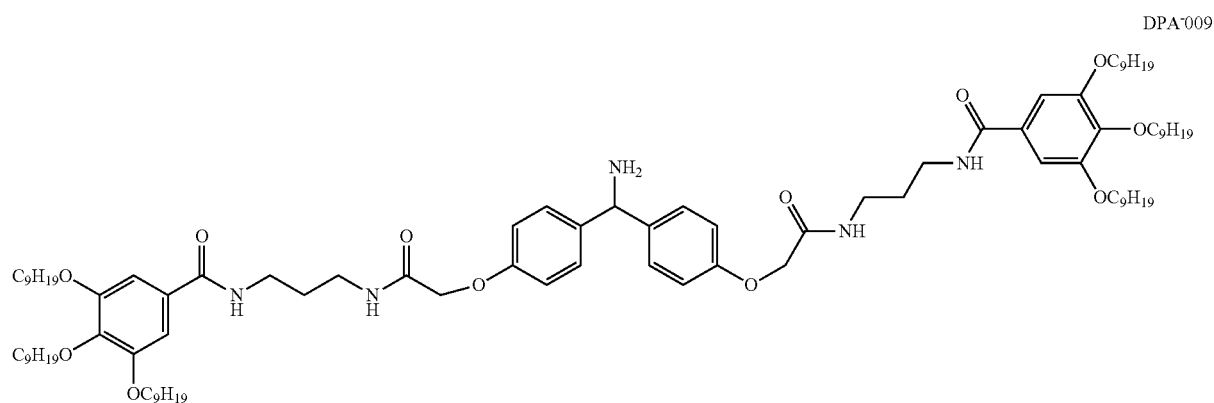
DPA-009
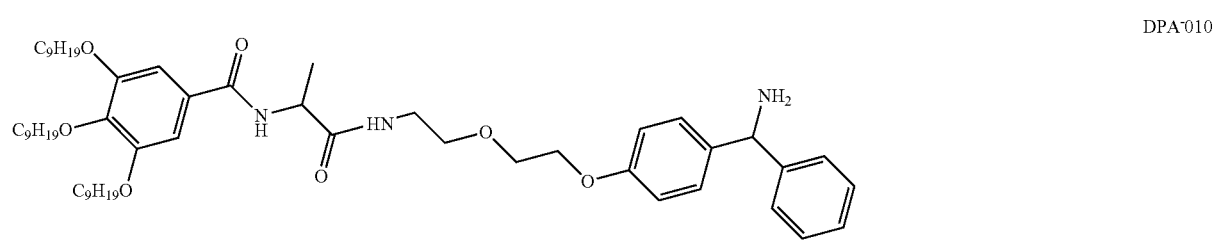
DPA-010
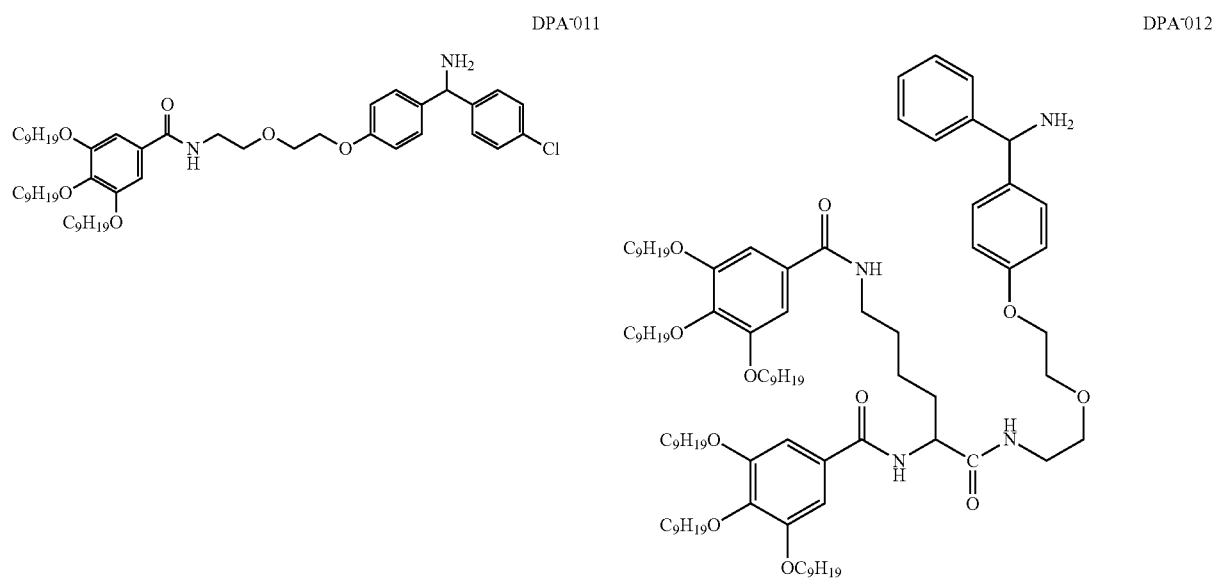
DPA-011
DPA-012

DPA-013
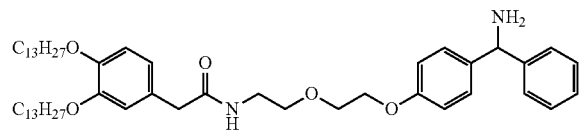
DPA-014
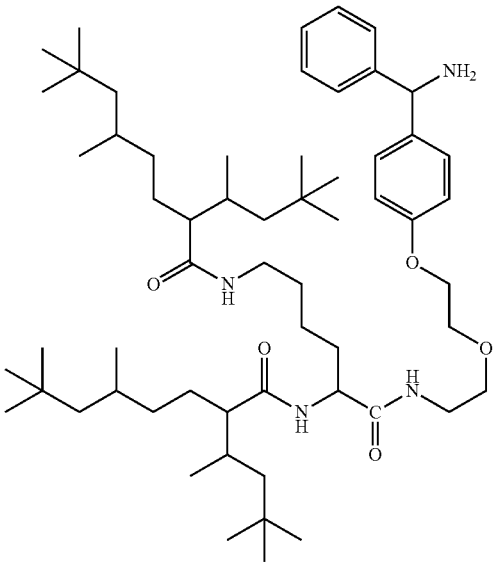
DPA-015
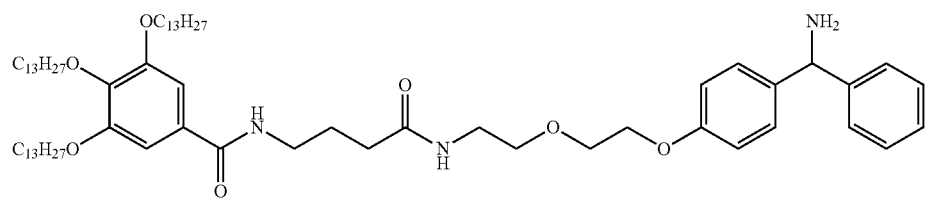
DPA-016
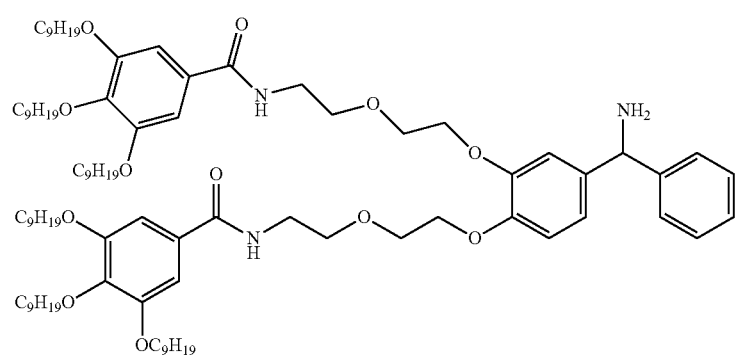
DPA-017
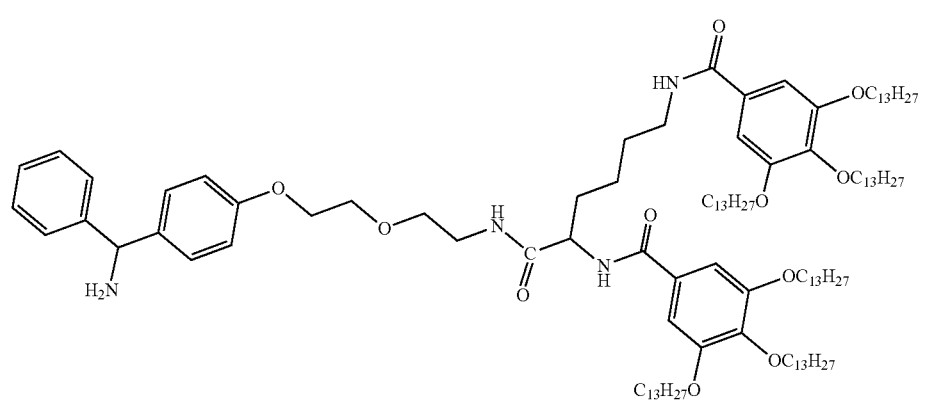

-continued
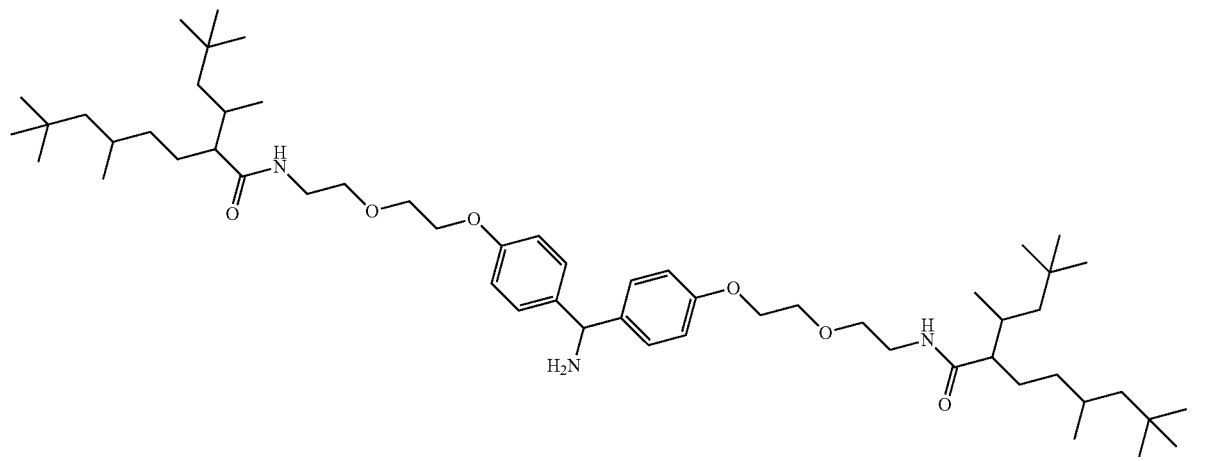
DPA-018
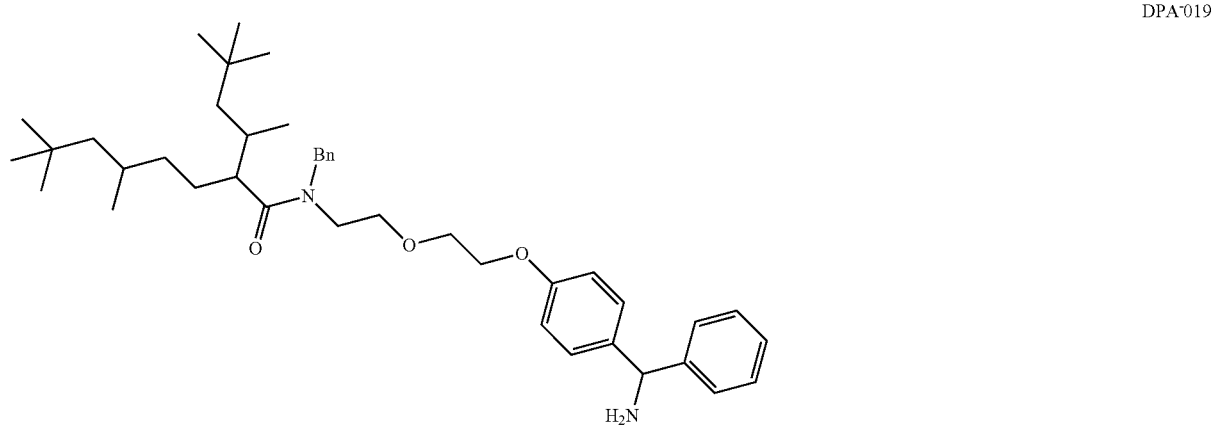
DPA-019
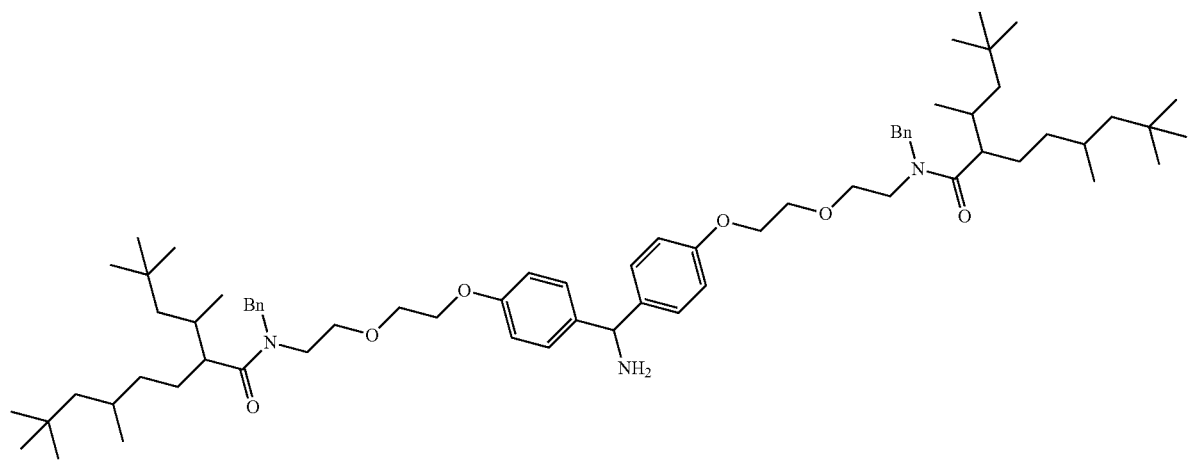
DPA-020
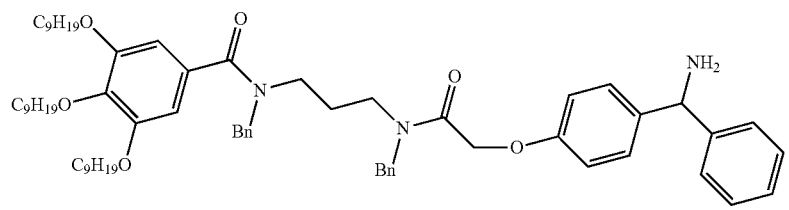
DPA-021

-continued
DPA-022
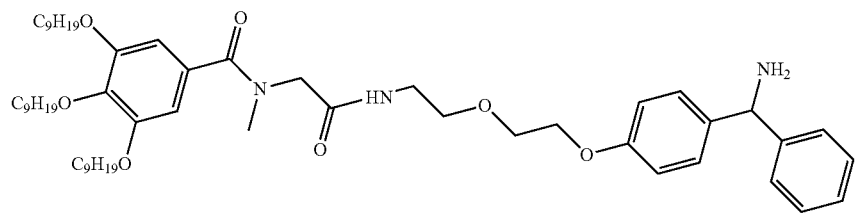
DPA-023
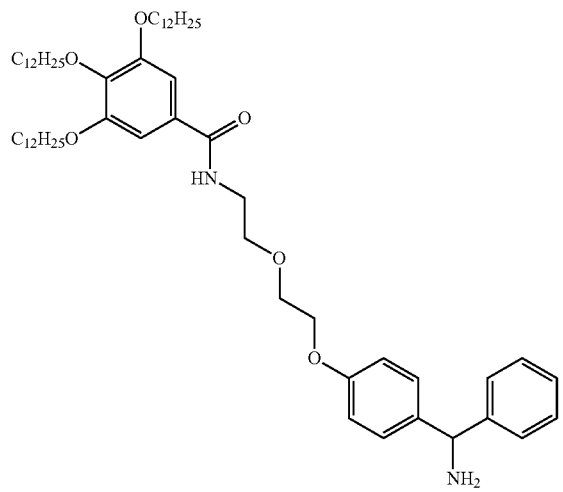
DPA-024
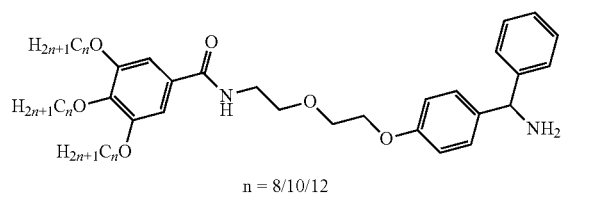
n = 8/10/12
DPA-025
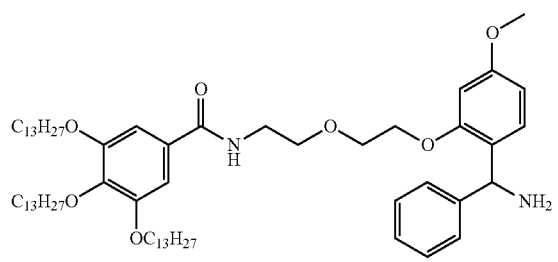
DPA-026
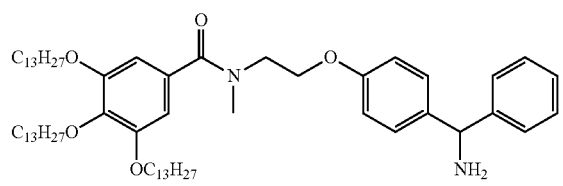
DPA-027
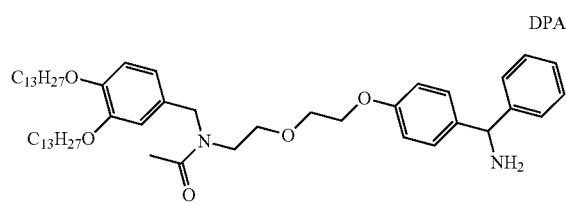
DPA-028
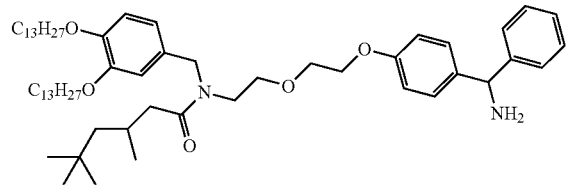
DPA-029
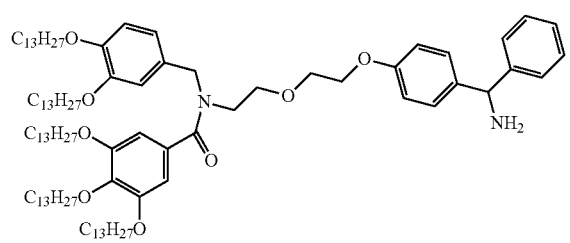
DPA-030
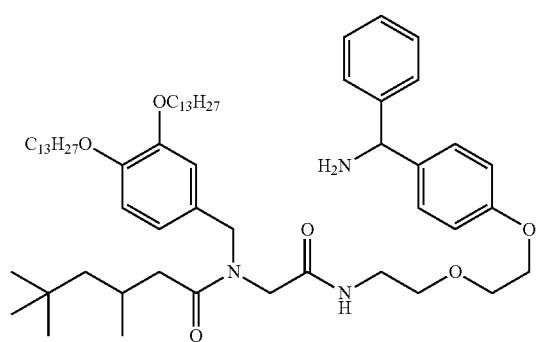

-continued

DPA-031

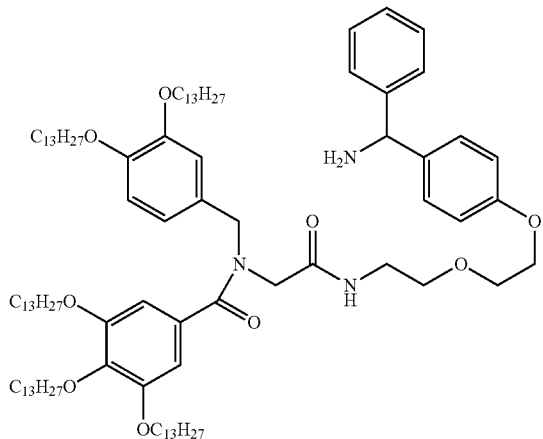

DPA-032

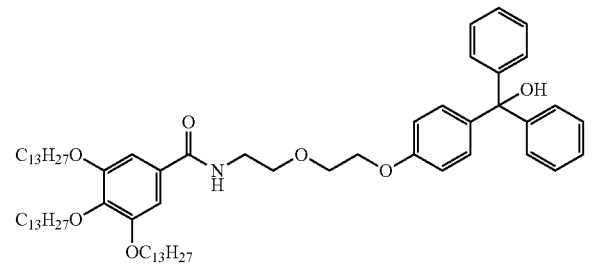

DPA-033

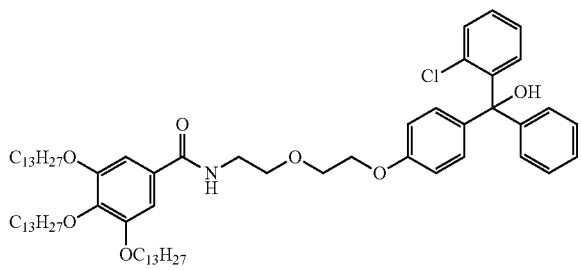

DPA-034

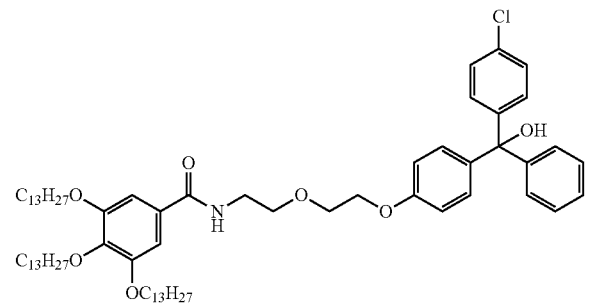

DPA-035

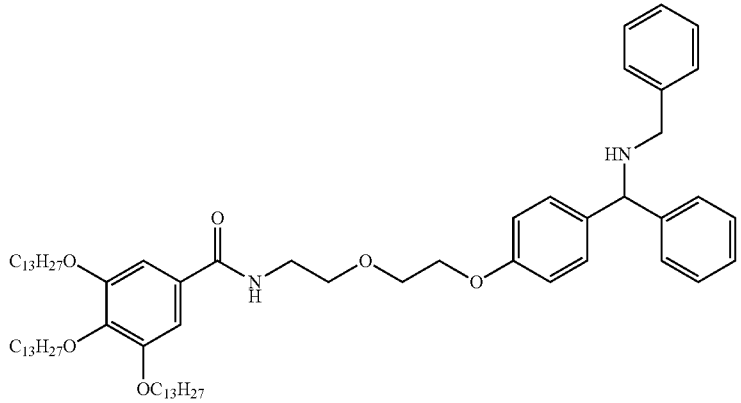

Preferably, the $C_8H_{17}$ alkyl group in the above structural formula is isooctyl, the $C_9H_{19}$ alkyl group is isononyl, the $C_{10}H_{21}$ alkyl group is isomeric decyl group, the $C_{13}H_{27}$ alkyl group is isomeric tridecyl group, and the $C_{20}H_{41}$ alkyl group is 2,3-dihydrophytyl.

As a preferred embodiment of the compound containing a diphenylmethane structure of the present invention, the compound is easily dissolved in at least one of hydrocarbon-based organic solvent, aromatic hydrocarbon-based organic solvent, ester-based organic solvent, ether-based organic solvent and water-soluble aprotic-based polar organic solvent.

Preferably, the above-mentioned hydrocarbon-based organic solvent is at least one of heptane, hexane, petroleum ether, cyclohexane and methylcyclohexane.

Preferably, the above-mentioned hydrocarbon-based organic solvent is at least one of heptane, hexane, petroleum ether and cyclohexane.

Preferably, the above-mentioned aromatic hydrocarbon-based organic solvent is at least one of toluene, ethylbenzene and xylene;

Preferably, the above-mentioned ester-based organic solvent is at least one of isopropyl acetate, tert-butyl acetate and ethyl acetate.

Preferably, the above-mentioned ether-based organic solvent is at least one of ethyl ether, isopropyl ether, methyl tert-butyl ether, methyl cyclopentyl ether and tetrahydrofuran.

Preferably, the above-mentioned ether-based organic solvent is at least one of methyl tert-butyl ether, methyl cyclopentyl ether and tetrahydrofuran.

Preferably, the above-mentioned water-soluble aprotic-based polar organic solvent is at least one of N,N-dimethylformamide, N,N-diethylformamide, N,N-dimethylacetamide, N-methyl-pyrrolidone, N-ethyl-pyrrolidone, dimethyl sulfoxide, sulfolane, 1,3-dimethylimidazolinone, 1,3-dimethyl-3,4,5,6-tetrahydro-2-pyrimidinone.

Preferably, the above-mentioned water-soluble aprotic-based polar organic solvent is at least one of N,N-dimethylformamide, N-methyl-pyrrolidone and dimethyl sulfoxide.

Preferably, at 25~30° C., the solubility of the above-mentioned compound containing a diphenylmethane structure in N,N-dimethylformamide is >1%.

Preferably, at 25~30° C., the solubility of the above-mentioned compound containing a diphenylmethane structure in N,N-dimethylformamide is >5%.

Preferably, at 25~30° C., the solubility of the above-mentioned compound containing a diphenylmethane structure in N,N-dimethylformamide is >10%.

Preferably, at 25~30° C., the solubility of the above-mentioned compound containing a diphenylmethane structure in N,N-dimethylformamide is >20%.

Preferably, at 25~30° C., the solubility of the above-mentioned compound containing a diphenylmethane structure in N,N-dimethylformamide is >30%.

Preferably, at 25~30° C., the solubility of the above-mentioned compound containing a diphenylmethane structure in N,N-dimethylformamide is >40%.

Preferably, at 25~30° C., the solubility of the above-mentioned compound containing a diphenylmethane structure in N,N-dimethylformamide is >50%.

Preferably, at 25~30° C., the solubility of the above-mentioned compound containing a diphenylmethane structure in N,N-dimethylformamide is >75%.

Preferably, at 25~30° C., the solubility of the above-mentioned compound containing a diphenylmethane structure in N,N-dimethylformamide is >100%.

Preferably, at 25~30° C., the solubility of the above-mentioned compound containing a diphenylmethane structure in a hydrocarbon-based organic solvent is >5%; and more preferably, the solubility of the above-mentioned compound containing a diphenylmethane structure in heptane is >5%.

Preferably, at 25~30° C., the solubility of the above-mentioned compound containing a diphenylmethane structure in a hydrocarbon-based organic solvent is >10%; and more preferably, the solubility of the above-mentioned compound containing a diphenylmethane structure in heptane is >10%.

Preferably, at 25~30° C., the solubility of the above-mentioned compound containing a diphenylmethane structure in a hydrocarbon-based organic solvent is >25%; and more preferably, the solubility of the above-mentioned compound containing a diphenylmethane structure in heptane is >25%.

Preferably, at 25~30° C., the solubility of the above-mentioned compound containing a diphenylmethane structure in a hydrocarbon-based organic solvent is >30%; and more preferably, the solubility of the above-mentioned compound containing a diphenylmethane structure in heptane is >30%.

Preferably, at 25~30° C., the solubility of the above-mentioned compound containing a diphenylmethane structure in a hydrocarbon-based organic solvent is >40%; and more preferably, the solubility of the above-mentioned compound containing a diphenylmethane structure in heptane is >40%.

Preferably, at 25~30° C., the solubility of the above-mentioned compound containing a diphenylmethane structure in a hydrocarbon-based organic solvent is >50%; and more preferably, the solubility of the above-mentioned compound containing a diphenylmethane structure in heptane is >50%.

Preferably, at 25~30° C., the solubility of the above-mentioned compound containing a diphenylmethane structure in a hydrocarbon-based organic solvent is >100%; and more preferably, the solubility of the above-mentioned compound containing a diphenylmethane structure in heptane is >100%.

Preferably, at 25~30° C., the solubility of the above-mentioned compound containing a diphenylmethane structure in ester-based organic solvent is >10%; and more preferably, the solubility of the above-mentioned compound containing a diphenylmethane structure in isopropyl acetate is >10%.

Preferably, at 25~30° C., the solubility of the above-mentioned compound containing a diphenylmethane structure in ester-based organic solvent is >25%; and more preferably, the solubility of the above-mentioned compound containing a diphenylmethane structure in isopropyl acetate is >25%.

Preferably, at 25~30° C., the solubility of the above-mentioned compound containing a diphenylmethane structure in ester-based organic solvent is >30%; and more preferably, the solubility of the above-mentioned compound containing a diphenylmethane structure in isopropyl acetate is >30%.

Preferably, at 25~30° C., the solubility of the above-mentioned compound containing a diphenylmethane structure in ester-based organic solvent is >40%; and more preferably, the solubility of the above-mentioned compound containing a diphenylmethane structure in isopropyl acetate is >40%.

Preferably, at 25~30° C., the solubility of the above-mentioned compound containing a diphenylmethane structure in ester-based organic solvent is >50%; and more preferably, the solubility of the above-mentioned compound containing a diphenylmethane structure in isopropyl acetate is >50%.

Preferably, at 25~30° C., the solubility of the above-mentioned compound containing a diphenylmethane structure in ester-based organic solvent is >70%; and more preferably, the solubility of the above-mentioned compound containing a diphenylmethane structure in isopropyl acetate is >70%.

Preferably, at 25~30° C., the solubility of the above-mentioned compound containing a diphenylmethane structure in ester-based organic solvent is >75%; and more preferably, the solubility of the above-mentioned compound containing a diphenylmethane structure in isopropyl acetate is >75%.

Preferably, at 25~30° C., the solubility of the above-mentioned compound containing a diphenylmethane structure in ester-based organic solvent is >100%; and more preferably, the solubility of the above-mentioned compound containing a diphenylmethane structure in isopropyl acetate is >100%.

Preferably, at 25~30° C., the solubility of the above-mentioned compound containing a diphenylmethane structure in ether-based organic solvent is >10%; and more preferably, the solubility of the above-mentioned compound containing a diphenylmethane structure in methyl tert-butyl ether is >10%.

Preferably, at 25~30° C., the solubility of the above-mentioned compound containing a diphenylmethane structure in ether-based organic solvent is >30%; and more preferably, the solubility of the above-mentioned compound containing a diphenylmethane structure in methyl tert-butyl ether is >30%.

Preferably, at 25~30° C., the solubility of the above-mentioned compound containing a diphenylmethane structure in ether-based organic solvent is >40%; and more preferably, the solubility of the above-mentioned compound containing a diphenylmethane structure in methyl tert-butyl ether is >40%.

Preferably, at 25~30° C., the solubility of the above-mentioned compound containing a diphenylmethane structure in ether-based organic solvent is >50%; and more preferably, the solubility of the above-mentioned compound containing a diphenylmethane structure in methyl tert-butyl ether is >50%.

Preferably, at 25~30° C., the solubility of the above-mentioned compound containing a diphenylmethane structure in ether-based organic solvent is >75%; and more preferably, the solubility of the above-mentioned compound containing a diphenylmethane structure in methyl tert-butyl ether is >75%.

Preferably, at 25~30° C., the solubility of the above-mentioned compound containing a diphenylmethane structure in ether-based organic solvent is >100%; and more preferably, the solubility of the above-mentioned compound containing a diphenylmethane structure in methyl tert-butyl ether is >100%.

The compound of the present invention may be prepared by the following synthetic route:

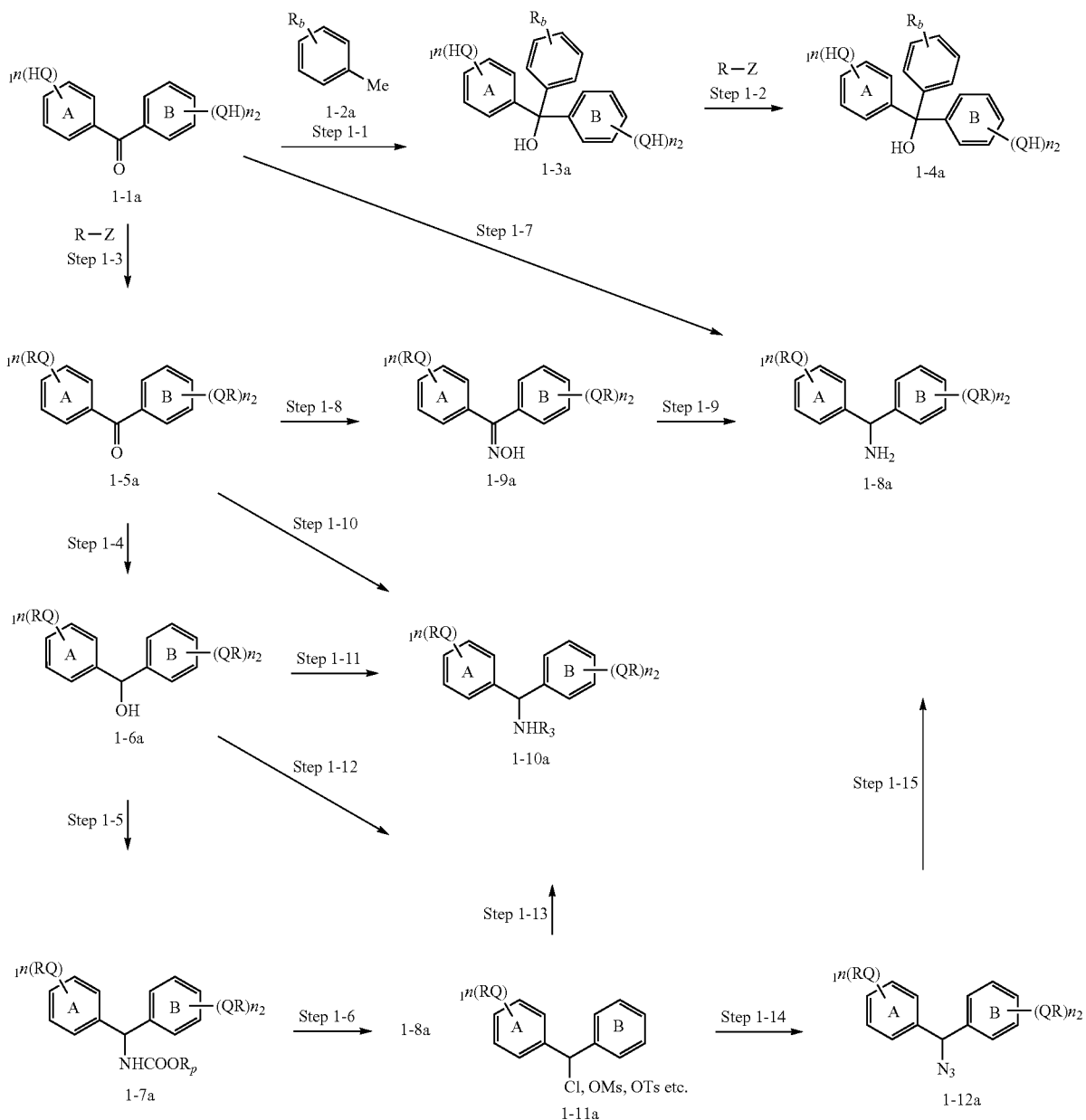

A compound of X=OH, Y=phenyl group or substituted phenyl group can be synthesized through the Step 1-1 and Step 1-2 from a ketone;

A compound of X=OH, $NHR_a$, $R_a$ representing a hydrogen atom, an alkyl group or an aralkyl group, and Y=hydrogen atom can be synthesized through the Step 1-3 to Step 1-4 from a ketone;

The OH can be converted into an active compound such as chlorine, bromine, iodine, methanesulfonate and p-toluenesulfonate and the like through a conventional reaction.

In a fourth aspect, the present invention provides a peptide synthesis method, and the peptide synthesis method comprises using the above-mentioned compound containing a diphenylmethane structure.

Preferably, the above-mentioned peptide synthesis method comprises the following steps:

1) carrier inserting: the above-mentioned compound containing a diphenylmethane structure is used as a carrier and is connected to a N-protected amino acid or N-protected peptide compound through a conventional reaction to obtain

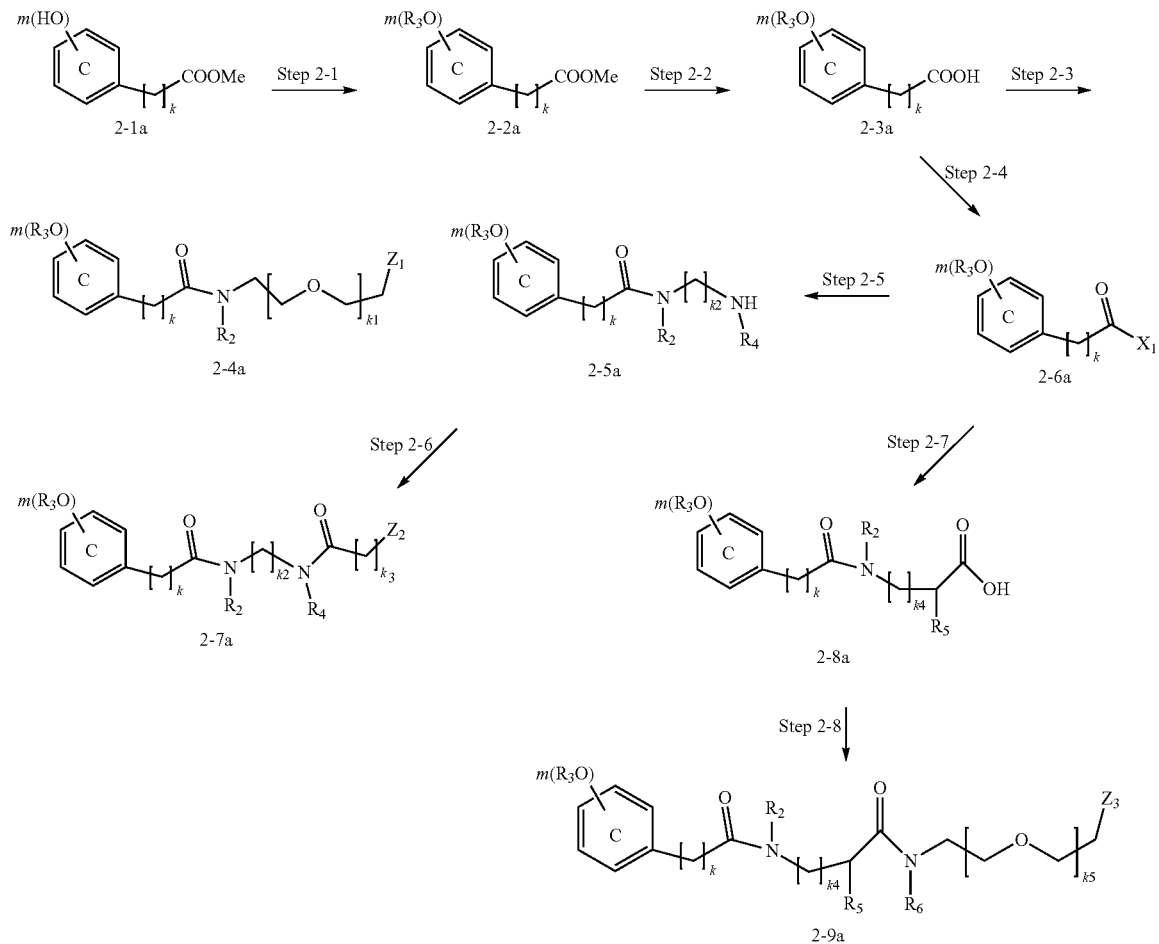

According to the above steps, a active substance R—Z of R as represented by the General Formulas (5), (6) and (7) can be synthesized.

In a second aspect, the present invention provides a protective reagent for C-terminal of an amino acid or peptide, and the protective reagent comprises the above-mentioned compound containing a diphenylmethane structure.

In a third aspect, the present invention provides an use of the above-mentioned compound containing a diphenylmethane structure as a peptide synthesis reagent in homogeneous or heterogeneous solvent system.

In addition, those skilled in the art can add other substances to the above-mentioned reagents according to conventional selection and prepare a required compounds or complexes according to needs.

a N-protected amino acid or N-protected peptide compound whose C-terminal is protected by the carrier comprising a diphenylmethane structure;

2) N-terminal deprotecting: the N-protected amino acid or N-protected peptide compound whose C-terminal is protected by the carrier comprising a diphenylmethane structure is dissolved in a solvent, a solution of N-terminal-protected deprotection reagent is added to form a homogeneous or heterogeneous system to perform a N-terminal deprotecting, a highly polar solvent is added for extraction, and a solution of N-deprotected amino acid or N-deprotected peptide compound whose C-terminal is protected by the carrier comprising a diphenylmethane structure is obtained;

3) peptide chain extending: to the solution of N-deprotected amino acid or N-deprotected peptide compound whose C-terminal is protected by the carrier comprising a diphenylmethane structure, a solution of N-protected amino acid or N-protected peptide is added, and then a condensation reagent solution is added to form a homogeneous or heterogeneous system to perform a condensation reaction, a highly polar solvent is added for extraction, and a solution of N-protected amino acid or N-protected peptide compound whose C-terminal is protected by the carrier comprising a diphenylmethane structure is obtained;

4) the step 2) and step 3) are repeated to insert a next amino acid until a complete peptide chain is obtained.

Preferably, the solution of N-protected amino acid or N-protected peptide compound whose C-terminal is protected by the carrier comprising a diphenylmethane structure in step 2) and the solution of N-terminal-protected deprotection reagent in step 2) form a heterogeneous system.

Preferably, the solution of N-deprotected amino acid or N-deprotected peptide compound whose C-terminal is protected by the carrier comprising a diphenylmethane structure in step 3), and the solution of N-protected amino acid or N-protected peptide and the condensation reagent solution in step 3) form a heterogeneous system.

Preferably, the solvent dissolving the N-protected amino acid or N-protected peptide compound whose C-terminal is protected by the carrier comprising a diphenylmethane structure in step 2) and the solvent in the solution of N-deprotected amino acid or N-deprotected peptide compound whose C-terminal is protected by the carrier comprising a diphenylmethane structure in step 3) are independently selected from hydrocarbons, or a mixed solvent formed by hydrocarbons and at least one of esters, ethers and halogenated hydrocarbons.

It should be noted that the content of the hydrocarbons in the mixed solvent formed by hydrocarbons and at least one of esters, ethers and halogenated hydrocarbons is subject to not affecting the formation of a heterogeneous system.

Preferably, the solvent dissolving the N-protected amino acid or N-protected peptide compound whose C-terminal is protected by the carrier comprising a diphenylmethane structure in step 2) and the solvent in the solution of N-deprotected amino acid or N-deprotected peptide compound whose C-terminal is protected by the carrier comprising a diphenylmethane structure in step 3) are independently selected from at least one of hexane, cyclohexane, methylcyclohexane, heptane and petroleum ether; or a mixed solvents formed by at least one of hexane, cyclohexane, methylcyclohexane, heptane and petroleum ether and at least one of isopropyl acetate, tert-butyl acetate, ethyl acetate, ethyl ether, isopropyl ether, methyl tert-butyl ether, methyl cyclopentyl ether, dichloromethane and chloroform.

Preferably, the solvent dissolving the N-terminal-protected deprotection reagent in step 2), and the solvent dissolving the N-protected amino acid or N-protected peptide and the condensation reagent in step 3) are independently selected from an amide-based solvent.

Preferably, the above-mentioned amide-based solvent is selected from at least one of N,N-dimethylformamide, N,N-diethylformamide, N,N-dimethylacetamide, N-methyl-pyrrolidone, N-ethyl-pyrrolidone, 1,3-dimethylimidazolinone and 1,3-dimethyl-3,4,5,6-tetrahydro-2-pyrimidinone.

Preferably, the highly polar solvents in the above step 2) and step 3) are independently selected from at least one of water, alcohols, nitriles, amides, sulfoxides, sulfones and water-soluble alcohol ethers.

Preferably, the highly polar solvents in the above step 2) and step 3) are independently selected from at least one of water, methanol, acetonitrile, N,N-dimethylformamide, N-methyl-pyrrolidone, dimethyl sulfoxide, sulfolane, 1,3-dimethylimidazolinone, 1,3-dimethyl-3,4,5,6-tetrahydro-2-pyrimidinone.

It should be noted that in step 2), when the N-protected amino acid or N-protected peptide compound whose C-terminal is protected by the carrier comprising a diphenylmethane structure is dissolved in a solvent and a solution of N-terminal-protected deprotection reagent is added to form a homogeneous or heterogeneous system to perform a N-terminal deprotecting, the solvent dissolving the N-protected amino acid or N-protected peptide compound whose C-terminal is protected by the carrier comprising a diphenylmethane structure does not contain hydrocarbons or contains a part of hydrocarbons, but this part of hydrocarbons does not affect the formation of a homogeneous system. The solvent dissolving the N-terminal-protected deprotection reagent and the solvent dissolving the N-protected amino acid or N-protected peptide compound whose C-terminal is protected by the carrier comprising a diphenylmethane structure may be at least one of ester-based solvent, ether-based solvent, halogenated hydrocarbon-based or amide-based solvent; preferably, at least one of ethyl acetate, isopropyl acetate, tert-butyl acetate, isopropyl ether, methyl tert-butyl ether, methyl cyclopentyl ether, tetrahydrofuran, dichloromethane, chloroform, N,N-dimethylformamide, N-methyl-pyrrolidone, 1,3-dimethylimidazolinone and 1,3-dimethyl-3,4,5,6-tetrahydro-2-pyrimidinone; similarly, in step 3), when the solution of N-deprotected amino acid or N-deprotected peptide compound whose C-terminal is protected by the carrier comprising a diphenylmethane structure is added with the solution of N-protected amino acid or N-protected peptide, and then added with the condensation reagent solution to form a homogeneous system to perform a condensation reaction, the solvent of the solution of N-deprotected amino acid or N-deprotected peptide compound whose C-terminal is protected by the carrier comprising a diphenylmethane structure does not contain hydrocarbons or contains a part of hydrocarbons, but this part of hydrocarbons does not affect the formation of a homogeneous system. The solvent dissolving the N-protected amino acid or N-protected peptide compound and the condensation reagent and the solvent dissolving the N-deprotected amino acid or N-deprotected peptide compound whose C-terminal is protected by the carrier comprising a diphenylmethane structure may be selected from at least one of ester-based solvent, ether-based solvent or amide-based solvent, preferably, at least one of ethyl acetate, isopropyl acetate, tert-butyl acetate, dichloromethane, chloroform, tetrahydrofuran, N,N-dimethylformamide, N-methyl-pyrrolidone, 1,3-dimethylimidazolinone and 1,3-dimethyl-3,4,5,6-tetrahydro-2-pyrimidinone.

In the peptide synthesis method of the present invention, a target product and impurities can be well separated only by adding a highly polar solvent, especially in a heterogeneous system, thereby greatly simplifying the operation steps of the post-treatment.

Preferably, the amount of the above-mentioned N-protected amino acid or N-protected peptide is 0.8~3.0 equivalents of the compound containing a diphenylmethane structure, and the amount of the condensation reagent is 0.8~3.0 equivalents of the compound containing a diphenylmethane structure.

More preferably, the amount of the above-mentioned N-protected amino acid or N-protected peptide is 1~1.1 equivalents of the compound containing a diphenylmethane structure, and the amount of the condensation reagent is 1~1.2 equivalents of the compound containing a diphenylmethane structure.

In the peptide synthesis reaction, the compound of the present invention is introduced into an amino acid or peptide as a protective group for C-terminal. During the process of introducing the compound of the present invention, the compound of X=OH may be firstly converted into an equivalent active substance, such as a halide and a sulfonate, and then reacted with an amino acid or peptide, or it may be directly esterified or amidated. The introduction of a compound of X=NHR$_a$ may be achieved by reacted with amino acid and peptide through a conventional condensation method, and the operation step can be the same as or different from step 3). The reaction may be carried out in a homogeneous and heterogeneous solvent system, wherein the inserting reaction of a carrier of X=OH is preferably carried out in a homogeneous solvent system, and the inserting reaction of a carrier of X=NHR$_a$ is preferably carried out in a heterogeneous solvent system.

The beneficial effects of the present invention are as follows:

(1) The present invention provides a protective carrier which can be used for the liquid-phase synthesis of peptide. The peptide synthesis reaction using this protective carrier has a fast reaction speed and a high reagent utilization rate in a suitable solvent system; the post-treatment can perform an effective purification through a simple liquid-liquid extraction and separation, and a product with a higher purity can be finally obtained; and during the synthesis process, a change of solubility is small, the operation process has a strong universality, and the it can be developed into a universal production method.

(2) The compound containing a diphenylmethane structure of the present invention contains a hydroxyl group, an amino group, a substituted amino group and an active group, and can be used as a C-terminal protective reagent of amino acid or peptide. The compound of the present invention comprises a non-polar structure and a polar structure, and is soluble in both non-polar organic solvent and polar solvent, thus, it is suitable as a protective carrier in a homogeneous or heterogeneous mixed solvent system composed of a non-polar organic solvent and a polar solvent, and particularly, in a heterogeneous system composed of hydrocarbons or a mixed solvent formed of hydrocarbons and at least one solvent of ethers, esters and halogenated alkane; and amide-based polar solvent, to perform a synthesis reaction of peptide. The peptide synthesis reaction using this kind of carrier has the following advantages: ① the reaction speed is fast and the by-products is reduced; ② the utilization rate of reaction reagent is high, the used amount of reagent is small, the cost is low, and the "three wastes" is reduced; ③ the separation effect of the post-treatment which extracting and separating the impurities and product is good, the product purity is high; ④ during the synthesis process, the solubility and reaction rate of the intermediate compound change little, the inserting process of amino acid or peptide fragment has a good repeatability, the operation is simple, the universality is strong, and it is suitable as a general-purpose production method.

BEST MODE

In order to better illustrate the objectives, technical solutions and advantages of the present invention, the present invention will be further described below in conjunction with specific embodiments.

Unless otherwise specified in this specification, all technical and scientific terms used herein have the same meanings as commonly understood by those skilled in the art. Unless otherwise mentioned, the raw material compounds are all purchased on the market or prepared by a common general method. The various preparation methods used will have different yield and product purity due to the difference in reaction conditions.

In this specification and in the following examples, the substances represented by the following abbreviations are:
DCM: dichloromethane
DIPEA: N,N-diisopropylethylamine
DMAP: 4-dimethylaminopyridine
DMF: N,N-dimethylformamide
EA: ethyl acetate
EDCI: 1-ethyl-(3-dimethylaminopropyl)carbodiimide hydrochloride
HBTU: O-benzotriazole-tetramethylurea hexafluorophosphate
HOBt: 1-hydroxybenzotriazole
HONB: N-hydroxy-5-norbornene-2,3-dicarboximide
PE: petroleum ether
TFA: trifluoroacetic acid
TIS: triisopropylsilane Example 1

Synthesis of 4,4'-di(2-(2-(3,4,5-tris(isooctyloxy)-benzamido)-ethoxy)-ethoxy) benzhydrylamine (DPA-001)

Methyl 3,4,5-trihydroxybenzoate (18.4 g, 0.1 mol), isooctyl bromide (2-ethyl-hexyl bromide) (63.7 g, 0.33 mol), potassium carbonate (55.2 g, 0.4 mol) and DMF (150 mL) were mixed at room temperature, heated to 110-120° C. to reacted for 12 h. Cooled to room temperature and poured into a mixed liquid of petroleum ether (150 mL) and water (150 mL) under stirring. The lower layer was separated, and the upper layer of petroleum ether solution was washed with water (200 mL×2), concentrated to obtain a crude product of oily intermediate 1-2.

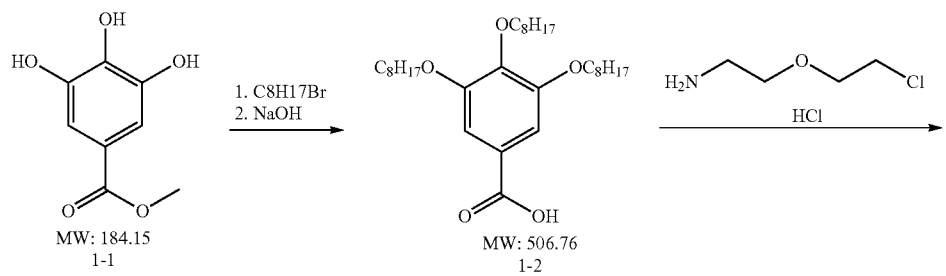

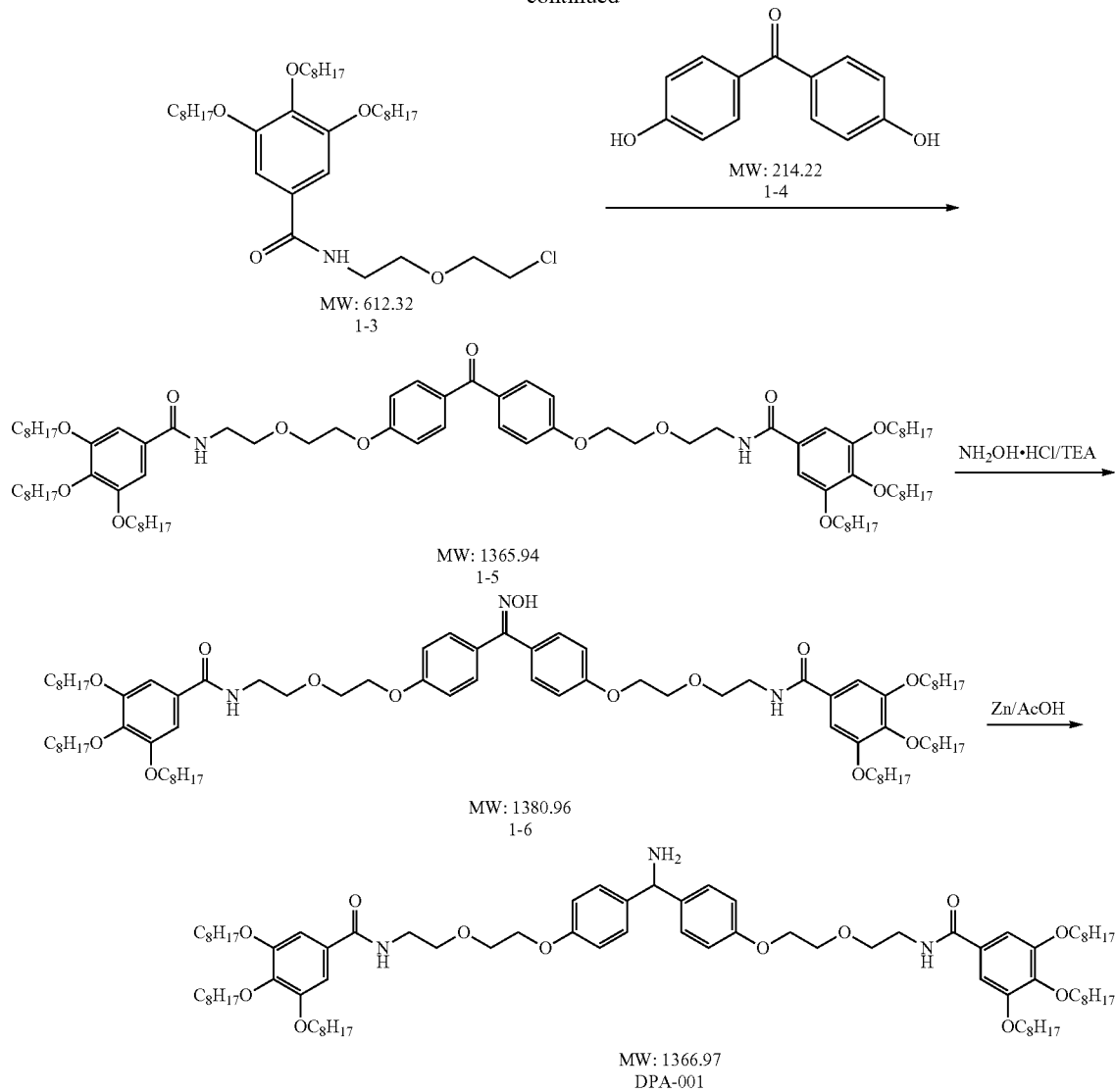

The crude ester of intermediate 1-2 was dissolved in tetrahydrofuran (100 mL), methanol (50 mL) and 30% NaOHaq (67 g) were added, and reacted for 3 h under stirring. Petroleum ether (100 mL) and water (200 mL) were added and stirred for 10 min, then the lower layer was separated; 2N hydrochloric acid (100 mL) was added and stirred for another 10 min, and the lower layer was separate; the upper layer was washed with water until the pH was 6-7, and concentrated to obtain 48.0 g of 3,4,5-tris(isooctyloxy)-benzoic acid.

3,4,5-tris(isooctyloxy)-benzoic acid (45.5 g, 0.09 mol), 2-(2-chloroethyl)oxy-ethylamine hydrochloride (16.0 g, 0.1 mol) and dichloromethane (200 mL) were mixed and stirred magnetically, and cooled to 5-10° C.; HOBt (13.5 g, 0.1 mol) and EDCI (19.2, 0.1 mol) were added sequentially; the temperature was kept at 5-10° C. for 10 min, the cold bath was removed, and the temperature was naturally raised to room temperature to react for 3 h. Washed with water (100 mL), saturated sodium bicarbonate (100 mL×2), 1N hydrochloric acid (50 mL) and saturated salt solution (50 mL) sequentially, and concentrated to obtain 55.1 g of 2-(2-(3,4,5-triisooctyloxy-benzamido)-ethoxy)-ethyl chloride.

2-(2-(3,4,5-tris(isooctyloxy)-benzamido)-ethoxy)-ethyl chloride (55.1 g, 0.09 mmol), 4,4'-dihydroxybenzophenone (8.6 g, 0.04 mol), potassium carbonate (37.3 g, 0.27 mol), potassium iodide (0.1 g) and DMF (100 mL) were mixed and stirred mechanically, and heated to 100-110° C. to react for 8 h. Cooled to room temperature and poured into a mixed liquid of petroleum ether (150 mL) and water (150 mL) under stirring. The lower layer was separated, the upper layer was washed with water (200 mL×2), and concentrated to obtain a crude product of 4,4'-di(2-(2-(3,4,5-tris(isooctyloxy)-benzamido)-ethoxy)-ethoxy)-benzophenone.

The above crude product was dissolved in tetrahydrofuran (100 mL) and ethanol (100 mL), and hydroxylamine hydrochloride (5.6 g, 0.08 mol) and triethylamine (8 g, 0.08 mol) were added at room temperature; the reaction solution was heated to 75-80° C. to react for 12 h. Cooled to room temperature and poured into a mixed liquid of petroleum ether (150 mL) and water (200 mL) under stirring. The lower layer was separated, the upper layer was washed with water (200 mL*2), and concentrated to obtain a crude product of 4,4'-di(2-(2-(3,4,5-triisooctyloxy-benzamido)-ethoxy)-ethoxy)-benzophenone oxime. The above crude oxime was dissolved in tetrahydrofuran (100 mL) and acetic acid (50 mL) was added, heated to 55-60° C., and zinc powder (7.8 g, 0.12 mol) were added in batches. After the addition was completed, the reaction was continued for 2 h, the excess zinc powder was removed by filtration, and tetrahydrofuran and acetic acid were removed by concentration. Petroleum ether (150 mL) was added to re-dissolved, washed with 10% $NaOH_{aq}$ (100 mL×2) and saturated salt solution sequentially, and concentrated to obtain a crude product of DPA-001. Purified by column chromatography (100% PE→100EA) to obtain 20.0 g of 4,4'-di(2-(2-(3,4,5-tris(isooctyloxy)-benzamido)-ethoxy)-ethoxy)benzhydrylamine (DPA-001). $^1$H-NMR (400 MHz, CDCl$_3$): δ0.85-1.00 (m, 36H), 1.30-1.80 (m, 54H), 3.60-4.20 (m, 28H), 5.10-5.20 (s, 1H), 6.65-6.70 (m, 2H), 6.80-6.90 (d, 4H), 7.00 (s, 4H), 7.20-7.25 (d, 4H); HRMS TOF [M+1]$^+$: 1367.0119.

Example 2

Synthesis of 4,4'-di(2-(2-(3,4,5-tris(isononyloxy)-benzamido)-ethoxy)-ethoxy) benzhydrylamine (DPA-002)

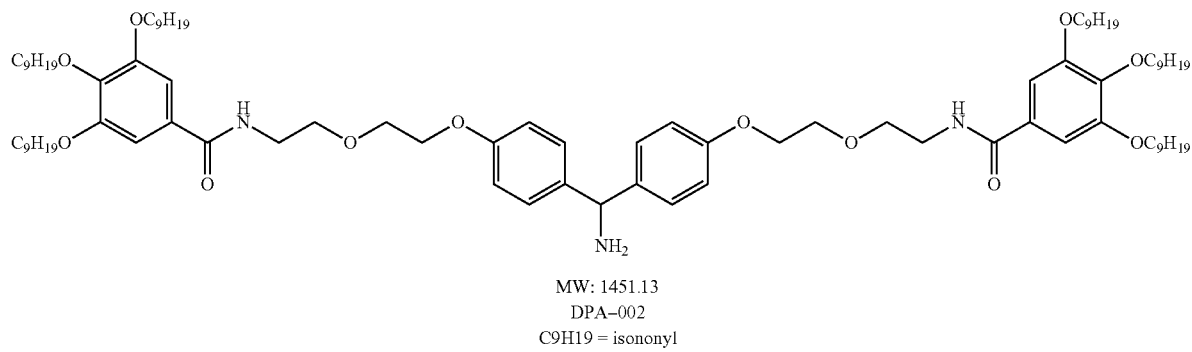

MW: 1451.13
DPA-002
C9H19 = isononyl

The 4,4'-di(2-(2-(3,4,5-tris(isononyloxy)-benzamido)-ethoxy)-ethoxy)benzhydrylamine (DPA-002) was synthesized according to the steps in Example 1 by using isononyl bromide (3,5,5-trimethyl-hexyl bromide) instead of isooctyl bromide. $^1$H-NMR (400 MHz, CDCl$_3$): δ0.80-1.40 (m, 84H), 1.50-2.00 (m, 18H), 3.60-4.20 (m, 28H), 5.10-5.20 (s, 1H), 6.65-6.70 (m, 2H), 6.80-6.90 (d, 4H), 7.00 (s, 4H), 7.20-7.25 (d, 4H); HRMS TOF [M+1]$^+$: 1451.1058.

Example 3

Synthesis of 4,4'-di(2-(2-(3,4,5-tris(isomeric tridecyloxy)-benzamido)-ethoxy)-ethoxy)-benzhydrylamine (DPA-003)

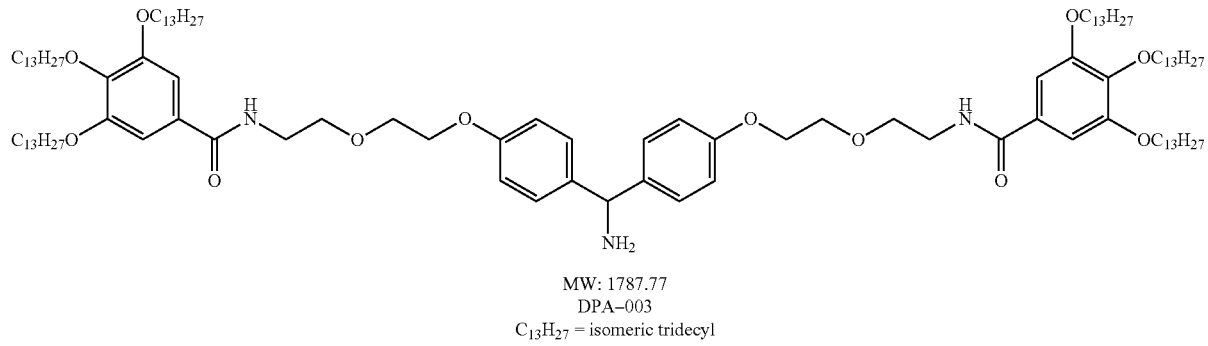

MW: 1787.77
DPA-003
C$_{13}$H$_{27}$ = isomeric tridecyl

The 4,4'-di(2-(2-(3,4,5-tris(isomeric tridecyloxy)-benzamido)-ethoxy)-ethoxy)-benzhydrylamine (DPA-003) was synthesized according to the steps in Example 1 by using isomeric tridecyl bromide (prepared from Exxal 13 by bromination) instead of isooctyl bromide. $^1$H-NMR (400 MHz, CDCl$_3$): δ0.70-1.90 (m, 150H), 3.65-4.15 (m, 28H), 5.10-5.20 (s, 1H), 6.65-6.70 (m, 2H), 6.80-6.90 (d, 4H), 7.00 (s, 4H), 7.20-7.25 (d, 4H); HRMS TOF [M+1]$^+$: 1787.3814;

Preparation of Isomeric Tridecyl Bromide
(Preparation of Bromide)

Isomeric tridecyl alcohol (Exxal 13) (100 mL) and 37% HBr (300 mL) were mixed in a three-necked flask. Under mechanical stirring, concentrated sulfuric acid (30 mL) was slowly added, and the mixed reaction solution was heated to 115-120° C. to react. The reaction was stopped after the alcohol was <0.5% by GC analysis. The temperature was lowered to 50° C. or less, and petroleum ether (100 mL) was added for extraction. The petroleum ether layer was washed with water to neutrality, and the petroleum ether was removed under reduced pressure to obtain an isomeric tridecyl bromide.

Example 4

Synthesis of 4,4'-di(2-(2-(3,4,5-tris(2,3-dihydrophytoxy)-benzamido)-ethoxy)-ethoxy)-benzhydrylamine (DPA-004)

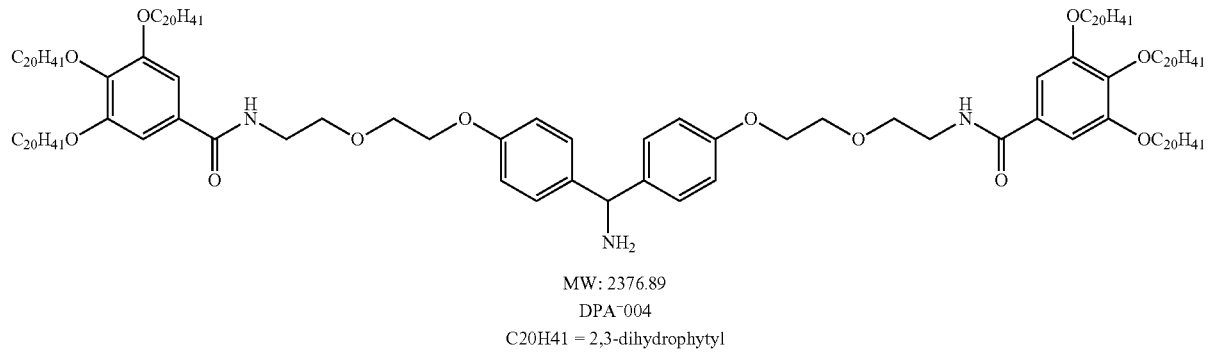

MW: 2376.89
DPA-004
C20H41 = 2,3-dihydrophytyl

The 4,4'-di(2-(2-(3,4,5-tris(2,3-dihydrophytoxy)-benzamido)-ethoxy)-ethoxy)-benzhydrylamine (DPA-004) was synthesized according to the steps in Example 1 by using 2,3-dihydrophytyl bromide (3,7,11,15-tetramethyl-hexadecyl bromide) instead of isooctyl bromide. $^1$H-NMR (400 MHz, CDCl$_3$): δ0.70-1.90 (m, 234H), 3.65-4.15 (m, 28H), 5.10-5.20 (s, 1H), 6.65-6.70 (m, 2H), 6.80-6.90 (d, 4H), 7.00 (s, 4H), 7.20-7.25 (d, 4H); HRMS TOF [M+1]$^+$: 2376.8867.

Example 5

Synthesis of 4,4'-di(2-(2-(3,5-di(2,3-dihydrophytoxy)-benzamido)-ethoxy)-ethoxy)-benzhydrylamine (DPA-005)

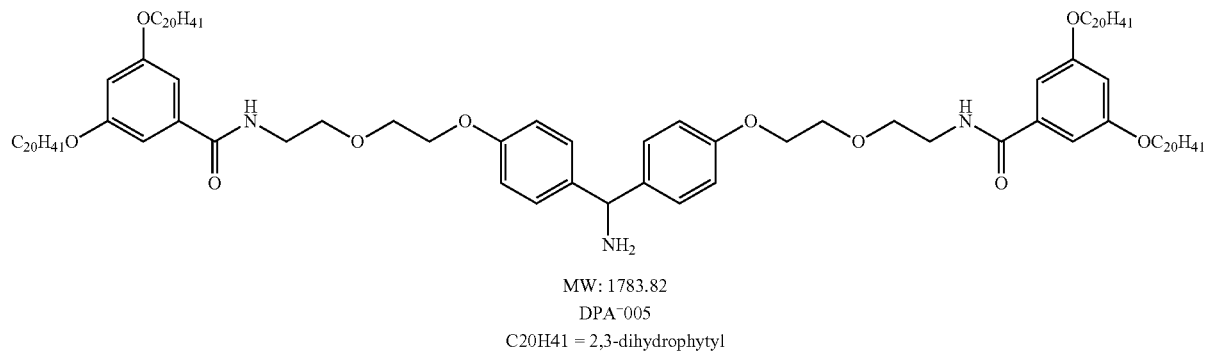

MW: 1783.82
DPA-005
C20H41 = 2,3-dihydrophytyl

The 4,4'-di(2-(2-(3,5-di(2,3-dihydrophytoxy)-benzamido)-ethoxy)-ethoxy)-benzhydrylamine (DPA-005) was synthesized according to the steps in Example 1 by using 2,3-dihydrophytyl bromide instead of isooctyl bromide and using methyl 3,5-dihydroxybenzoate instead of methyl 3,4,5-trihydroxybenzoate. $^1$H-NMR (400 MHz, CDCl$_3$): δ0.70-1.90 (m, 156H), 3.65-4.15 (m, 28H), 5.10-5.20 (s, 1H), 6.65-6.70 (m, 2H), 6.80-6.90 (d, 6H), 7.00 (s, 4H), 7.20-7.25 (d, 4H); HRMS TOF [M+1]$^+$: 1783.5128.

Example 6

Synthesis of 4-(2-(2-(3,4,5-tris(isomeric decyloxy)-benzamido)-ethoxy)-ethoxy)-benzhydrylamine (DPA-006)

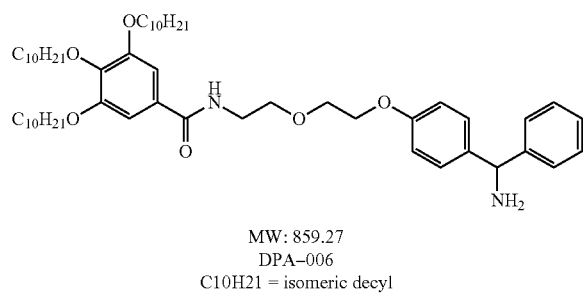

MW: 859.27
DPA–006
C10H21 = isomeric decyl

The 4-(2-(2-(3,4,5-tris(isomeric decyloxy)-benzamido)-ethoxy)-ethoxy)-benzhydrylamine (DPA-006) was synthesized according to the steps in Example 1 by using isomeric decyl bromide (prepared from Exxal 10 according to the bromination step in Example 3) instead of isooctyl bromide and using 4-hydroxybenzophenone instead of 4,4'-dihydroxybenzophenone. $^1$H-NMR (400 MHz, CDCl$_3$): δ0.80-2.00 (m, 57H), 3.65-4.15 (m, 14H), 5.20 (s, 1H), 6.55-6.65 (m, 1H), 6.80-6.90 (d, 2H), 7.00 (s, 2H), 7.20-7.40 (m, 7H); HRMS TOF [M+HCOO]$^-$: 903.6445.

Example 7

Synthesis of 4-(2-(2-(3,4,5-tris(isomeric tridecyloxy)-benzamido)-ethoxy)-ethoxy)-benzhydrylamine (DPA-007)

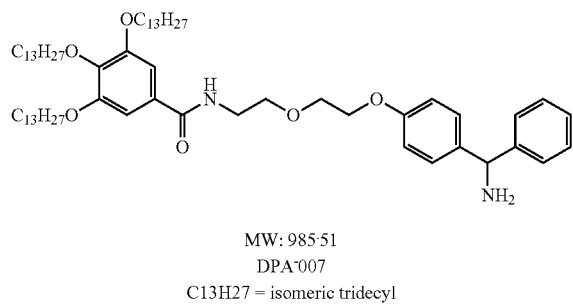

MW: 985.51
DPA-007
C13H27 = isomeric tridecyl

The 4-(2-(2-(3,4,5-tris(isomeric tridecyloxy)-benzamido)-ethoxy)-ethoxy)-benzhydrylamine (DPA-007) was synthesized according to the steps in Example 1 by using isomeric tridecyl bromide (prepared from Exxal 13 by bromination) instead of isooctyl bromide and using 4-hydroxybenzophenone instead of 4,4'-dihydroxybenzophenone. $^1$H-NMR (400 MHz, CDCl$_3$): δ0.80-2.00 (m, 75H), 3.65-4.15 (m, 14H), 5.20 (s, 1H), 6.55-6.65 (m, 1H), 6.80-6.90 (d, 2H), 7.00 (s, 2H), 7.20-7.40 (m, 7H); HRMS TOF [M+1]$^+$: 985.7959.

Example 8

Synthesis of 4-(2-(2-(N'-benzyl-3,4,5-tris(isononyloxy)-benzamido)-ethoxy)-ethoxy)-benzhydrylamine (DPA-008)

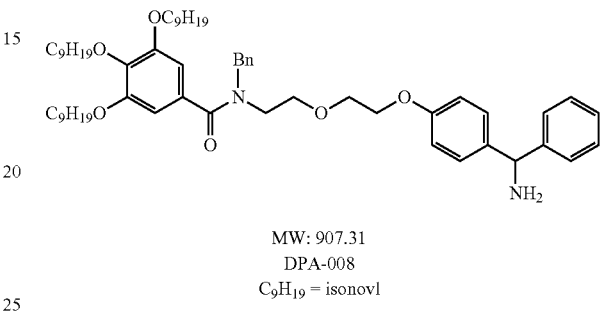

MW: 907.31
DPA-008
C9H19 = isonovl

The 4-(2-(2-(N'-benzyl-3,4,5-tris(isononyloxy)-benzamido)-ethoxy)-ethoxy)-benzhydrylamine (DPA-008) was synthesized according to the steps in Example 1 by using isononyl bromide instead of isooctyl bromide, using N-benzyl-2-(2-chloroethyl)oxy-ethylamine hydrochloride instead of 2-(2-chloroethyl)oxy-ethylamine hydrochloride and using 4-hydroxybenzophenone instead of 4,4'-dihydroxybenzophenone. $^1$H-NMR (400 MHz, CDCl$_3$): δ0.80-1.40 (m, 42H), 1.50-2.00 (m, 9H), 3.65-4.15 (m, 14H), 4.70-4.90 (m, 2H), 5.20 (s, 1H), 6.60-6.70 (bs, 2H), 6.80-6.90 (d, 2H), 7.20-7.40 (m, 14H); HRMS TOF [M+1]$^+$: 907.6531.

Preparation of N-benzyl-2-(2-chloroethyl)oxy-ethylamine hydrochloride

Diethylene glycol amine (21.0 g, 0.2 mol) was dissolved in anhydrous ethanol (100 mL), benzaldehyde (21.2 g, 0.2 mol) was added, and reacted at room temperature for half an hour; cooled to 5-10° C., sodium borohydride (11.4 g, 0.3 mol) was added, and the temperature was warmed to room temperature to react for 2 h; cooled to 5-10° C., the pH was adjusted to 1 with concentrated hydrochloric acid, and ethanol was removed under reduced pressure; water (200 mL) was added to dissolve the remainder, extracted with dichloromethane (50 mL), and the dichloromethane layer was discarded, and the pH of aqueous layer was adjusted to >14 with 10% NaOH solution; extracted with dichloromethane (100 mL*2), the dichloromethane extracts were combined and washed with water (50 mL) and saturated salt solution (50 mL), dried with anhydrous sodium sulfate, and concentrated to obtain a crude product of N-benzyl-diethanolamine (23.4 g);

The crude product of N-benzyl-diethanolamine (23.4 g, 0.12 mol) was dissolved in dichloromethane (150 mL), cooled to 0-5° C., and thionyl chloride (42.8 g, 0.36 mol) was added dropwise; after the addition was completed, the reaction was heated and refluxed for 3 hours, and the dichloromethane and unreacted thionyl chloride were removed under reduced pressure; the remainder was added with toluene (200 mL) to make a slurry, filtered and dried to obtain N-benzyl-2-(2-chloroethyl)oxy-ethylamine hydrochloride (25.0 g).

Example 9

Synthesis of 4,4'-di((5-(3,4,5-tris(isononyloxy)-benzamido)-2-one-3-aza-hexyl)oxy)-benzhydrylamine (DPA-009)

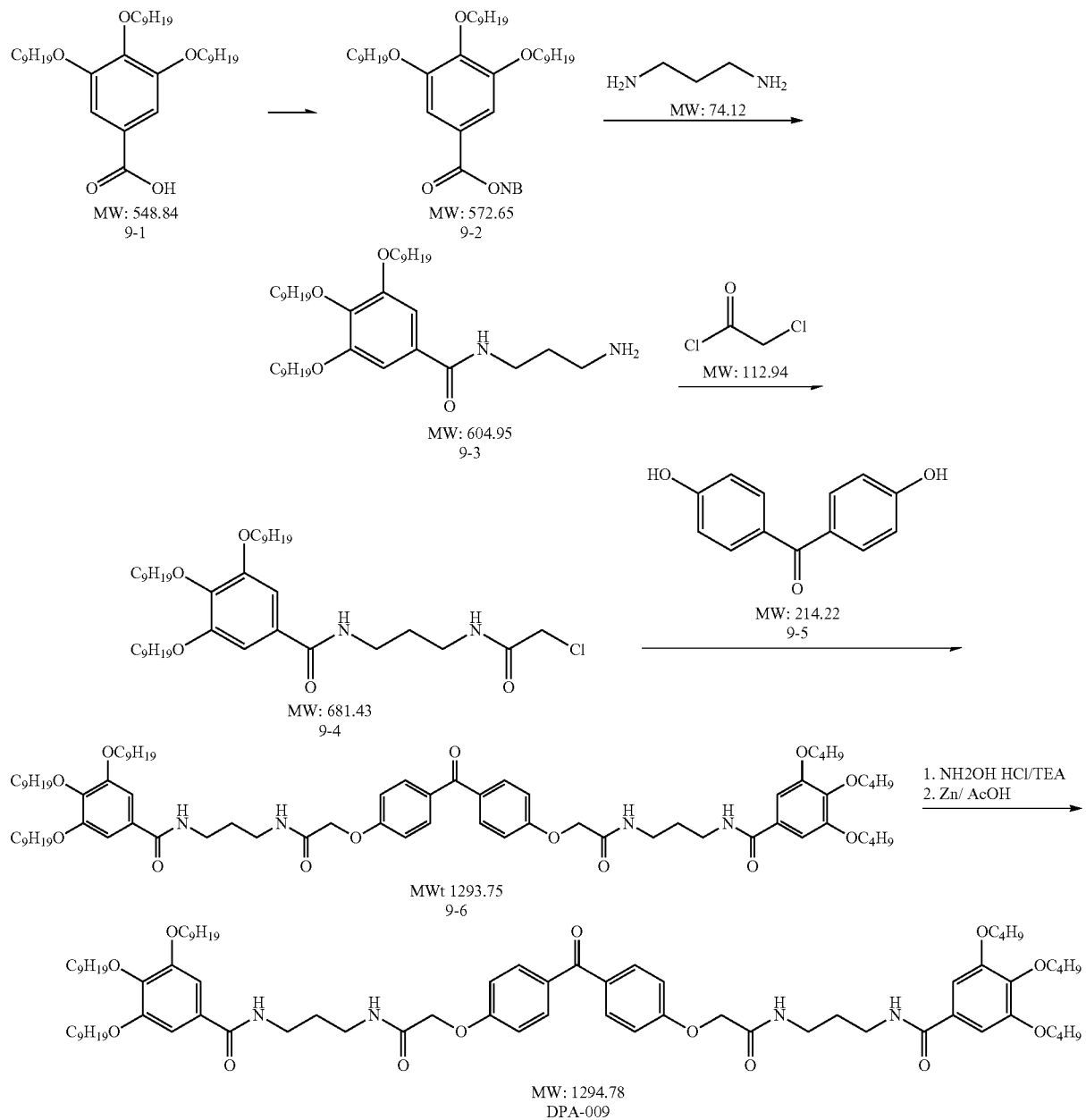

The above acid (9-1) (27.4 g, 0.05 mol) and HONB (10.8 g, 0.06 mol) were dissolved in DCM (150 mL), and EDCI (11.5 g, 0.06 mol) was added to react at room temperature for 1 h. The reaction solution was washed with water (100 mL), saturated sodium bicarbonate aqueous solution (100 mL), 1N hydrochloric acid (100 mL) and saturated salt solution sequentially. The dichloromethane solution was directly used in the next reaction.

1,3-propanediamine (11.1 g, 0.15 mol) was dissolved in DCM (20 mL), and the dichloromethane solution obtained in the previous step was added dropwise at room temperature. After the addition was completed, reacted for half an hour at room temperature, washed with water (100 mL*2), and the dichloromethane solution was directly used in the next reaction.

The dichloromethane solution obtained in the previous step was cooled to 0-5° C., and triethylamine (10 g, 0.1 mol) was added thereto; the temperature was kept at 0-5° C., and 2-chloroacetyl chloride (5.6 g, 0.05 mol) was added dropwise; after the addition was completed, the temperature was kept at 0-5° C. for 0.5 h, and washed with 1N hydrochloric acid (100 mL), water (100 mL) and saturated salt solution (50 mL) sequentially, and concentrated to obtain a crude product of intermediate 9-4.

The 9-4 crude product, 4,4'-dihydroxybenzophenone (4.9 g, 0.023 mol), potassium carbonate (9.7 g, 0.07 mol) and DMF (100 mL) were mixed in a 500 mL three-necked flask under mechanical stirring, and heated to 60-70° C. to react for 3 h. Cooled to room temperature and poured into a mixed liquid of petroleum ether (150 mL) and water (150 mL) under stirring. The lower layer was separated, the upper layer was washed with water (200 mL*2), and concentrated to obtain a crude product of intermediate 9-6.

The above crude product was dissolved in tetrahydrofuran (50 mL) and ethanol (50 mL), hydroxylamine hydrochloride (2.7 g, 0.046 mol) and triethylamine (4.6 g, 0.046 mol) were added at room temperature, and were heated to 75-80° C. to react for 12 h after mixed well. Cooled to room temperature, poured into a mixed liquid of petroleum ether (100 mL) and water (150 mL) under stirring. The lower layer was separated, the upper layer was washed with water (200 mL*2), and concentrated to obtain a ketoxime crude product. The above ketoxime crude product was dissolved in tetrahydrofuran (60 mL), acetic acid (30 mL) was added and heated to 55-60° C., and zinc powder (4.5 g, 0.069 mol) were added in batches. After the addition was completed, the reaction was continued for 2 h, the excess zinc powder was removed by filtration, and the tetrahydrofuran and acetic acid were removed by concentration. Petroleum ether (100 mL) was added to re-dissolved, washed with 10% NaOHaq (100 mL*2) and saturated salt solution sequentially, and concentrated to obtain a crude product. Purified by column chromatography (100% PE→100EA) to obtain 15.0 g of 4,4'-di ((5-(3,4,5-tris(isononyloxy)-benzamido)-2-one-3-aza-hexyl)oxy)-benzhydrylamine (DPA-009). $^1$H-NMR (400 MHz, CDCl$_3$): δ0.80-1.40 (m, 84H), 1.50-2.00 (m, 22H), 3.40-3.50 (m, 8H), 4.00-4.10 (m, 12H), 4.50 (s, 4H), 5.20 (s, 1H), 6.80-6.90 (d, 4H), 7.00-7.10 (m, 2H), 7.10 (s, 4H), 7.10-7.20 (m, 1H), 7.20-7.25 (d, 4H); HRMS TOF [M+1]$^+$: 1505.1276.

Example 10

Synthesis of 4-(2-(2-((2-(3,4,5-tris(isononyloxy)-benzamido)-propionamido)-ethoxy)-ethoxy)-benzhydrylamine (DPA-010)

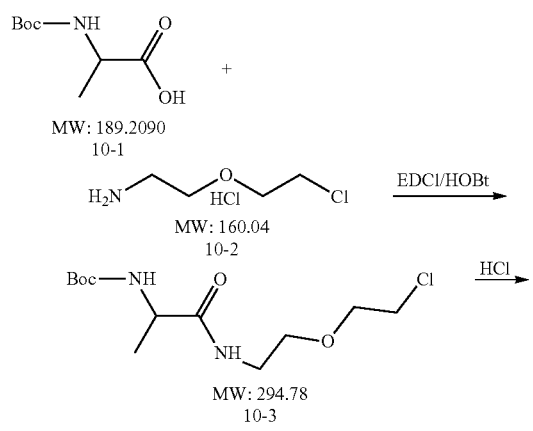

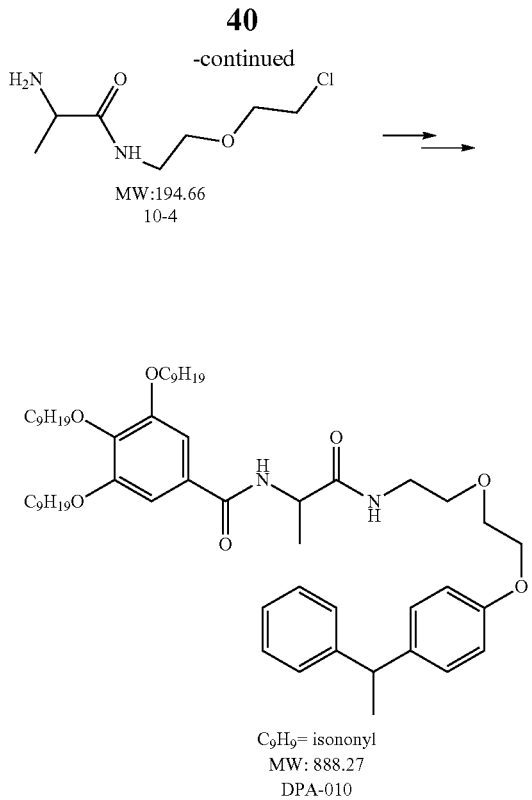

The 10-4 was synthesized according to the above route and was used instead of 2-(2-chloroethyl)oxy-ethylamine hydrochloride. Boc-Ala-OH (18.9 g, 0.1 mol), 2-(2-chloroethyl)oxy-ethylamine hydrochloride (16.0 g, 0.1 mol), HOBt (14.9 g, 0.11 mol) and triethylamine (15.1 g, 0.15 mol) were mixed in DMF (150 mL) and cooled to 5-10° C.; EDCI (21.1 g, 0.11 mol) was added and the temperature was kept at 5-10° C. to react for 0.5 h, then naturally raised to room temperature and react for 1 h; washed with water (100 mL), saturated sodium bicarbonate (100 mL), 1N hydrochloric acid (100 mL) and saturated salt solution (50 mL) sequentially; and concentrated to obtain a crude product of intermediate 10-3.

The above crude product was dissolved with ether (200 mL), and 4N HCl/ether solution (200 mL) was added dropwise, stirred at room temperature for 5 h, and filtered and collected the solid as intermediate 10-4.

The 4-(2-(2-((2-(3,4,5-tris(isononyloxy)-benzamido)-propionamido)-ethoxy)-ethoxy)-benzhydrylamine (DPA-010) was synthesized according to the steps in Example 1 by using isononyl bromide instead of isooctyl bromide, using intermediate 10-4 instead of 2-(2-chloroethyl)oxy-ethylamine hydrochloride, and using 4-hydroxybenzophenone instead of 4,4'-dihydroxybenzophenone. $^1$H-NMR (400 MHz, CDCl$_3$): δ0.80-1.40 (m, 42H), 1.40-1.50 (d, 3H), 1.50-2.00 (m, 9H), 3.45-4.15 (m, 14), 4.60-4.70 (m, 1H), 5.20 (s, 1H), 6.55-6.65 (m, 1H), 6.80-6.90 (d, 2H), 6.90-7.00 (m, 1H), 7.00 (s, 2H), 7.20-7.40 (m, 7H); HRMS TOF [M+1]$^+$: 888.6460.

Example 11
Synthesis of 4-(2-(2-(3,4,5-tris(isononyloxy)-benzamido)-ethoxy)-ethoxy)-4'-chloro-benzhydrylamine (DPA-011)
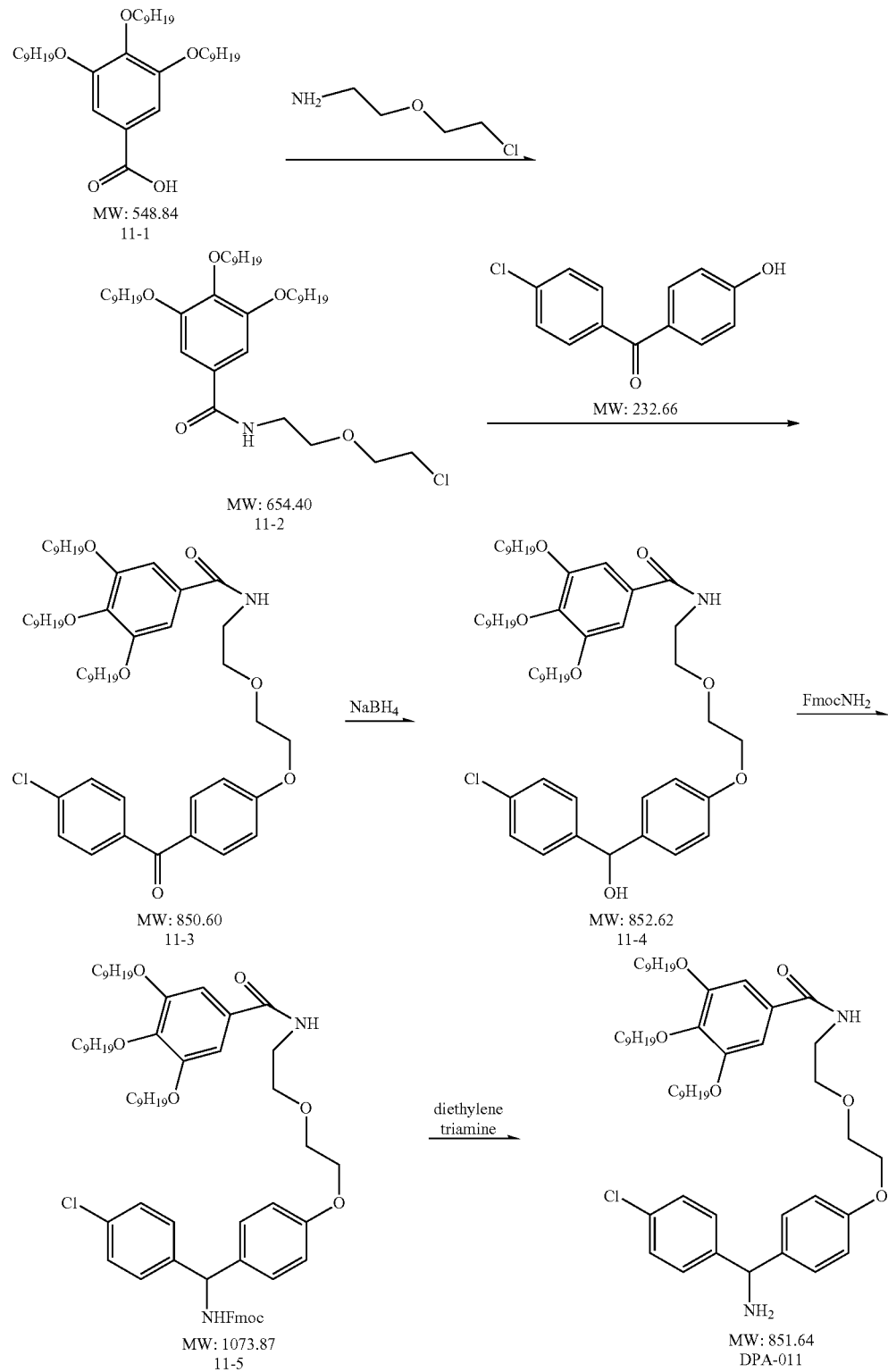

Ketone 11-1 (8.5 g, 0.01 mol) synthesized according to Example 7 by using 4-hydroxy-4'-chloro-benzophenone instead of 4-hydroxybenzophenone was dissolved in 50 mL ethanol, sodium borohydride (0.37 g, 0.1 mol) was added thereto, and reacted at room temperature for half an hour; petroleum ether (100 mL) and water (100 mL) were added, extracted, washed with 1N hydrochloric acid and saturated salt solution, and concentrated to obtain a crude product 11-2.

The crude product 11-2 obtained above was dissolved in toluene (100 mL), FmocNH$_2$ (2.63 g, 0.11 mol) and methanesulfonic acid (0.5 g, 0.005 mol) were added, heating reflux and separating water to react for 3 h; cooled to room temperature, and washed with water (100 mL) and saturated salt solution; the toluene solution was returned to the reaction flask, and heated to 40-45° C.; a mixed solution of mercaptopropionic acid (4.0 g, 0.04 mol), diethylene triamine (6.1 g, 0.06 mol) and DMF (20 mL) were added, the temperature was kept at 40-45° C. to react for half an hour; water (10 mL) was added, and after stirring evenly, the lower layer was separated; the upper layer was washed with water (20 mL*2), and concentrated to obtain a crude product; purified by column chromatography to obtain 7.6 g of 4-(2-(2-(3,4,5-tris(isononyloxy)-benzamido)-ethoxy)-ethoxy)-4'-chloro-benzhydrylamine (DPA-011). $^1$H-NMR (400 MHz, CDCl$_3$): δ0.80-1.40 (m, 42H), 1.50-2.00 (m, 9H), 3.60-4.20 (m, 14H), 5.20 (s, 1H), 6.60-6.70 (m, 1H), 6.80-6.90 (d, 2H), 6.99 (s, 2H), 7.15-7.25 (d, 2H), 7.25-7.35 (m, 4H); HRMS TOF [M+1]$^+$: 851.5699.

Example 12

Synthesis of 4-(2-(2-((2,6-di(3,4,5-tris(isononyloxy)-benzamido)-hexanamido-ethoxy)-ethoxy)-benzhydrylamine (DPA-012)

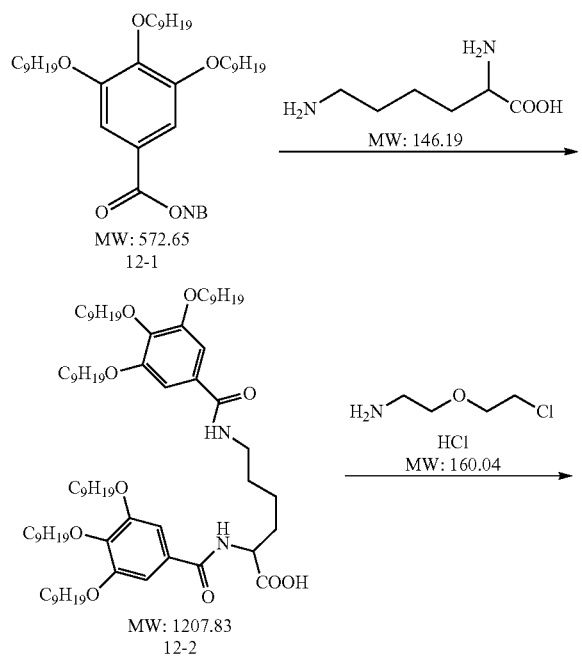

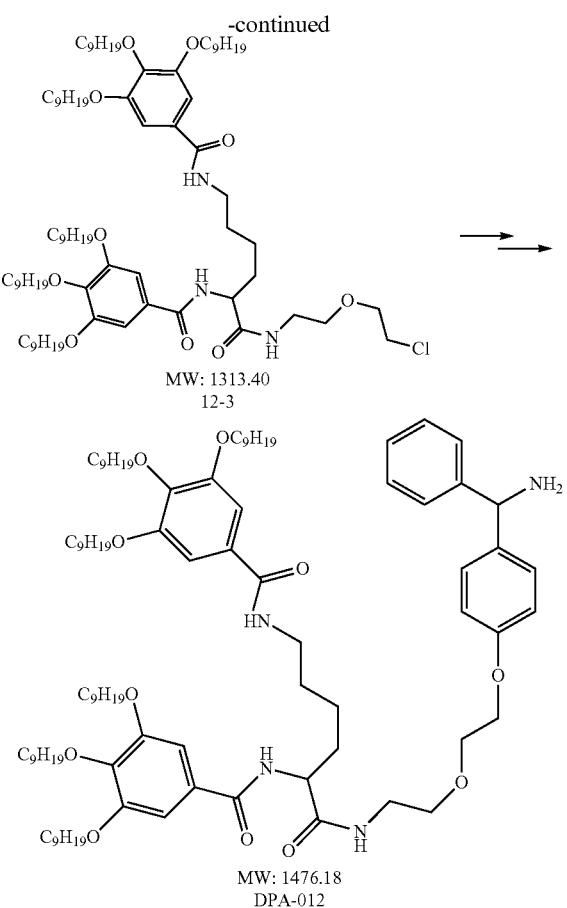

An active ester was synthesized according to the steps in Example 9, and then a branched chloride was synthesized according to the following route, and then a target carrier was synthesized according to the steps in Example 11 by reacting with 4-hydroxy-benzophenone.

Lysine (7.3 g, 0.05 mol) was dissolved in tetrahydrofuran (100 mL) and water (50 mL), LiOH (1.2 g, 0.05 mol) was added, and heated to 70° C.; active ester 12-1 (62.9 g, 0.11 mol) was dissolved in tetrahydrofuran (150 mL) and was slowly added dropwise to the reaction solution; after the addition was completed, the temperature was kept to react for half an hour; cooled to room temperature, 50 mL of 1N hydrochloric acid was added, and extracted with petroleum ether (200 mL); the upper layer was washed with water (100 mL) and saturated salt solution (100 mL) sequentially, and concentrated to obtain a crude product of intermediate 12-2.

The above crude product was dissolved in dichloromethane (300 mL) and cooled to 0-5° C.; triethylamine (5.5 g, 0.06 mol), HOBt (8.5 g, 0.06 mol) and EDCI (11.5 g, 0.06 mol) were added, the temperature was kept at 0-5° C. to react for half an hour; washed with water (200 mL), saturated sodium bicarbonate aqueous solution (100 mL×2), 1N hydrochloric acid (50 mL) and saturated (50 mL) salt solution (50 mL) sequentially, concentrated, and purified by column chromatography to obtain 49.0 g of intermediate 12-3.

The 4-(2-(2-((2,6-di(3,4,5-tris(isononyloxy)-benzamido)-hexanamido-ethoxy)-ethoxy)-benzhydrylamine (DPA-012) was prepared according to the steps in Example 11 by reacting the above intermediate with 4-hydroxy-benzophenone. 1H-NMR (400 MHz, CDCl$_3$): δ0.80-1.40 (m, 84H) 1.50-2.00 (m, 22H), 3.65-4.15 (m, 22), 4.50-4.60 (m, 1H), 5.10-5.20 (s, 1H), 6.25-6.35 (m, 1H), 6.40-6.50 (m, 1H), 6.80-6.90 (m, 3H), 6.95-7.05 (m, 5H), 7.20-7.40 (d, 6H); HRMS TOF [M+1]$^+$: 1476.1340.

Example 13

Synthesis of 4-(2-(2-(3,4-di(isomeric tridecyloxy)-phenylacetamido)-ethoxy)-ethoxy)-benzhydrylamine (DPA-013)

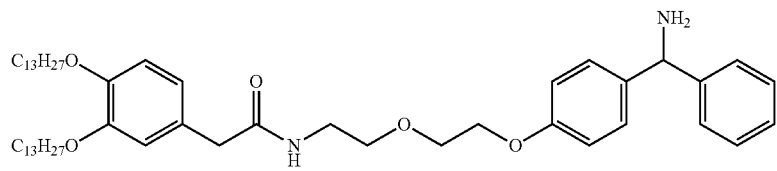

MW: 801.19
DPA-013
C13H27 = isomeric tridecyl

The 4-(2-(2-(3,4-di(isomeric tridecyloxy)-phenylacetamido)-ethoxy)-ethoxy)-benzhydrylamine (DPA-013) was prepared according to the steps in Example 9 by using methyl 3,4-dihydroxyphenylacetate instead of methyl 3,4,5-trihydroxybenzoate. $^1$H-NMR (400 MHz, CDCl$_3$): δ0.70-1.90 (m, 50H), 3.40-4.10 (m, 14H), 5.20 (s, 1H), 5.85-5.95 (m, 1H), 6.70-6.90 (m, 5H), 7.20-7.40 (m, 7H); HRMS TOF [M+1]$^+$: 801.6140.

Example 14

Synthesis of 4-(2-(2-(2,6-diisostearamido-hexanamido)-ethoxy)-ethoxy)-benzhydrylamine (DPA-014)

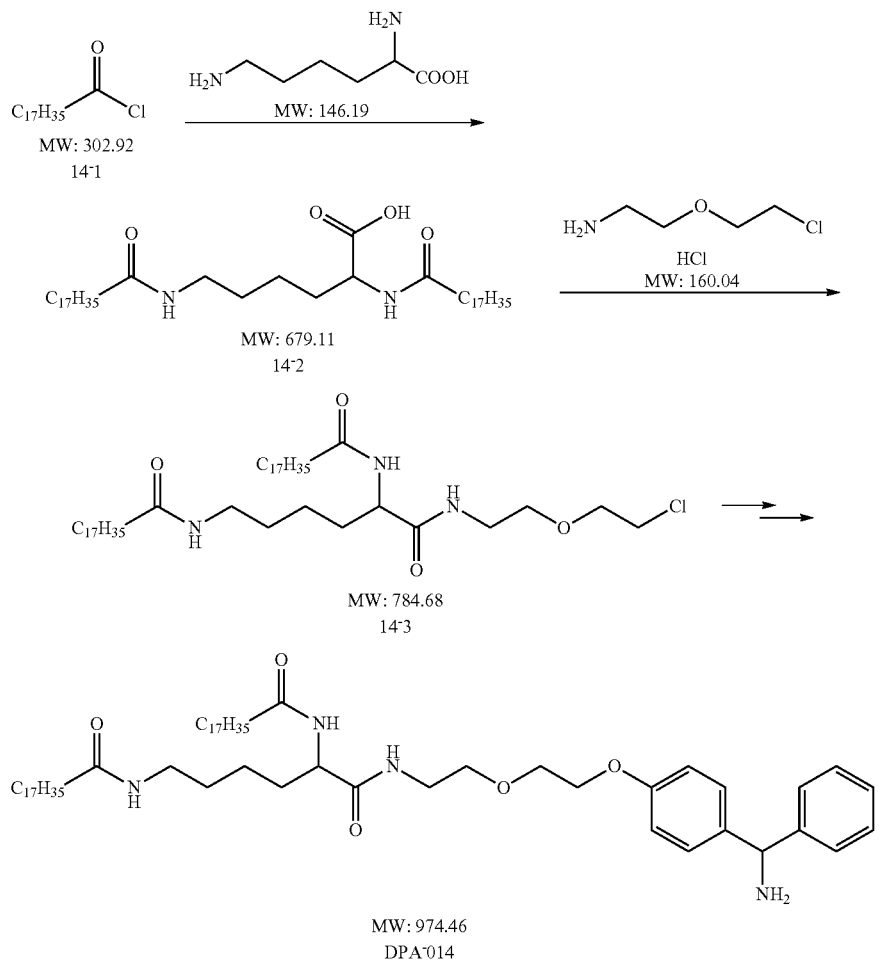

C17H15= 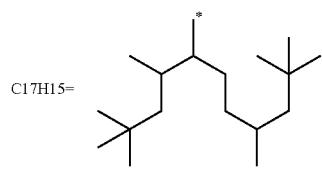

Lysine (14.6.3 g, 0.1 mol) was dissolved in tetrahydrofuran (150 mL) and water (100 mL), NaOH (4.0 g, 0.1 mol) was added, and cooled to 0-5° C., isostearoyl chloride (2,2,4,8,10,10-hexamethylundecane-5-acyl chloride) (66.6 g, 0.22 mol) and 20% NaOH (44 g) were simultaneously added dropwise to the reaction solution under vigorous stirring; the dropping speed was controlled to maintain the reaction temperature at 0-5° C., after the dripping was completed, the temperature was kept at 0-5° C. to react for half an hour; the pH was adjusted to 1 with 1N hydrochloric acid, and extracted with petroleum ether (300 mL); the petroleum ether solution was washed with water (100 mL) and saturated salt solution (100 mL) sequentially; concentrated, and purified by column chromatography to obtain 50.5 g of intermediate 14-2.

The 4-(2-(2-(2,6-diisostearamido-hexanamido)-ethoxy)-ethoxy)-benzhydrylamine (DPA-014) was synthesized according to the steps of carrier synthesis in Example 12 by using intermediate 14-2. $^1$H-NMR (400 MHz, CDCl$_3$): δ0.80-1.50 (m, 68H), 1.50-2.40 (m, 8H), 3.20-4.20 (m, 10H), 4.30-4.40 (m, 1H), 5.20 (s, 1H), 6.10-6.20 (m, 1H), 6.60-6.70 (bs, 1H), 6.80-6.90 (d, 2H), 6.90-7.00 (m, 1H), 7.20-7.40 (m, 7H); HRMS TOF [M+1]$^+$: 947.6181.

Example 15

Synthesis of 4-(2-(2-(4-(3,4,5-tri(isomeric tridecyloxy)-benzamido)-butyrylamido)-ethoxy)-ethoxy)-benzhydrylamine (DPA-015)

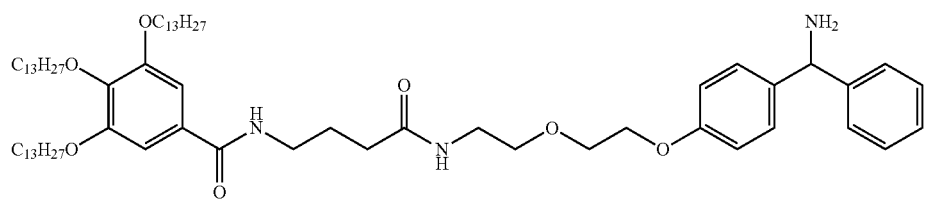

MW: 1070·61
DPA-015
$C_{13}H_{27}$ = isomeric tridecyl

The 4-(2-(2-(4-(3,4,5-tri(isomeric tridecyloxy)-benzamido)-butyrylamido)-ethoxy)-ethoxy)-benzhydrylamine (DPA-015) was prepared according to the methods in Example 14 by using γ-aminobutyric acid instead of lysine. $^1$H-NMR (400 MHz, CDCl$_3$): δ0.80-2.00 (m, 77H), 2.25-2.35 (m, 2H), 3.40-3.50 (m, 4H), 3.55-4.10 (m, 12H), 5.20 (s, 1H), 6.15-6.20 (m, 1H), 6.80-6.90 (d, 2H), 7.10 (s, 2H), 7.20-7.40 (m, 8H); HRMS TOF [M+1]$^+$: 1070.6617.

Example 16

Synthesis of 3,4-di(2-(2-(4-(3,4,5-tri(isononyloxy)-benzamido)-ethoxy)-ethoxy)-benzhydrylamine (DPA-016)

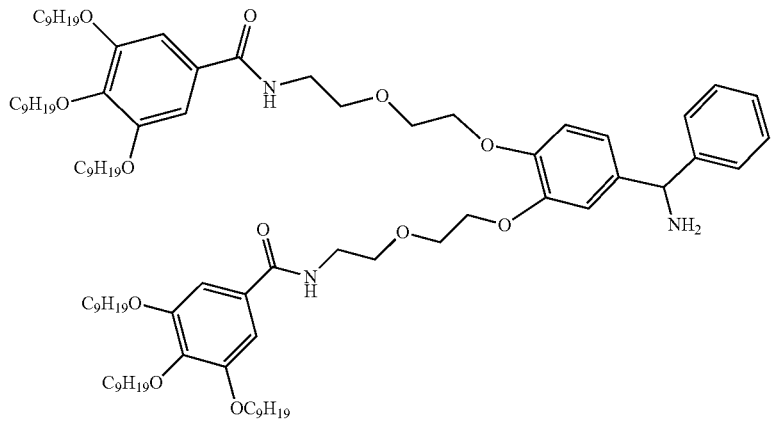

MW: 1451·13
DAP-016
C₉H₁₉ = isononyl

The 3,4-di(2-(2-(4-(3,4,5-tri(isononyloxy)-benzamido)-ethoxy)-ethoxy)-benzhydrylamine (DPA-016) was synthesized according to the methods in Example 2 by using 3,4-dihydroxy-benzophenone instead of 4,4'-dihydroxy-benzophenone. $^1$H-NMR (400 MHz, CDCl$_3$): δ0.80-1.40 (m, 84H), 1.50-2.00 (m, 18H), 3.65-4.15 (m, 28H), 5.10-5.20 (s, 1H), 6.70-7.40 (m, 12H); HRMS TOF [M+1]$^+$: 1451.1058.

Example 17

Synthesis of 4-(2-(2-((2,6-di(3,4,5-tri(isomeric tridecyloxy)-benzamido)-hexanamido)-ethoxy)-ethoxy)-benzhydrylamine (DPA-017)

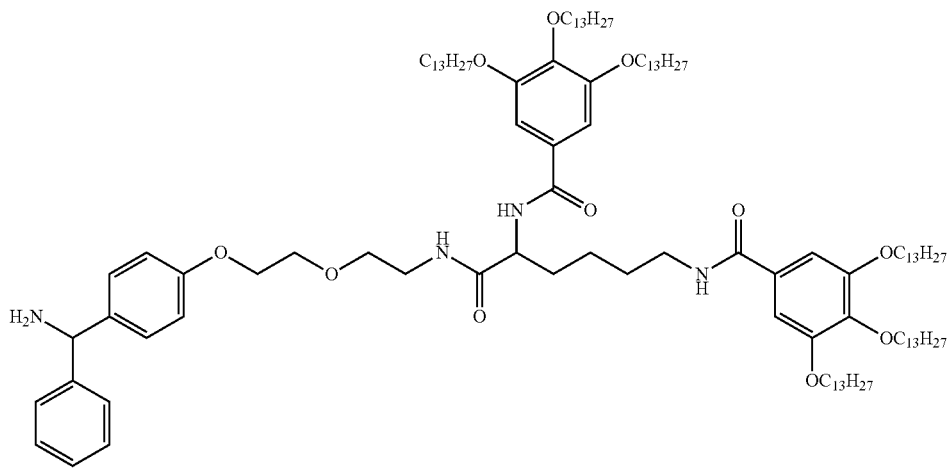

MW: 1812·82
DPA-017
C13H27 = isomeric tridecyl

The 4-(2-(2-((2,6-di(3,4,5-tri(isomeric tridecyloxy)-benzamido)-hexanamido)-ethoxy)-ethoxy)-benzhydrylamine (DPA-017) was synthesized according to the steps in Example 12. ¹H-NMR (400 MHz, CDCl₃): δ0.70-1.90 (m, 154H), 3.65-4.15 (m, 22H), 4.50-4.60 (m, 1H), 5.10-5.20 (s, 1H), 6.25-6.35 (m, 1H), 6.40-6.50 (m, 1H), 6.80-6.90 (m, 3H), 6.95-7.05 (m, 5H), 7.20-740 (d, 6H); HRMS TOF [M+1]⁺: 1812.1340.

Example 18

Synthesis of 4,4'-di(2-(2-(isostearamido)-ethoxy)-ethoxy)-benzhydrylamine (DPA-018)

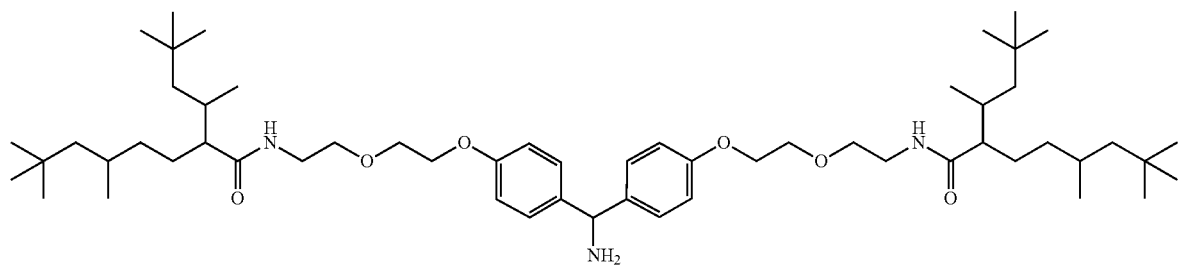

MW: 922·41
DPA-018

The 4,4'-di(2-(2-(isostearamido)-ethoxy)-ethoxy)-benzhydrylamine (DPA-018) was synthesized according to the steps in Example 1 by using isostearic acid (2,2,4,8,10,10-hexamethylundecane-5-carboxylic acid) and 2-(2-chloroethyl)oxy-ethylamine hydrochloride as raw materials. ¹H-NMR (400 MHz, CDCl₃): δ0.92-0.0.98 (m, 48H), 1.00-1.10 (m, 12H), 1.20-1.25 (m, 8H), 2.30-2.40 (m, 2H), 3.60-4.20 (m, 16H), 5.10-5.20 (s, 1H), 6.65-6.70 (m, 2H), 6.80-6.90 (d, 4H), 7.20-7.25 (d, 4H); HRMS TOF [M+1]⁺: 922.4320.

Example 19

Synthesis of 4-(2-(2-(isostearamido)-ethoxy)-ethoxy)-benzhydrylamine (DPA-019)

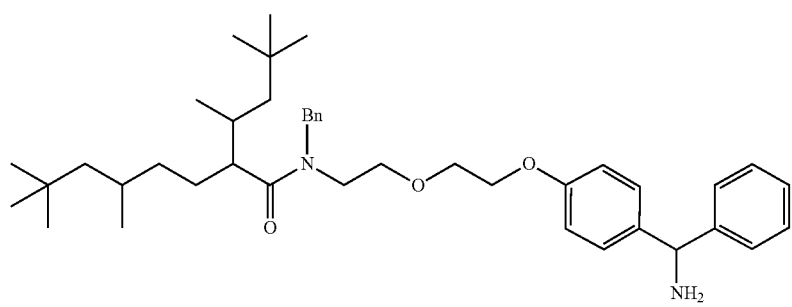

MW: 642·95
DPA-019

The 4-(2-(2-(isostearamido)-ethoxy)-ethoxy)-benzhydrylamine (DPA-019) was synthesized according to the steps in Example 7 by using isostearic acid (2,2,4,8,10,10-hexamethylundecane-5-carboxylic acid) instead of 3,4,5-tri(isomeric tridecyloxy)-benzoic acid and using N-benzyl-2-(2-chloroethyl)oxy-ethylamine hydrochloride instead of 2-(2-chloroethyl)oxy-ethylamine hydrochloride. $^1$H-NMR (400 MHz, CDCl$_3$): δ0.80-1.80 (m, 34H), 2.30-2.40 (m, 1H), 3.65-3.75 (m, 4H), 3.80-3.90 (m, 2H), 4.05-4.15 (m, 2H), 4.70-4.90 (m, 2H), 5.20 (s, 1H), 6.60-6.70 (bs, 2H), 6.80-6.90 (d, 2H), 7.20-7.40 (m, 14H); HRMS TOF [M+1]$^+$: 642.2470.

Example 20

Synthesis of 4,4'-di(2-(2-(isostearamido)-ethoxy)-ethoxy)-benzhydrylamine (DPA-020)

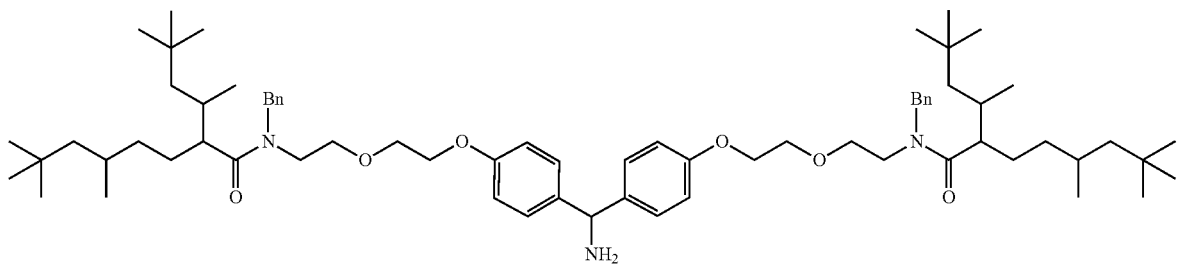

MW: 1102·66
DPA-020

The 4,4'-di(2-(2-(isostearamido)-ethoxy)-ethoxy)-benzhydrylamine (DPA-020) was synthesized according to the steps in Example 1 by using 2,2,4,8,10,10-hexamethylundecane-5-carboxylic acid instead of 3,4,5-tri(isononyloxy)-benzoic acid and using N-benzyl-2-(2-chloroethyl)oxy-ethylamine hydrochloride instead of 2-(2-chloroethyl)oxy-ethylamine hydrochloride. $^1$H-NMR (400 MHz, CDCl$_3$): δ0.80-1.80 (m, 68H), 2.30-2.40 (m, 2H), 3.65-3.75 (m, 4H), 3.80-3.90 (m, 2H), 4.05-4.15 (m, 2H), 4.70-4.90 (m, 4H), 6.80-6.90 (d, 4H), 7.20-7.40 (d, 14H); HRMS TOF [M+1]$^+$: 1102.6420.

Example 21

Synthesis of 4-(2-(N'-benzyl-(3-(N''-benzyl-3,4,5-triisononyloxy-benzamido)-propylamino)-2-one-ethoxy)-benzhydrylamine (DPA-021)

MW: 1024·46
DPA-021

C$_9$H$_{19}$ = isononyl

The 4-(2-(N'-benzyl-(3-(N''-benzyl-3,4,5-triisononyloxy-benzamido)-propylamino)-2-one-ethoxy)-benzhydrylamine (DPA-021) was synthesized according to the steps in Example 9 by using N,N'-dibenzyl propane diamine instead of propane diamine and using 4-hydroxy-benzophenone instead of 4-4'-dihydroxy benzophenone. $^1$H-NMR (400 MHz, CDCl$_3$): δ0.80-1.40 (m, 42H), 1.50-2.00 (m, 11H), 3.40-3.50 (m, 4H), 4.00-4.10 (m, 6H), 4.50 (s, 2H), 4.7-4.9 (m, 4H), 5.20 (s, 1H), 6.60-6.70 (bs, 2H), 6.80-6.90 (d, 2H), 7.20-7.40 (m, 19H). HRMS TOF [M+1]$^+$: 1024.4611.

Example 22

Synthesis of 4-(2-(2-((N"-methy-2-(3,4,5-tri(isononyloxy)-benzamido)-acetamido-ethoxy)-ethoxy)-benzhydrylamine (DPA-022)

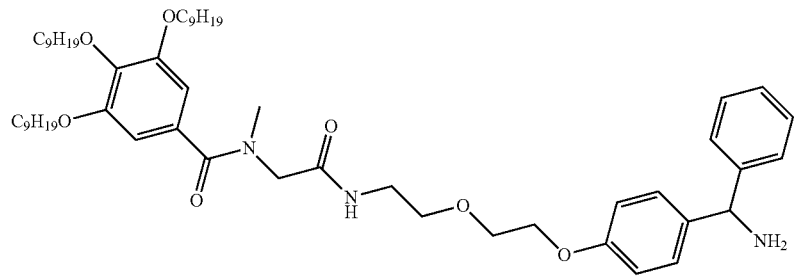

MW:888.27
DPA-022
$C_9H_{19}$ = isononyl

The 4-(2-(2-((N"-methy-2-(3,4,5-tri(isononyloxy)-benzamido)-acetamido-ethoxy)-ethoxy)-benzhydrylamine (DPA-022) was prepared according to the steps in Example 12 by using sarcosine instead of lysine. $^1$H-NMR (400 MHz, CDCl$_3$): δ0.80-1.40 (m, 42H), 1.50-2.00 (m, 9H), 2.90-3.00 (m, 3H), 3.45-4.15 (m, 14), 4.50-4.60 (s, 2H), 5.20 (s, 1H), 6.55-6.65 (m, 1H), 6.80-6.90 (d, 2H), 7.00 (s, 2H), 7.20-7.40 (m, 7H); HRMS TOF [M+1]$^+$: 888.2686.

Example 23

Synthesis of 4-(2-(2-(3,4,5-tri(n-dodecyloxy)-benzamido)-ethoxy)-ethoxy)-benzhydrylamine (DPA-023)

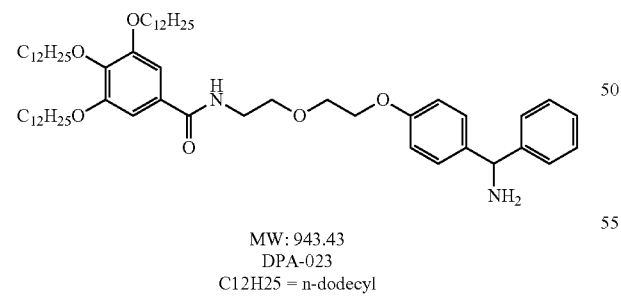

MW: 943.43
DPA-023
C12H25 = n-dodecyl

The 4-(2-(2-(3,4,5-tri(n-dodecyloxy)-benzamido)-ethoxy)-ethoxy)-benzhydrylamine (DPA-023) was synthesized according to the steps in Example 7 by using n-dodecyl bromide instead of isomeric tridecyl bromide. $^1$H-NMR (400 MHz, CDCl$_3$): δ0.80-1.00 (m, 9H), 1.00-1.40 (m, 54H), 1.50-2.00 (m, 6H), 3.65-4.15 (m, 14), 5.20 (s, 1H), 6.55-6.65 (m, 1H), 6.80-6.90 (d, 2H), 7.00 (s, 2H), 7.20-7.40 (m, 7H); HRMS TOF [M+1]$^+$: 943.7425.

Example 24

Synthesis of 4-(2-(2-(3,4,5-tri(octa/decy/dodecyloxy)-benzamido)-ethoxy)-ethoxy)-benzhydrylamine (DPA-024)

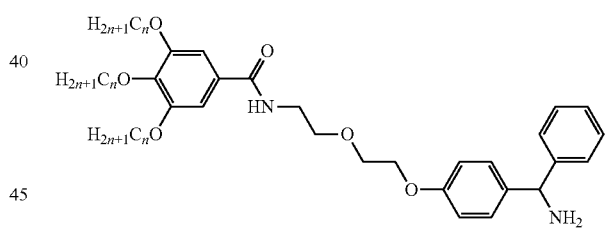

DOA-024
n = 8/10/12

The 4-(2-(2-(3,4,5-tri(octa/decy/dodecyloxy)-benzamido)-ethoxy)-ethoxy)-benzhydrylamine (DPA-024) was synthesized according to the steps in Example 1 by using a mixture of n-octyl bromide, n-decyl bromide and n-dodecyl bromide (molar ratio 1:1:1) instead of isooctyl bromide. $^1$H-NMR (400 MHz, CDCl$_3$): δ0.80-1.40 (m, 51H), 1.50-2.00 (m, 6H), 3.65-4.15 (m, 14), 5.20 (s, 1H), 6.55-6.65 (m, 1H), 6.80-6.90 (d, 2H), 7.00 (s, 2H), 7.20-7.40 (m, 7H); HRMS TOF [M+1]$^+$: 831.6264, 859.6575, 887.6894.

Example 25

Synthesis of (2-(2-(3,4,5-tri(isomeric tridecyloxy)-benzamido)-ethoxy)-ethoxy)-4-methoxy-benzylamine (DPA-025)

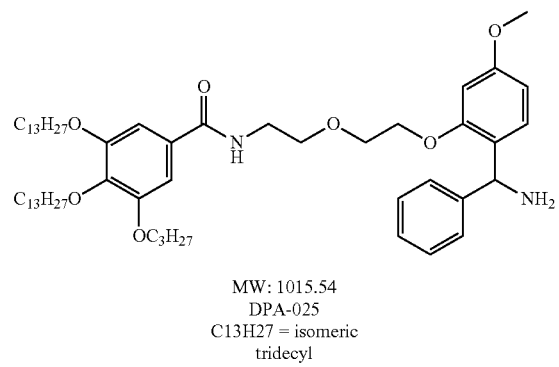

MW: 1015.54
DPA-025
C13H27 = isomeric tridecyl

The (2-(2-(3,4,5-tri(isomeric tridecyloxy)-benzamido)-ethoxy)-ethoxy)-4-methoxy-benzylamine (DPA-025) was synthesized according to the steps in Example 7 by using 2-hydroxy-4-methoxy-benzophenone instead of 4-hydroxy-benzophenone. $^1$H-NMR (400 MHz, CDCl$_3$): δ0.80-2.00 (m, 75H), 3.65-4.15 (m, 17), 5.20 (s, 1H), 6.40-6.45 (m, 2H), 7.00 (s, 2H), 6.55-6.65 (m, 1H), 7.05-7.10 (m, 1H), 7.20-7.40 (m, 5H); HRMS TOF [M+1]$^+$: 1015.4426.

Example 26

Synthesis of 4-(2-(N'-methy-3,4,5-tri(isomeric tridecyloxy)-benzamido)-ethoxy)-benzhydrylamine (DPA-026)

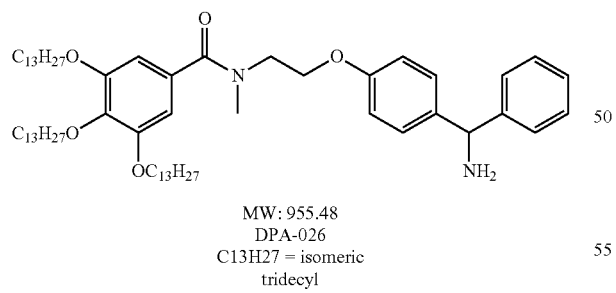

MW: 955.48
DPA-026
C13H27 = isomeric tridecyl

The 4-(2-(N'-methy-3,4,5-tri(isomeric tridecyloxy)-benzamido)-ethoxy)-benzhydrylamine (DPA-026) was synthesized according to the steps in Example 9 by using N-methyl-2-chloroethylamine hydrochloride instead of 2-(2-chloroethyl)oxy-ethylamine hydrochloride. $^1$H-NMR (400 MHz, CDCl$_3$): δ0.70-1.90 (m, 75H), 2.90-3.05 (m, 3H), 3.65-4.15 (m, 10), 5.20 (s, 1H), 6.55-6.65 (m, 1H), 6.80-6.90 (d, 2H), 7.00-7.10 (m, 2H), 7.20-7.40 (m, 7H); HRMS TOF [M+1]$^+$: 955.7852.

Example 27

Synthesis of 4-(2-(2-(N'-(3,4-di(isomeric tridecyloxy)-benzyl)-acetamido)-ethoxy)-ethoxy-benzhydrylamine (DPA-027)

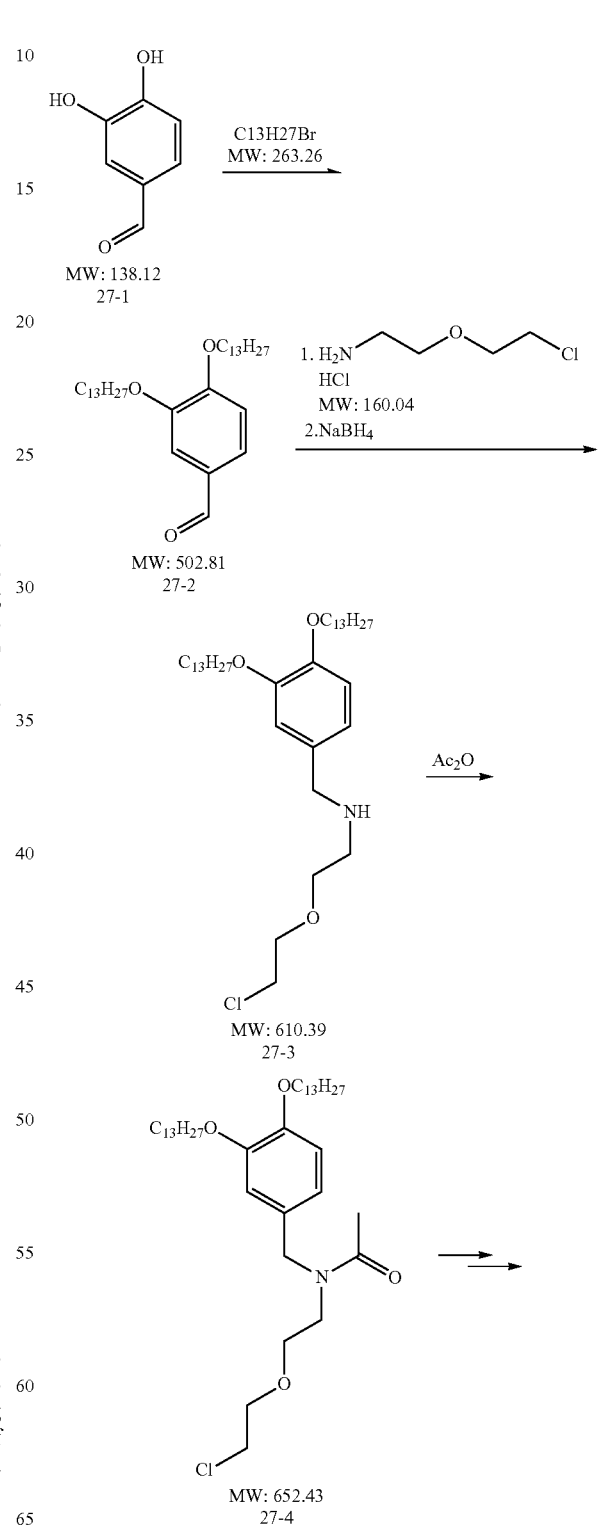

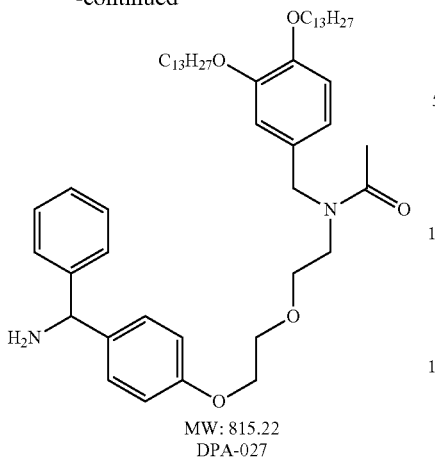

MW: 815.22
DPA-027

3,4-dihydroxy-benzaldehyde (13.8 g, 0.1 mol), isomeric tridecyl bromide (63.1 g, 0.24 mol), potassium carbonate (41.4 g, 0.3 mol) and DMF (200 mL) were mixed and heated to 90-100° C. to react for 10 h; poured into a reaction flask which was introduced with petroleum ether (200 mL) and water (200 mL) in advance under stirring, the lower layer was separated, and the upper layer was washed with water (100 mL) and saturated salt solution (100 mL); and concentrated to obtain a crude product of intermediate 27-2.

The above crude product was dissolved in tetrahydrofuran (100 mL) and ethanol (200 mL), and 2-(2-chloroethyl)oxy-ethylamine hydrochloride (16.0 g, 0.1 mol) and triethylamine (10.0 g, 0.1 mol) were added thereto, and reacted at normal temperature for 3 h; cooled to 0-5° C., sodium borohydride (3.8 g, 0.1 mol) was added, and naturally raised to room temperature to react for 2 h; 1N hydrochloric acid was added until no bubbles were generated, and the pH was 7-8; petroleum ether (300 mL) and water (300 mL) were added, and the lower layer was separated; the upper layer was washed with water (100 mL*2) and saturated salt solution and concentrated to obtain a crude product of 27-3 intermediate.

The crude product of 27-3 was dissolve in ethyl acetate (300 mL), and triethylamine (15.0 g, 0.15 mol) and acetic anhydride (10.3 g, 0.1 mol) were added; reacted at normal temperature for half an hour, added with water and stirred for 10 min; the aqueous layer was separated and the upper layer was washed with water (100 mL*2), concentrated to obtain a crude product of intermediate 27-4, which was purified by column chromatography to obtain 38.0 g.

The 4-(2-(2-(N'-(3,4-di(isomeric tridecyloxy)-benzyl)-acetamido)-ethoxy-ethoxy-benzhydrylamine (DPA-027) was synthesized according to the steps in Example 7 by using the intermediate 27-4 as a raw material. $^1$H-NMR (400 MHz, CDCl$_3$): δ0.75-1.40 (m, 46), 1.40-1.90 (m, 4H), 2.10 (s, 1.7H), 2.20 (s, 1.3H), 3.40-4.10 (m, 12H), 4.50-4.60 (m, 2H), 5.20 (s, 1H), 6.60-6.70 (m, 1H), 6.80-6.90 (d, 4H), 7.20-7.40 (m, 7H); HRMS TOF [M+1]$^+$: 815.6534.

Example 28

Synthesis of 4-(2-(2-(N'-(3,4-di(isomeric tridecyloxy)-benzyl)-isononanoamido)-ethoxy)-ethoxy-benzhydrylamine (DPA-028)

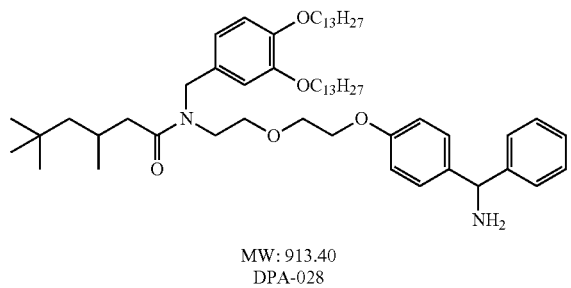

MW: 913.40
DPA-028

The 4-(2-(2-(N'-(3,4-di(isomeric tridecyloxy)-benzyl)-isononanoamido)-ethoxy)-ethoxy-benzhydrylamine (DPA-028) was synthesized according to the steps in Example 13 by using isononanoyl chloride instead of acetic anhydride. $^1$H-NMR (400 MHz, CDCl$_3$): δ0.75-1.40 (m, 60), 1.40-1.90 (m, 5H), 2.10-2.40 (m, 2H), 3.40-4.10 (m, 12H), 4.50-4.60 (m, 2H), 5.20 (s, 1H), 6.60-6.70 (m, 1H), 6.80-6.90 (d, 4H), 7.20-7.40 (m, 7H); HRMS TOF [M+1]$^+$: 913.3850.

Example 29

Synthesis of 4-(2-(2-(N'-(3,4-di(isomeric tridecyloxy)-benzyl)-3,4,5-tri(isononyloxy)-benzamido)-ethoxy)-ethoxy-benzhydrylamine (DPA-029)

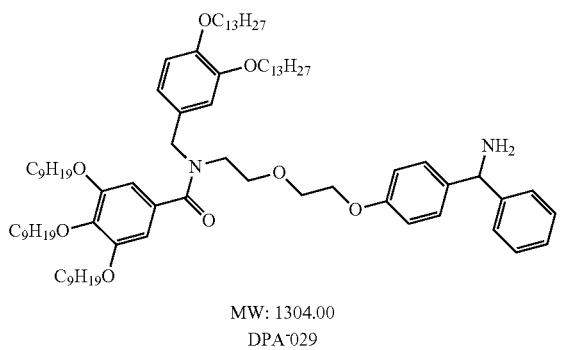

MW: 1304.00
DPA-029

The 4-(2-(2-(N'-(3,4-di(isomeric tridecyloxy)-benzyl)-3,4,5-tri(isononyloxy)-benzamido)-ethoxy)-ethoxy-benzhydrylamine (DPA-029) was synthesized by using 3,4,5-triisononyloxy benzoic acid as a raw material and using intermediate 27-4 as a raw material. $^1$H-NMR (400 MHz, CDCl$_3$): δ0.75-1.40 (m, 91), 1.40-1.90 (m, 10H), 3.40-4.10 (m, 18H), 4.50-4.80 (m, 2H), 5.20 (s, 1H), 6.60-6.70 (m, 4H), 6.80-6.90 (m, 3H), 7.20-7.40 (m, 7H); HRMS TOF [M+1]$^+$: 1304.2410.

Example 30

Synthesis of 4-(2-(2-(2-(N''-3,4-di(isomeric tridecyloxy)-benzyl)-isononanoamido)-acetamido)-ethoxy)-ethoxy-benzhydrylamine (DPA-030)

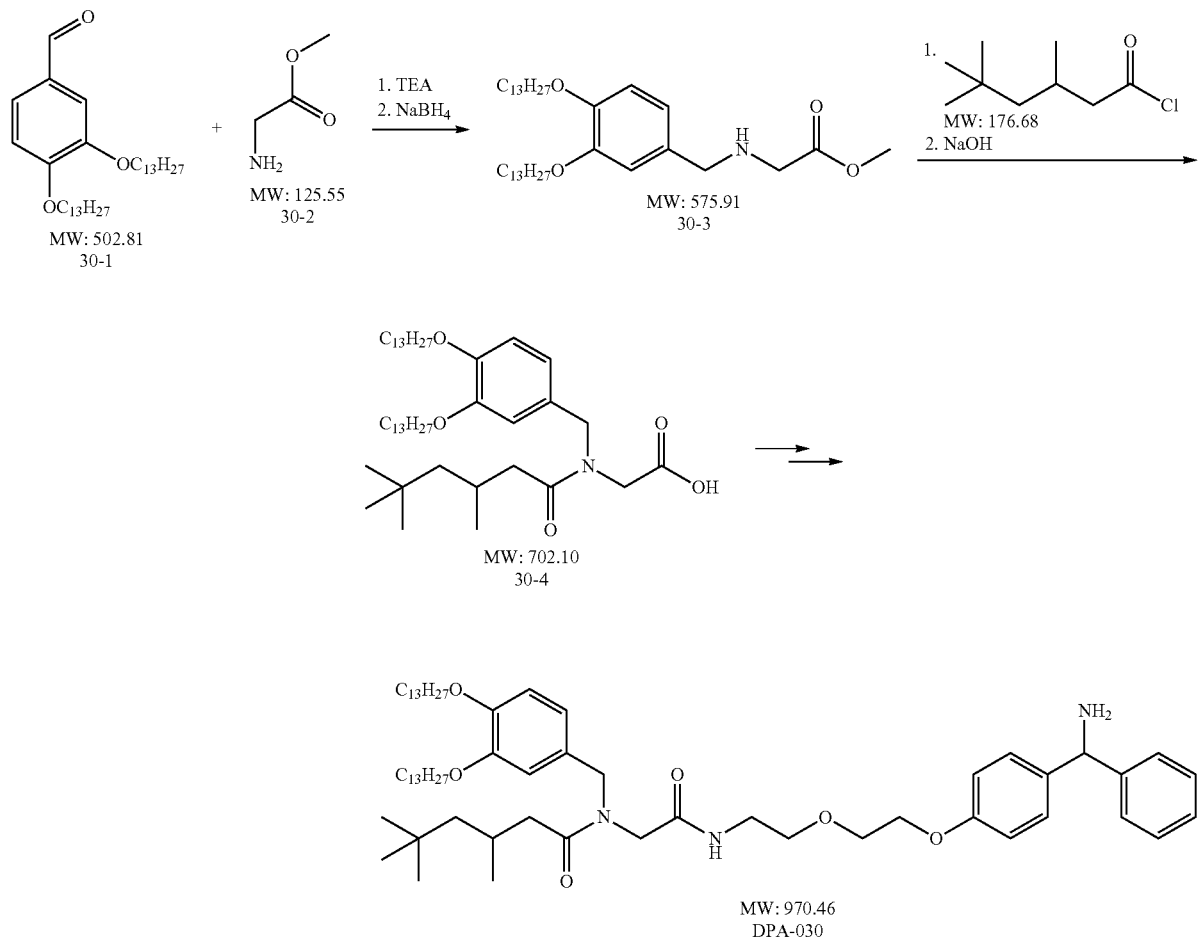

Raw material 30-1 (25.3 g, 0.05 mol), glycine methyl ester hydrochloride (12.5 g, 0.1 mol) were dissolved in anhydrous ethanol (100 mL) and tetrahydrofuran (50 mL), triethylamine (10.1 g, 0.1 mol) was added, and reacted at room temperature for 5 hours; cooled to 0-5° C. and added with sodium borohydride (3.8 g, 0.1 mol); the temperature was naturally raised to room temperature to react for 2 h; 1N hydrochloric acid was added dropwise until no bubbles were generated, and petroleum ether (200 mL) was added for extraction, the aqueous layer was separated, and the petroleum ether layer was washed with water (200 mL*2), and concentrated to obtain a crude product of intermediate 30-3.

The above crude product of intermediate 30-3 was dissolved in dichloromethane (200 mL), triethylamine (7.5 g, 0.075 mol) was added, cooled to 5-10° C. and added with isononanoyl chloride (8.8 g, 0.05 mol) dropwise; after the addition was completed, the temperature was naturally raised to room temperature to react for half an hour; washed with water (100 mL), saturated sodium bicarbonate (100 mL*2) and saturated salt solution (100 mL) sequentially and concentrated to obtain a crude product. The obtained crude product was dissolved with methanol (100 mL) and tetrahydrofuran (100 mL), LiOH (3.6 g, 0.15 mol) was added, and reacted at normal temperature for 3 h; after the hydrolysis was completed, 1N hydrochloric acid (150 mL) was added for neutralization, decompressed to remove methanol and tetrahydrofuran, and petroleum ether (200 mL) was added for extraction; the aqueous layer was separated and the petroleum ether layer was washed with water (100 mL*2) and concentrated to obtain a crude product of intermediate 30-4.

The 4-(2-(2-(2-(N''-3,4-di(isomeric tridecyloxy)-benzyl)-isononanoamido)-acetamido)-ethoxy)-ethoxy-benzhydrylamine (DPA-030) was prepared by the same synthesis steps in Example 12 by using the intermediate 30-4 as a raw material and reacted with 2-(2-chloroethyl)oxy-ethylamine hydrochloride, 4-hydroxybenzophenone and hydroxyl hydrochloride and the like sequentially. $^1$H-NMR (400 MHz, CDCl$_3$): δ0.75-1.40 (m, 60), 1.40-1.90 (m, 5H), 2.10-2.40 (m, 2H), 3.40-4.10 (m, 14H), 4.50-4.60 (m, 2H), 5.20 (s, 1H), 6.50-6.60 (m, 1H), 6.60-6.70 (m, 2H), 6.80-6.90 (d, 2H), 7.20-7.40 (m, 7H); HRMS TOF [M+1]$^+$: 970.455.

Example 31

Synthesis of 4-(2-(2-(2-(N''-3,4-di(isomeric tridecyloxy)-benzyl)-3,4,5-tri(isononyloxy)-benzamido)-acetamido)-ethoxy)-ethoxy-benzhydrylamine (DPA-031)

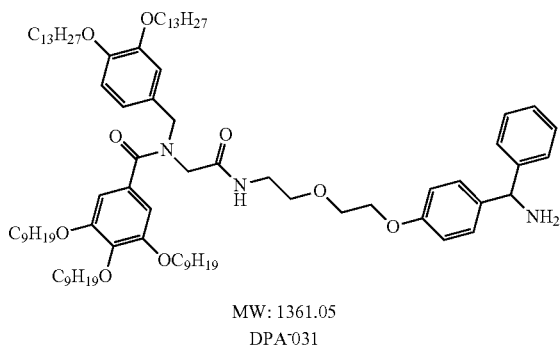

MW: 1361.05
DPA-031

After the condensation and hydrolysis of 3,4,5-triisononyloxy-benzoic acid and the intermediate 29-3 were completed, the 4-(2-(2-(2-(N''-3,4-di(isomeric tridecyloxy)-benzyl)-3,4,5-tri(isononyloxy)-benzamido)-acetamido)-ethoxy)-ethoxy-benzhydrylamine (DPA-031) was synthesized according to the steps in Example 29. $^1$H-NMR (400 MHz, CDCl$_3$): δ0.75-1.40 (m, 91), 1.40-1.90 (m, 10H), 3.40-4.10 (m, 20H), 4.50-4.80 (m, 2H), 5.20 (s, 1H), 6.60-6.70 (m, 4H), 6.80-6.90 (m, 3H), 7.20-7.40 (m, 7H); HRMS TOF [M+1]$^+$: 1361.0790.

Example 32

Synthesis of 4-(2-(2-((2,6-di(3,4,5-tri(isomeric tridecyloxy)-benzamido)-hexanamido)-ethoxy)-ethoxy)-phenyl-benzhydrol (DPA-032)

Grignard reagent (concentration 2M) was prepared from bromobenzene, and the intermediate 32-3 was prepared according to the steps in Example 3;

4-hydroxy-benzophenone (19.8 g, 0.1 mol) was dissolved in tetrahydrofuran (100 mL) in a water bath at normal temperature, and bromobenzene Grignard reagent (150 mL, 0.3 mol) was added dropwise; after the addition was completed, a reflux reaction was performed for 12 h; cooled to 0-5° C. and saturated ammonium chloride aqueous solution (100 mL) was added dropwise, tetrahydrofuran was removed under reduced pressure, and toluene (100 mL) was added for extraction; the toluene solution was washed with water (100 mL) and saturated salt solution (100 mL); concentrated to obtain a crude product (27.6 g) of intermediate 32-2 and was directly used for the next reaction;

The crude product of intermediate 32-2 (13.8 g, 0.05 mol), intermediate 32-3 (40.1 g, 0.05 mol), potassium carbonate (13.8 g, 0.1 mol), potassium iodide (1 g) and DMF (100 mL) were mixed and heated to 80-85° C. to react overnight; petroleum ether (200 mL) and water (100 mL) were added, and layered after stirring uniformly; the aqueous layer was separated and the petroleum ether layer was washed with water (100 mL), and concentrated to obtain a crude product. Purified by column chromatography (100% PE→100% EA) to obtain the 4-(2-(2-((2,6-di(3,4,5-tri(isomeric tridecyloxy)-benzamido)-hexanamido)-ethoxy)-ethoxy)-phenyl-benzhydrol (DPA-032, 22.0 g). $^1$H-NMR (400 MHz, CDCl$_3$): δ0.80-2.00 (m, 75H), 2.90 (m, 1H), 3.65-4.20 (m, 14H), 6.50-6.60 (m, 1H), 6.80-6.85 (d, 2H), 6.95-7.00 (s, 2H), 7.15-7.20 (m, 2H), 7.25-7.35 (m, 10H); HRMS TOF [M+1]$^+$: 1062.6170.

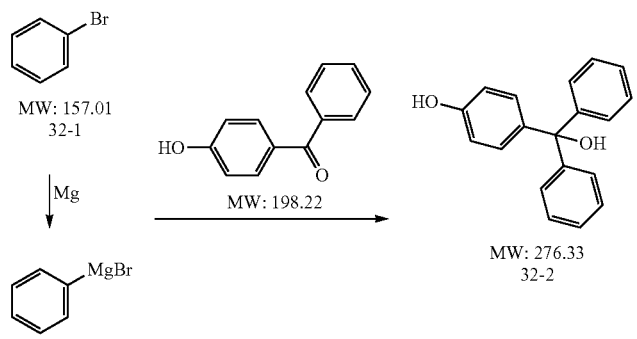

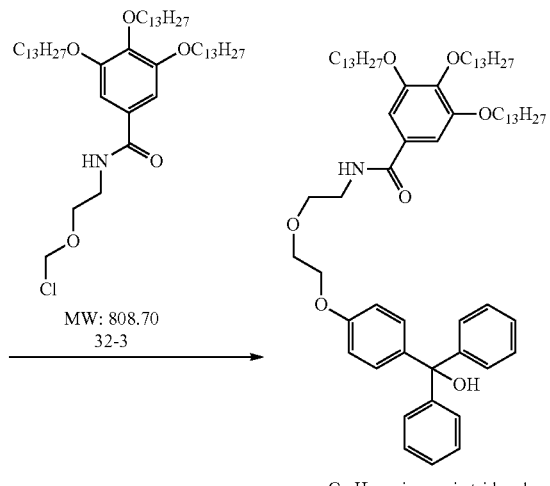

C$_{13}$H$_{27}$ = isomeric tridecyl
MW: 1062.59
DPA-032

Example 33

Synthesis of 4-(2-(2-((2,6-di(3,4,5-tri(isomeric tridecyloxy)-benzamido)-hexanamido)-ethoxy)-ethoxy)-(2-chlorophenyl)-benzhydrol (DPA-033)

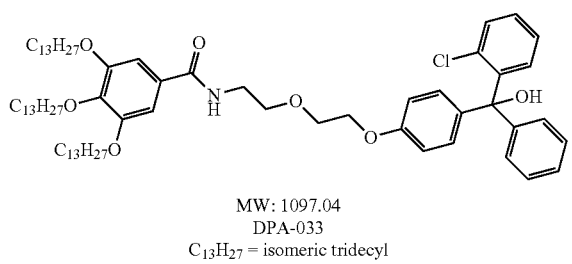

MW: 1097.04
DPA-033
$C_{13}H_{27}$ = isomeric tridecyl

The 4-(2-(2-((2,6-di(3,4,5-tri(isomeric tridecyloxy)-benzamido)-hexanamido)-ethoxy)-ethoxy)-(2-chlorophenyl)-benzhydrol (DPA-033) was synthesized according to the steps in Example 32 by using 2-chloro-4'-hydroxy-benzophenone instead of 4-hydroxy-benzophenone. $^1$H-NMR (400 MHz, CDCl$_3$): δ0.80-2.00 (m, 75H), 2.90 (m, 1H), 3.65-4.20 (m, 14H), 6.50-6.60 (m, 1H), 6.80-6.85 (d, 2H), 6.95-7.00 (s, 2H), 7.15-7.62 (m, 11H); HRMS TOF [M+1]$^+$: 1096.7244.

Example 34

Synthesis of 4-(2-(2-((2,6-di(3,4,5-tri(isomeric tridecyloxy)-benzamido)-hexanamido)-ethoxy)-ethoxy)-(4-chloro-phenyl)-4'-chloro-benzhydrol (DPA-034)

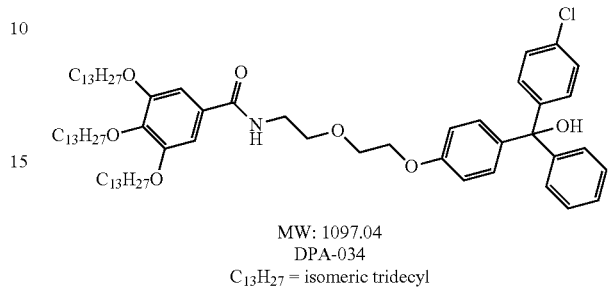

MW: 1097.04
DPA-034
$C_{13}H_{27}$ = isomeric tridecyl

The 4-(2-(2-((2,6-di(3,4,5-tri(isomeric tridecyloxy)-benzamido)-hexanamido)-ethoxy)-ethoxy)-(4-chloro-phenyl)-4'-chloro-benzhydrol (DPA-034) was synthesized according to the steps in Example 32 by using 4-chloro-4'-hydroxy-benzophenone instead of 4-hydroxy-benzophenone. $^1$H-NMR (400 MHz, CDCl$_3$): δ0.80-2.00 (m, 75H), 2.90 (m, 1H), 3.65-4.20 (m, 14H), 6.50-6.60 (m, 1H), 6.80-6.85 (d, 2H), 6.95-7.00 (s, 2H), 7.15-7.20 (m, 2H), 7.25-7.35 (m, 9H); HRMS TOF [M+1]$^+$: 1096.7244.

Example 35

Synthesis of N-benzyl-4-(2-(2-(3,4,5-tri(isomeric tridecyloxy)-benzamido)-ethoxy)-ethoxy)-benzhydrylamine (DPA-035)

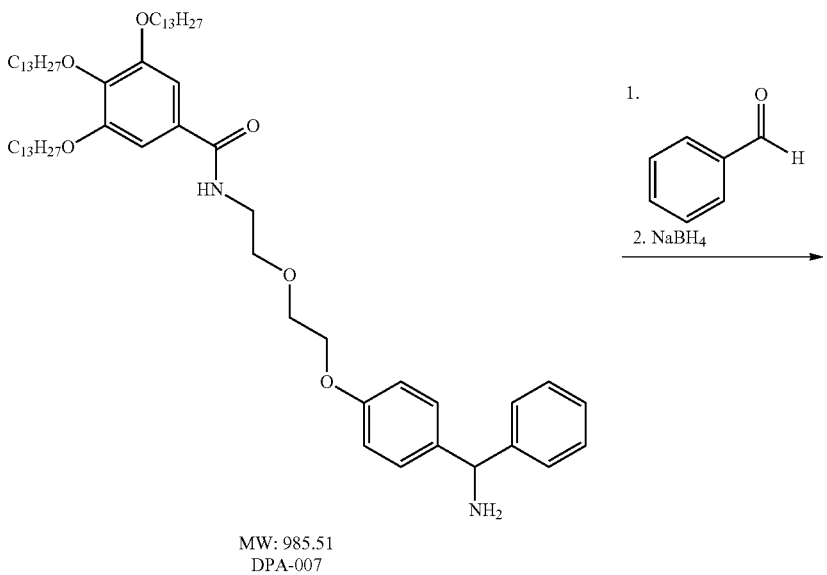

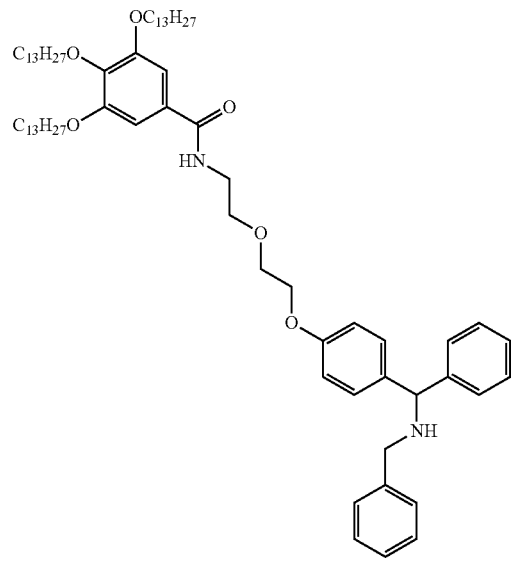

C13H27 = isometric tridecyl
MW: 1075.63
DPA-035

DPA-007 (9.85 g, 0.01 mol) and benzaldehyde (1.1 g, 0.01 mol) were dissolved in anhydrous ethanol (50 mL), acetic acid (0.1 mL) was added, and stirred and reacted for 1 hour at normal temperature; sodium borohydride (0.74 g) was added and continued to react for 1 h; 1N hydrochloric acid was added dropwise until no bubbles were generated, the pH was 7~8, and petroleum ether (100 mL) and water (200 mL) were added, stirred for 10 min, and the lower layer was separated, the upper layer of petroleum ether solution was washed with water (100 mL) and saturated salt solution (100 mL) sequentially, and concentrated to obtain a crude product, and purified by column chromatography to obtain the N-benzyl-4-(2-(2-(3,4,5-tri(isomeric tridecyloxy)-benzamido)-ethoxy)-ethoxy)-benzhydrylamine (DPA-035, 7.8 g). $^1$H-NMR (400 MHz, CDCl$_3$): δ0.80-2.00 (m, 75H), 3.65-4.15 (m, 16), 4.81 (s, 1H), 6.55-6.65 (m, 1H), 6.80-6.90 (d, 2H), 7.00 (s, 2H), 7.20-7.40 (m, 12H); HRMS TOF [M+1]$^+$: 1075.6943.

Comparative Example 1

Synthesis of 4,4'-di(dihydrophytanyloxy)-benzhydrylamine (REF-001)

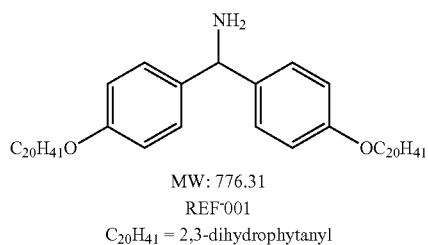

MW: 776.31
REF-001
C$_{20}$H$_{41}$ = 2,3-dihydrophytanyl

Phytol was subjected to hydrogenation and bromination, and then was reacted with 4,4'-benzophenone to obtain 4,4'-di(2,3-dihydrophytoxy)-benzophenone, and 4,4'-di(2,3dihydrophytanyloxy)-benzhydrylamine (REF-001) was synthesized according to the carrier synthesis examples. $^1$H-NMR (400 MHz, CDCl$_3$): δ0.80-1.00 (m, 30H), 1.00-1.50 (m, 40H), 1.50-1.90 (m, 8H), 3.90-4.00 (m, 4H), 5.20 (s, 1H), 6.80-6.90 (d, 4H), 7.20-7.40 (d, 4H); HRMS TOF [M+1]$^+$: 776.6238.

Comparative Example 2

Synthesis of 4-(3,4,5-tri(2,3-dihydrophytanyloxy)-benzyloxy-benzhydrylamine (REF-002) and 4-(3,4,5-tri(2,3-dihydrophytanyltoxy)-benzyloxy-(2-chlorophenyl)-benzhydrol (REF-002A)

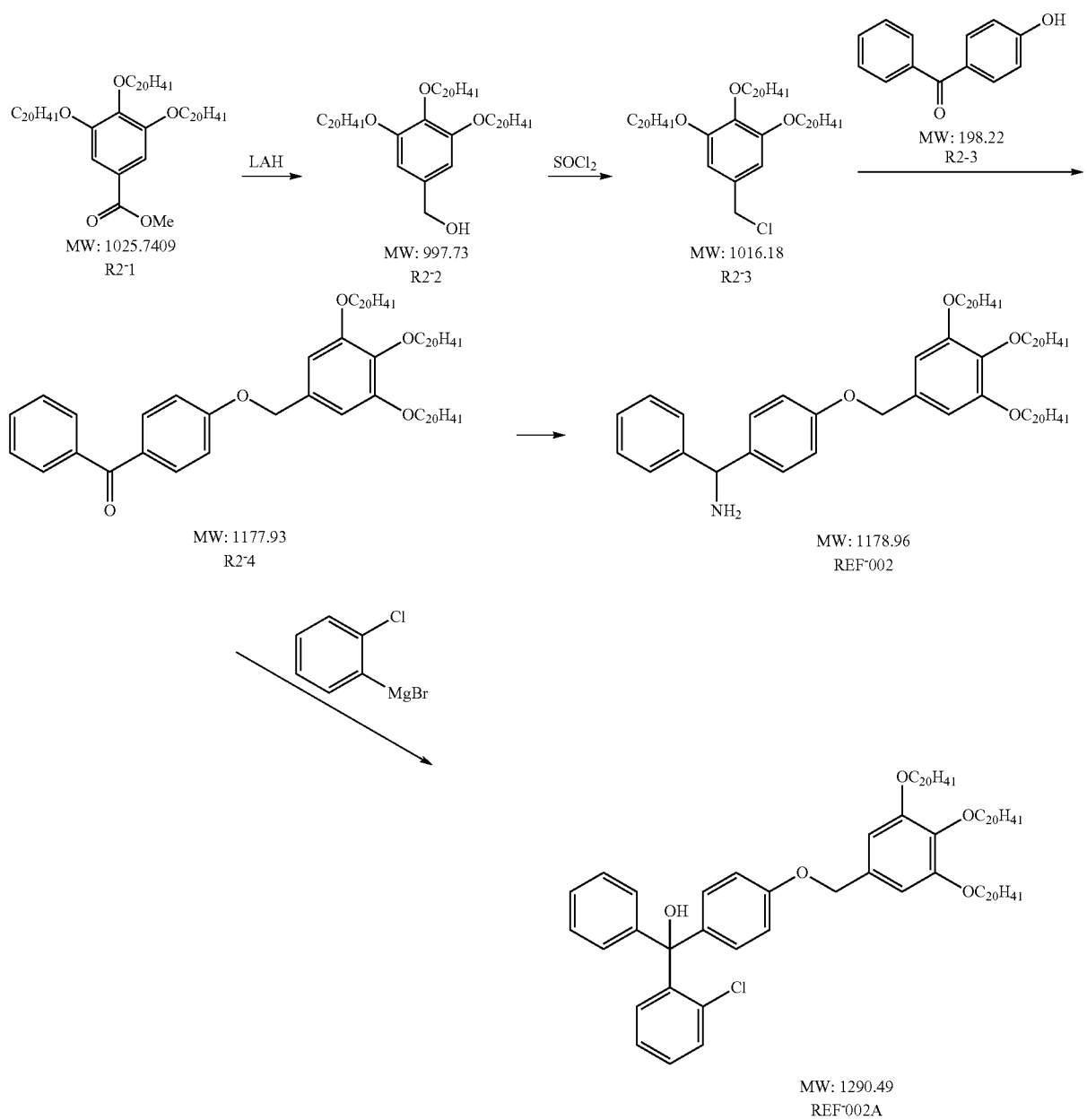

C₂₀H₄₁ = 2,3-dihydrophytanyl

The raw material R2-1 was synthesized according to the methods in Example 2. R2-1 (28.0 g, 0.05 mol) was dissolved in anhydrous tetrahydrofuran (200 mL), and the temperature was reduced to 5-10° C.; lithium aluminum tetrahydride (1.8 g, 0.05 mol) were added in batches, and after the addition was completed, the temperature was naturally raised to room temperature to react for 2 h; cooled down again to 5-10° C., saturated sodium sulfate solution was added dropwise until no bubbles were emerged; filtered to remove the solids, and concentrate the filtrate to obtain an intermediate R2-2 (21.5 g).

R2-2 was dissolved in dichloromethane (100 mL) and the temperature was reduced to 0-5° C.; thionyl chloride (6 g, 0.05 mol) was added dropwise while keeping the temperature, and after the addition was completed, the temperature was kept at 0-5° C. and continued to react for 1 h; water (100 mL) was added to quench the reaction, and the aqueous layer was separated, the dichloromethane layer was washed with water (100 mL*2), dried by anhydrous sodium sulfate, and concentrated to obtain an intermediate R2-3 (22.0 g).

The 4-(3,4,5-tri(2,3-dihydrophytanyloxy)-benzyloxy-benzhydrylamine (REF-002) was prepared by a series of reactions of the intermediate R2-3 with 4-hydroxybenzophenone according to the methods in Example 1. $^1$H-NMR (400 MHz, CDCl$_3$): δ0.80-1.80 (m, 117H) 3.90-4.10 (m, 6H), 5.05 (s, 2H), 5.20 (s, 1H), 6.63 (s, 2H), 6.80-6.90 (d, 2H), 7.20-745 (m, 7H); HRMS TOF [M+1]$^+$: 1178.4540.

The intermediate R2-4 was dissolved in anhydrous tetrahydrofuran, and 2-chloro-bromobenzene Grignard reagent (2 eq) was added dropwise, the reaction solution was heated to reflux for 8 h, and saturated ammonium chloride solution was added to quench the reaction, and extracted with petroleum ether, and concentrated to obtain a crude product, purified by column chromatography to obtain REF-002A. $^1$H-NMR (400 MHz, CDCl$_3$): δ0.80-1.80 (m, 117H), 3.90-4.10 (m, 6H), 5.05 (s, 2H), 6.60 (s, 2H), 6.80-6.90 (d, 2H), 7.20-7.25 (d, 2H), 7.30-7.40 (m, 9H), 7.60-7.65 (m, 1H); HRMS TOF [M−17]$^+$: 1272.0434.

Comparative Example 3

Synthesis of 4,4'-di(3,4,5-tri(isononyloxy)-benzyloxy)-benzhydrylamine (REF-003)

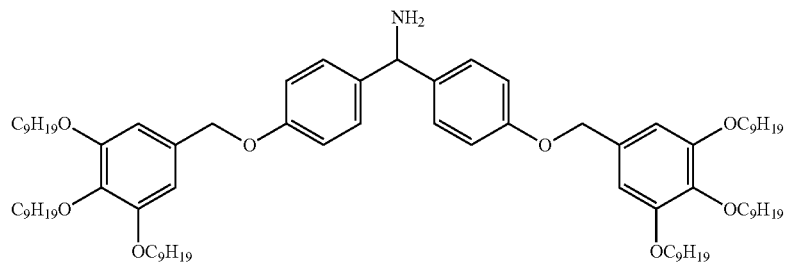

MW: 1248.92
REF-003

The 4,4'-di(3,4,5-tri(isononyloxy)-benzyloxy)-benzhydrylamine (REF-003) was prepared according to the methods in Comparative Example 2 by using 3,4,5-tris(isononyloxy)-benzoic acid instead of R2-1 and using 4,4'-hydroxybenzophenone instead of 4-hydroxybenzophenone. $^1$H-NMR (400 MHz, CDCl$_3$): δ0.80-1.80 (m, 102H), 3.90-4.10 (m, 12H), 5.05 (s, 4H), 5.20 (s, 1H), 6.63 (s, 4H), 6.80-6.90 (d, 4H), 7.20-7.40 (d, 4H); HRMS TOF [M+1]$^+$: 1248.7540.

Example 36 the Solubility of the Compound of the Present Invention in Common Solvents The solubility of the compound of the present invention in common solvents was investigated (25-30° C.), and the results are shown in Table 1. It can be seen from Table 1 that the compound of the present invention has good solubility in all of heptane, isopropyl acetate (i-PrOAc), methyl tert-butyl ether (MTBE) and N,N-dimethylformamide (DMF), and particularly, the solubility in N,N-dimethylformamide is much higher than Comparative Examples.

TABLE 1

| Carrier | Heptane (%) | i-PrOAc (%) | MTBE (%) | DMF (%) | MeOH (%) | DMSO (%) |
|---|---|---|---|---|---|---|
| DPA-001 | >25 | >30 | >30 | >20 | <1 | <1 |
| DPA-002 | >50 | >100 | >100 | >20 | <1 | <1 |
| DPA-003 | >50 | >100 | >100 | >20 | <1 | <1 |
| DPA-004 | >50 | >100 | >100 | >1 | <1 | <1 |
| DPA-005 | >50 | >100 | >100 | >10 | <1 | <1 |
| DPA-006 | >100 | >100 | >100 | >100 | <1 | <1 |
| DPA-007 | >100 | >100 | >100 | >100 | <1 | <1 |
| DPA-008 | >100 | >100 | >100 | >100 | <1 | <1 |
| DPA-009 | >10 | >25 | >30 | >30 | <1 | <1 |
| DPA-010 | >100 | >40 | >30 | >100 | <5 | <1 |
| DPA-011 | >100 | >100 | >50 | >150 | <1 | <1 |
| DPA-012 | >100 | >100 | >100 | >100 | <5 | <10 |
| DPA-013 | >50 | >70 | >50 | >50 | <1 | <1 |
| DPA-014 | >30 | >50 | >50 | >40 | <10 | <10 |
| DPA-015 | >50 | >100 | >100 | >100 | <1 | <1 |
| DPA-016 | >100 | >100 | >100 | >100 | <1 | <1 |
| DPA-017 | >100 | >100 | >100 | >100 | <5 | <5 |
| DPA-018 | >5 | >100 | >100 | >100 | <10 | <5 |
| DPA-019 | >50 | >100 | >100 | >50 | <10 | <5 |
| DPA-020 | >100 | >100 | >100 | >100 | <5 | <5 |
| DPA-021 | >50 | >100 | >100 | >100 | <1 | <1 |
| DPA-022 | >50 | >100 | >100 | >100 | <1 | <1 |
| DPA-023 | >50 | >50 | >50 | >30 | <5 | <5 |
| DPA-024 | >50 | >100 | >100 | >30 | <1 | <1 |
| DPA-025 | >100 | >100 | >100 | >100 | <1 | <1 |
| DPA-026 | >50 | >100 | >100 | >100 | <1 | <1 |
| DPA-027 | >50 | >75 | >75 | >75 | <1 | <1 |
| DPA-028 | >100 | >100 | >100 | >100 | <1 | <1 |

TABLE 1-continued

| Carrier | Heptane (%) | i-PrOAc (%) | MTBE (%) | DMF (%) | MeOH (%) | DMSO (%) |
|---|---|---|---|---|---|---|
| DPA-029 | >100 | >100 | >100 | >100 | <1 | <1 |
| DPA-030 | >40 | >40 | >40 | >40 | <1 | <1 |
| DPA-031 | >50 | >100 | >100 | >100 | <1 | <1 |
| DPA-032 | >10 | >10 | >10 | >40 | <1 | <1 |
| DPA-033 | >30 | >50 | >50 | >40 | <1 | <1 |
| DPA-034 | >30 | >50 | >50 | >40 | <1 | <1 |
| REF-001 | >50 | >100 | >100 | >0.1 | <1 | <1 |
| REF-002 | >100 | >100 | >100 | >0.1 | <1 | <1 |
| REF-002A | >100 | >100 | >100 | >0.1 | <1 | <1 |
| REF-003 | >100 | >100 | >100 | >0.1 | <1 | <1 |

Example 37

Synthesis of H-Glu-Met-Glu-Gln-Arg-Arg-NH$_2$ through heterogeneous method with the carrier of DPA-002

DPA-002 was dissolved in heptane, stirred and cooled to 15-20° C.; Fmoo-Arg(Pbf)-OH (the amount of Fmoc-Arg(Pbf)-OH used was 1-1.5 equivalents of DPA-002), diisopropyl ethylamine (the amount of diisopropylethyl amine used was 2-3 equivalents of DPA-002) and HOBt (the amount of HOBt used was 1-1.5 equivalents of DPA-002) were dissolved in DMF and added to the reactor under stirring; kept at 15-20° C., DMF solution of HBTU (the amount of HOBt used was 1-1.5 equivalents of DPA-002) was added to react.

After the reaction was completed, water was added and continued to stir, and was left stand for layering; the lower layer was separated and DMF:water (the volume ratio of DMF to water was (1~10):1)) were added, stirred and was left stand for layering; the lower layer was separated, and the upper layer was directly used for the Fmoc removing step.

The upper layer solution obtained in the above steps was heated to 40-45° C., and a mixture solution of mercaptopropionic acid (the amount of mercaptopropionic acid used was 3~5 equivalents of DPA-002), diethylene triamine (the amount of diethylene triamine used was 3~6 equivalents of DPA-002) and DMF was added and reacted at 40-45° C. After the reaction was completed, DMF:water (the volume ratio of DMF to water was (1~10):1) were added, stirred and was left stand for layering; the lower layer was separated, the upper layer was added with DMF:water (the volume ratio of DMF to water was (1~10):1), stirred and was left stand for layering; the lower layer was separated, and repeating the above washing steps for the upper layer until the eluate was neutral, and the upper layer was used directly for the next amino acid condensation.

Fmoc-Arg(Pbf)-OH, Fmoc-Gln(Trt)-OH, Fmoc-Glu(OtBu)-OH, Fmoc-Met-OH and Fmoc-Glu(OtBu)-OH were inserted according to the above methods, and after removing the Fmoc, a heptane solution of H-Glu(OtBu)-Glu(OtBu)-Met-Gln(Trt)-Arg(Pbf)-Arg(Pbf)-(DPA-002) was obtained, and concentrated to obtain a solid.

H-Glu(OtBu)-Met-Glu(OtBu)-Gln(Trt)-Arg(Pbf)-Arg(Pbf)-(DPA-002) was dissolve in TFA:TIS:water (5-10 volume of crude product, 94:3:3), and stirred at room temperature for 2 h. Methyl tert-butyl ether was slowly added dropwise at 0-10° C., the temperature was kept at 0-10° C. and stirred for half an hour; filtered, and the filter cake was washed with methyl tert-butyl ether until the eluate was neutral, dried to obtain a crude product of H-Glu-Glu-Met-Gln-Arg-Arg-$NH_2$, and the purity was 85.3% by HPLC, HRMS TOF $[M+1]^+$: 889.2309.

Example 38

Synthesis of H-Glu-Met-Glu-Gln-Arg-Arg-$NH_2$ Through Heterogeneous Method with the Carrier of DPA-005

The synthesis method of this Example is the same as that of Example 37, except that DPA-005 was used instead of the carrier in Example 37, and the purity was 80.0% by HPLC.

Example 39

Synthesis of H-Glu-Met-Glu-Gln-Arg-Arg-$NH_2$ Through Heterogeneous Method with the Carrier of DPA-007

The synthesis method of this Example is the same as that of Example 37, except that DPA-007 was used instead of the carrier in Example 37, and the purity was 87.4% by HPLC.

Example 40

Synthesis of H-Glu-Met-Glu-Gln-Arg-Arg-$NH_2$ Through Heterogeneous Method with the Carrier of DPA-009

The synthesis method of this Example is the same as that of Example 37, except that DPA-009 was used instead of the carrier in Example 37, and the purity was 83.4% by HPLC.

Example 41

Synthesis of H-Glu-Met-Glu-Gln-Arg-Arg-$NH_2$ Through Heterogeneous Method with the Carrier of DPA-010

The synthesis method of this Example is the same as that of Example 37, except that DPA-010 was used instead of the carrier in Example 37, and the purity was 81.5% by HPLC.

Example 42

Synthesis of H-Glu-Met-Glu-Gln-Arg-Arg-$NH_2$ Through Heterogeneous Method with the Carrier of DPA-012

The synthesis method of this Example is the same as that of Example 37, except that DPA-012 was used instead of the carrier in Example 37, and the purity was 82.5% by HPLC.

Example 43

Synthesis of H-Glu-Met-Glu-Gln-Arg-Arg-$NH_2$ Through Heterogeneous Method with the Carrier of DPA-018

The synthesis method of this Example is the same as that of Example 37, except that DPA-018 was used instead of the carrier in Example 37, and the purity was 84.3% by HPLC.

Example 44

Synthesis of H-Glu-Met-Glu-Gln-Arg-Arg-$NH_2$ Through Heterogeneous Method with the Carrier of DPA-019

The synthesis method of this Example is the same as that of Example 37, except that DPA-019 was used instead of the carrier in Example 37, and the purity was 82.2% by HPLC.

Example 45

Synthesis of H-Glu-Met-Glu-Gln-Arg-Arg-$NH_2$ Through Heterogeneous Method with the Carrier of DPA-022

The synthesis method of this Example is the same as that of Example 37, except that DPA-022 was used instead of the carrier in Example 37, and the purity was 84.5% by HPLC.

Example 46

Synthesis of H-Glu-Met-Glu-Gln-Arg-Arg-$NH_2$ Through Heterogeneous Method with the Carrier of DPA-024

The synthesis method of this Example is the same as that of Example 37, except that DPA-024 was used instead of the carrier in Example 37, and the purity was 85.5% by HPLC.

Example 47

Synthesis of H-Glu-Met-Glu-Gln-Arg-Arg-NH$_2$ Through Heterogeneous Method with the Carrier of DPA-025

The synthesis method of this Example is the same as that of Example 37, except that DPA-025 was used instead of the carrier in Example 37, and the purity was 83.8% by HPLC.

Example 48

Synthesis of H-Glu-Met-Glu-Gln-Arg-Arg-NH$_2$ Through Heterogeneous Method with the Carrier of DPA-027

The synthesis method of this Example is the same as that of Example 37, except that DPA-027 was used instead of the carrier in Example 37, and the purity was 86.2% by HPLC.

Example 49

Synthesis of H-Glu-Met-Glu-Gln-Arg-Arg-NH$_2$ Through Heterogeneous Method with the Carrier of DPA-030

The synthesis method of this Example is the same as that of Example 37, except that DPA-030 was used instead of the carrier in Example 37, and the purity was 85.2% by HPLC.

Example 50

Synthesis of H-Phe-Ala-Leu-Gly-Arg-NH$_2$ Through Heterogeneous Method with the Carrier of DPA-008

DPA-008 was dissolved in heptane, stirred and cooled to 15-20° C.; Boo-Arg(Pbf)-OH (the amount of Boc-Arg(Pbf)-OH used was 1-1.5 equivalents of DPA-008), diisopropylethylamine (the amount of diisopropylethylamine used was 2-3 equivalents of DPA-008) and HOBt (the amount of HOBt used was 1-1.5 equivalents of DPA-008) were dissolved in DMF and added to the reactor under stirring; kept at 15-20° C., and a DMF solution of HBTU (the amount of HBTU used was 1-1.5 equivalents of DPA-008) was added to react.

After the reaction was completed, water was added and continued to stir, and was left stand for layering; the lower layer was separated, and DMF:water (the volume ratio of DMF to water was (1~10) were added, stirred and was left stand for layering; the lower layer was separated, and the upper layer was directly used for the Boc removing step.

The upper layer solution obtained in the above steps was cooled to 0-5° C., and methanesulfonic acid (the amount of methanesulfonic acid used was 3-5 equivalents of DPA-008) was added dropwise, stirred at room temperature until the reaction was completed, then re-cooled to 0-5° C.; 10% sodium carbonate aqueous solution was added dropwise for neutralization; the aqueous layer was separated, and the organic layer was extracted and washed once with DMF:water (the volume ratio of DMF to water was (1~10)), and it was directly used for the next amino acid reaction.

Boc-Gly-OH, Boc-Leu-OH, Boc-Ala-OH and Boc-Phe-OH were inserted sequentially according to the above steps to obtain the Boc-Phe-Ala-Leu-Gly-Arg-(DPA-008).

Boc-Phe-Ala-Leu-Gly-Arg-(DPA-008) was dissolved in TFA:TIS:water (94:3:3) and stirred at room temperature for 2 h. Methyl tert-butyl ether at 0-10° C. was slowly added dropwise, the temperature was kept at 0-10° C. and stirred for half an hour; filtered, and the filter cake was washed with methyl tert-butyl ether until the eluate was neutral, dried to obtain a crude product of H-Phe-Ala-Leu-Gly-Arg-NH$_2$, and the purity was 95.3% by HPLC, HRMS TOF [M+1]$^+$: 562.2387.

Example 51

Synthesis of H-Lys-Thr-Thr-Lys-Ser-OH Through Heterogeneous Method with the Carrier of DPA-033

DPA-033 was dissolved in DCM, cooled to −5-0° C., and SOCl$_2$ was added dropwise (the amount of SOCl$_2$ used was 1-2 equivalents of DPA-033); naturally raised to room temperature and reacted for half an hour, re-cooled to −5-0° C., washed with ice water until the methylene chloride layer was neutral, dried by anhydrous sodium sulfate and filtered, and then it was directly used for the next step.

To the solution obtained in the above step, Fmoc-Ser(tBu)-OH (the amount of Fmoc-Ser(tBu)-OH used was 1-3 equivalents of DPA-033) and diisopropylethylamine (the amount of diisopropylethylamine used was 2-3 equivalents of DPA-033) were added sequentially, and reacted at room temperature; after the reaction was completed, 100 mL of heptane was added, the dichloromethane was evaporated, and the heptane solution was washed with DMF/water (the volume ratio of DMF to water was (1~10):1), and the upper layer was directly used for the next step of Fmoc removing reaction.

Fmoc-Lys(Boc)-OH, Fmoc-Thr(tBu)-OH, Fmoc-Thr(tBu)-OH and Fmoc-Lys(Boc)-OH were inserted sequentially according to the steps of Fmoc removing-Fmoc-protected amino acids inserting-Fmoc removing in Example 37, to obtain H-Lys(Bo)-Thr(tBu)-Thr(tB)-Lys(Boc)-Ser(tBu)-(DPA-033).

H-Lys(Boc)-Thr(tBu)-Thr(tBu)-Lys(Boc)-Ser(tBu)-(DPA-033) was dissolved in TFA:TIS:water (94:3:3), and stirred at room temperature for 2 h. Methyl tert-butyl ether at 0-10° C. was slowly added dropwise, the temperature was kept at 0-10° C. and stirred for half an hour; filtered, and the filter cake was washed with methyl tert-butyl ether until the eluate was neutral, dried to obtain a crude product of H-Lys-Thr-Thr-Lys-Ser-OH, and the purity was 96.8% by HPLC, HRMS TOF [M+1]$^+$: 564.3350.

Example 52

Synthesis of H-β-Ala-Pro-Dab-NHBn Through Heterogeneous Method with DPA-035

DPA-035 (5.4 g, 0.005 mol) was used as the carrier, and Fmoc-Dab(Boc)-OH, Fmoc-Pro-OH and Boc-β-Ala-OH were inserted sequentially according to the steps of the methods in Example 37, to obtain Boc-β-Ala-Pro-Dab(Boc)-(DPA-035).

Boc-β-Ala-Pro-Dab(Boc)-(DPA-035) was dissolved in TFA:TIS:water (50 mL, 94:3:3), and stirred at room temperature for 2 h. Methyl tert-butyl ether (250 mL) at 0-10° C. was slowly added dropwise, the temperature was kept at 0-10° C. and stirred for half an hour; filtered, and the filter cake was washed with methyl tert-butyl ether until the eluate was neutral, dried to obtain H-β-Ala-Pro-Dab-NHBn, and the purity was 98.8% by HPLC, HRMS TOF [M+1]$^+$: 376.4186.

Example 53

Synthesis of H-Glu-Met-Glu-Gln-Arg-Arg-NH$_2$ Through Homogeneous Method with DPA-002

1) DPA-002 (14.5 g, 10.0 mmol) was dissolved in isopropyl acetate (100 mL), Fmoc-Arg(Pbf)-OH (9.7 g, 15.0 mmol), HOBt (2.0 g, 15 mmol) and DIPEA (3.24 g, 25.0 mmol) was added, stirred and cooled to 5-10° C., HBTU (5.62 g, 15 mmol) was added to react; after the reaction was completed, acetonitrile/water (9:1) were added to wash (isopropyl acetate was additionally added as needed), and the isopropyl acetate solution was used for the next step of the Fmoc removing reaction.
2) To the obtained isopropyl acetate solution in Step 1), diethylene triamine (6.2 g, 60 mmol) and mercaptopropionic acid (4.3 g, 40 mmol) were added and heated to 40-50° C. to react After the reaction was completed by TLC analysis, washed with acetonitrile/water (9:1) (isopropyl acetate was additionally added as needed) to remove by-products. The isopropyl acetate solution was used for the next amino acid condensation.
3) Fmoc-Arg(Pbf)-OH, Fmoc-Gln(Trt)-OH, Fmoc-Glu(OtBu)-OH, Fmoc-Met-OH and Fmoc-Glu(OtBu)-OH were inserted continuously according to the above methods, and after Fmoc was removed, a isopropyl acetate solution of H-Glu(OtBu)-Met-Glu(OtBu)-Gln(Trt)-Arg(Pbf)-Arg(Pbf)-(DPA-002) was obtained, which was concentrated to obtain a solid;
4) The crude product of H-Glu-Met-Glu-Gln-Arg-Arg-NH$_2$ was obtained by cracking according to the methods in Example 37, and the purity was 65.2% by HPLC.

Example 54

Synthesis of H-Glu-Met-Glu-Gln-Arg-Arg-NH$_2$ Through Homogeneous Method with DPA-006

The synthesis method of this Example is the same as that of Example 53, except that DPA-006 was used instead of the carrier in Example 53, and the purity was 66.0% by HPLC.

Example 55

Synthesis of H-Glu-Met-Glu-Gln-Arg-Arg-NH$_2$ Through Homogeneous Method with DPA-012

The synthesis method of this Example is the same as that of Example 53, except that DPA-012 was used instead of the carrier in Example 53, and the purity was 63.0% by HPLC.

Example 56

Synthesis of H-Glu-Met-Glu-Gln-Arg-Arg-NH$_2$ Through Homogeneous Method with DPA-019

The synthesis method of this Example is the same as that of Example 53, except that DPA-019 was used instead of the carrier in Example 53, and the purity was 60.0% by HPLC.

Comparative Example 4

Synthesis of H-Glu-Met-Glu-Gln-Arg-Arg-NH$_2$ Through Heterogeneous Method with REF-001

REF-001 was used instead of DPA-002 to synthesize H-Glu-Met-Glu-Gln-Arg-Arg-NH$_2$ according to the steps in Example 37, and when the third amino acid was inserted in the reaction, the solubility decreased significantly. After that, the solvent needs to be supplemented for each step of the reaction, the layering became difficult, the post-treatment time was prolonged, and the crude product has a purity of 68.5% by HPLC.

Comparative Example 5

Synthesis of H-Glu-Met-Glu-Gln-Arg-Arg-NH$_2$ Through Heterogeneous Method with REF-002

REF-002 was used instead of DPA-002 to synthesize H-Glu-Met-Glu-Gln-Arg-Arg-NH$_2$ according to the steps in Example 37, and the purity was 70.5% by HPLC.

Comparative Example 6

Synthesis of H-Glu-Met-Glu-Gln-Arg-Arg-NH$_2$ Through Heterogeneous Method with REF-003

REF-003 was used instead of DPA-002 to synthesize H-Glu-Met-Glu-Gln-Arg-Arg-NH$_2$ according to the steps in Example 37, and the purity was 65.5% by HPLC.

Comparative Example 7

Synthesis of H-Lys-Thr-Thr-Lys-Ser-OH Through Heterogeneous Method with REF-002A REF-002A was used instead of DPA-033 to synthesize H-Lys-Thr-Thr-Lys-Ser-OH according to the steps in Example 51, and the purity was 85.5% by HPLC.

Comparative Example 8

Synthesis of H-Glu-Met-Glu-Gln-Arg-Arg-NH$_2$ Through Homogeneous Method with REF-001

REF-001 was used instead of DPA-002 to synthesize H-Glu-Met-Glu-Gln-Arg-Arg-NH$_2$ according to the steps in Example 53, and the purity was 50.0% by HPLC.

Comparative Example 9

Synthesis of H-Glu-Met-Glu-Gln-Arg-Arg-NH$_2$ Through Homogeneous Method with REF-002

REF-002 was used instead of DPA-002 to synthesize H-Glu-Met-Glu-Gln-Arg-Arg-NH$_2$ according to the steps in Example 53, and the purity was 55.0% by HPLC.

Comparative Example 10

Synthesis of H-Glu-Met-Glu-Gln-Arg-Arg-NH$_2$ Through Homogeneous Method with REF-003

REF-003 was used instead of DPA-002 to synthesize H-Glu-Met-Glu-Gln-Arg-Arg-NH$_2$ according to the steps in Example 53, and the purity was 51.0% by HPLC.

Example 57

The condensation reaction time, the post-treatment time of condensation reaction, deprotection reaction time and the post-treatment time of deprotection, and the purity by HPLC of the polypeptide synthesis using the compound of the present invention and the comparative compound as a carrier are measured. Among them, a synthesis of H-Glu-Met-Glu-Gln-Arg-Arg-NH$_2$ (DPA-002, DPA-005, DPA-006, DPA-007, DPA-010, DPA-012, DPA-018, DPA-019, DPA-022, DPA-024, DPA-025, DPA-027, DPA-030, REF-001, REF-002, REF-003) by homogeneous method and heterogeneous method, a synthesis of H-Lys-Thr-Thr-Lys-Ser-OH (DPA-033 and REF-002A) by heterogeneous method, a synthesis of H-Phe-Ala-Leu-Gly-Arg-NH$_2$ (DPA-008) by heterogeneous method and a synthesis of H-β-Ala-Pro-Dab-NHBn (DPA-035) by heterogeneous method are included, and the results are shown in Table 2. Among them, AA$_1$ is the first amino acid, AA$_2$ is the second amino acid, AA$_3$ is the third amino acid, AA$_4$ is the fourth amino acid, AA$_5$ is the fifth amino acid, AA$_6$ is the sixth amino acid, and $t_R$ is the condensation reaction time, $t_w$ is the post-treatment time of condensation reaction, $t_D$ is the deprotection reaction time, and $t_{Dw}$ is the post-treatment time of deprotection reaction, unit: hour.

TABLE 2

| Carrier | AA$_1$ | | | | AA$_2$ | | | | AA$_3$ | | | | AA$_4$ | | | |
|---|---|---|---|---|---|---|---|---|---|---|---|---|---|---|---|---|
| | $t_R$ | $t_W$ | $t_D$ | $t_{Dw}$ | $t_R$ | $t_W$ | $t_D$ | $t_{Dw}$ | $t_R$ | $t_W$ | $t_D$ | $t_{Dw}$ | $t_R$ | $t_W$ | $t_D$ | $t_{Dw}$ |
| DPA-002 | 0.5 | 0.5 | 0.8 | 0.5 | 0.8 | 0.5 | 1.0 | 0.5 | 0.5 | 0.5 | 0.5 | 1.0 | 0.5 | 0.5 | 0.8 | 1.0 |
| DPA-005 | 1.0 | 0.5 | 0.8 | 0.5 | 0.8 | 0.5 | 1.0 | 0.5 | 0.8 | 0.5 | 0.8 | 0.5 | 0.8 | 0.5 | 0.8 | 1.0 |
| DPA-006 | 0.5 | 0.5 | 1.0 | 0.5 | 0.5 | 0.5 | 0.8 | 0.5 | 0.5 | 0.5 | 1.0 | 0.5 | 1.0 | 0.5 | 0.5 | 0.5 |
| DPA-007 | 0.6 | 0.5 | 1.5 | 0.5 | 0.5 | 0.5 | 0.8 | 0.5 | 0.5 | 0.5 | 1.0 | 0.5 | 1.2 | 0.5 | 0.5 | 0.5 |
| DPA-010 | 1.0 | 0.5 | 0.5 | 0.5 | 0.5 | 0.5 | 0.5 | 0.5 | 0.5 | 0.5 | 0.5 | 0.5 | 1.0 | 0.5 | 0.5 | 0.5 |
| DPA-012 | 1.0 | 0.5 | 0.5 | 0.5 | 0.8 | 0.5 | 0.5 | 0.5 | 0.8 | 0.5 | 0.8 | 0.5 | 0.8 | 0.5 | 0.5 | 1.0 |
| DPA-018 | 0.5 | 0.5 | 0.8 | 0.5 | 0.8 | 0.5 | 1.5 | 0.5 | 0.5 | 0.5 | 0.5 | 1 | 0.5 | 0.5 | 0.8 | 0.5 |
| DPA-019 | 1.0 | 0.5 | 0.5 | 0.5 | 0.8 | 0.5 | 0.5 | 0.5 | 0.8 | 0.5 | 0.8 | 0.5 | 0.8 | 0.5 | 0.5 | 1.0 |
| DPA-022 | 0.8 | 0.5 | 0.5 | 0.5 | 0.5 | 0.5 | 0.5 | 0.5 | 0.5 | 0.5 | 1.0 | 0.5 | 0.5 | 0.5 | 0.8 | 0.5 |
| DPA-024 | 0.5 | 0.5 | 1.0 | 0.5 | 0.8 | 0.5 | 1.0 | 0.5 | 0.9 | 0.5 | 1.0 | 0.5 | 0.8 | 0.5 | 0.8 | 0.8 |
| DPA-025 | 1.5 | 0.5 | 0.8 | 0.5 | 0.5 | 0.5 | 1.0 | 0.5 | 0.5 | 0.5 | 0.8 | 0.5 | 0.8 | 0.5 | 0.8 | 0.5 |
| DPA-027 | 0.5 | 0.5 | 1.0 | 0.5 | 0.8 | 0.5 | 0.5 | 0.5 | 0.5 | 0.5 | 0.5 | 0.8 | 0.5 | 0.5 | 0.8 | 0.5 |
| DPA-030 | 0.6 | 0.5 | 1.5 | 0.5 | 1.0 | 0.5 | 0.8 | 0.5 | 0.5 | 0.5 | 0.9 | 0.5 | 1.2 | 0.5 | 0.5 | 0.5 |
| DPA-002* | 3.0 | 2.5 | 6.0 | 2.5 | 5.0 | 2.5 | 6.0 | 2.5 | 3.5 | 2.5 | 6.0 | 2.5 | 4.0 | 2.5 | 5.5 | 2.5 |
| DPA-006* | 3.0 | 2.5 | 6.0 | 2.5 | 5.5 | 2.5 | 5.5 | 2.5 | 4.0 | 2.5 | 6.0 | 2.5 | 4.0 | 2.5 | 5.5 | 2.5 |
| DPA-012* | 3.0 | 2.5 | 6.0 | 2.5 | 5.0 | 2.5 | 5.5 | 2.5 | 4.0 | 2.5 | 6.0 | 2.5 | 4.0 | 2.5 | 6.0 | 2.5 |
| DPA-019* | 3.0 | 2.5 | 6.0 | 2.5 | 5.0 | 2.5 | 5.5 | 2.5 | 4.5 | 2.5 | 6.0 | 2.5 | 4.0 | 2.5 | 6.0 | 2.5 |
| DPA-008 | 0.8 | 0.5 | 1.0 | 0.5 | 0.5 | 0.5 | 1.0 | 0.5 | 1.0 | 0.5 | 1.0 | 0.5 | 0.8 | 0.5 | 1.0 | 0.5 |
| DPA-033 | 8.0 | 0.5 | 0.5 | 0.5 | 0.5 | 0.5 | 0.5 | 0.5 | 0.5 | 0.5 | 0.5 | 0.5 | 0.8 | 0.5 | 0.5 | 0.5 |
| DPA-035 | 1.0 | 0.5 | 0.5 | 0.5 | 0.5 | 0.5 | 0.5 | 0.5 | 0.5 | 0.5 | 0.5 | 0.5 | — | — | — | — |
| REF-001 | 2.0 | 1.0 | 2.5 | 2.0 | 3.0 | 1.0 | 2.0 | 2.0 | 2.5 | 1.0 | 2.0 | 2.5 | 3.0 | 3.0 | 2.0 | 4.0 |
| REF-002 | 2.0 | 1.0 | 2.5 | 2.0 | 3.0 | 1.2 | 2.0 | 2.0 | 2.5 | 1.0 | 2.0 | 2.5 | 3.0 | 3.0 | 2.0 | 3.5 |
| REF-003 | 2.5 | 1.0 | 3.0 | 2.5 | 3.0 | 1.5 | 2.0 | 2.0 | 2.5 | 2.0 | 2.0 | 2.5 | 3.0 | 3.5 | 2.0 | 4.0 |
| REF-001* | 4.0 | 2.5 | 6.0 | 2.5 | 8.0 | 2.5 | 6.0 | 2.5 | 5.0 | 2.5 | 6.0 | 2.5 | 5.0 | 3.0 | 6.0 | 3.0 |
| REF-002* | 4.0 | 2.5 | 6.0 | 2.5 | 8.0 | 2.5 | 6.0 | 2.5 | 5.0 | 2.5 | 6.0 | 2.5 | 5.0 | 3.0 | 6.0 | 3.0 |
| REF-003* | 4.0 | 2.5 | 6.0 | 2.5 | 8.0 | 2.5 | 6.0 | 2.5 | 5.0 | 2.5 | 6.0 | 2.5 | 5.0 | 3.0 | 6.0 | 3.0 |
| REF-002A | 8.0 | 1.0 | 2.5 | 1.0 | 2.0 | 2.0 | 2.0 | 2.0 | 3.0 | 2.0 | 2.0 | 2.0 | 3.0 | 2.0 | 1.5 | 2.0 |

| Carrier | AA$_5$ | | | | AA$_6$ | | | | HPLC (%) |
|---|---|---|---|---|---|---|---|---|---|
| | $t_R$ | $t_w$ | $t_D$ | $t_{Dw}$ | $t_R$ | $t_W$ | $t_D$ | $t_{Dw}$ | |
| DPA-002 | 0.7 | 0.5 | 0.8 | 0.5 | 0.8 | 0.5 | 0.5 | 0.8 | 85.3 |
| DPA-005 | 0.5 | 0.5 | 0.8 | 0.5 | 1.0 | 0.5 | 0.8 | 0.5 | 80.0 |
| DPA-006 | 0.5 | 0.5 | 1 | 0.5 | 1.0 | 0.5 | 0.5 | 0.5 | 87.4 |
| DPA-007 | 0.5 | 0.5 | 0.5 | 0.5 | 1.5 | 0.5 | 0.5 | 0.5 | 83.4 |
| DPA-010 | 1.0 | 0.5 | 1.0 | 0.5 | 1.5 | 0.5 | 0.5 | 1.0 | 81.5 |
| DPA-012 | 0.5 | 0.5 | 0.5 | 0.5 | 1.0 | 0.5 | 0.8 | 0.5 | 82.5 |
| DPA-018 | 0.6 | 0.5 | 0.8 | 0.5 | 0.5 | 0.5 | 0.5 | 0.8 | 84.3 |
| DPA-019 | 1.0 | 0.5 | 0.5 | 0.5 | 1.0 | 0.5 | 0.8 | 0.5 | 82.2 |
| DPA-022 | 0.5 | 0.5 | 0.8 | 0.5 | 1.1 | 0.5 | 0.5 | 0.5 | 84.5 |
| DPA-024 | 0.5 | 0.5 | 0.8 | 0.5 | 1.3 | 0.5 | 0.8 | 0.5 | 85.5 |
| DPA-025 | 0.8 | 0.5 | 0.8 | 0.5 | 0.5 | 0.5 | 0.8 | 0.5 | 83.8 |
| DPA-027 | 0.7 | 0.5 | 1.0 | 0.5 | 0.8 | 0.5 | 0.5 | 0.8 | 86.2 |
| DPA-030 | 0.5 | 0.5 | 0.5 | 0.5 | 1.0 | 0.5 | 0.5 | 0.5 | 85.2 |
| DPA-008 | 0.5 | 0.5 | — | — | — | — | — | — | 95.3 |
| DPA-033 | 0.5 | 0.5 | 0.5 | 0.5 | — | — | — | — | 96.8 |
| DPA-035 | — | — | — | — | — | — | — | — | 98.8 |
| DPA-002* | 2.0 | 2.5 | 6.0 | 2.5 | 4.5 | 2.5 | 6.0 | 2.5 | 65.2 |
| DPA-006* | 2.0 | 2.5 | 6.0 | 2.5 | 4.5 | 2.5 | 6.0 | 2.5 | 66.0 |
| DPA-012* | 2.0 | 2.5 | 6.0 | 2.5 | 4.0 | 2.5 | 6.0 | 2.5 | 63.0 |
| DPA-019* | 2.0 | 2.5 | 6.0 | 2.5 | 4.5 | 2.5 | 6.0 | 2.5 | 60.0 |
| REF-001 | 3.0 | 4.0 | 2.0 | 4.0 | 3.0 | 4.0 | 2.0 | 4.0 | 68.5 |
| REF-002 | 3.0 | 3.0 | 2.0 | 3.0 | 3.0 | 3.0 | 2.0 | 3.0 | 70.5 |
| REF-003 | 3.0 | 4.0 | 2.0 | 4.5 | 3.0 | 4.0 | 2.0 | 4.5 | 65.5 |
| REF-001* | 4.0 | 3.0 | 6.0 | 3.0 | 6.0 | 3.0 | 6.0 | 3.0 | 50.0 |
| REF-002* | 4.0 | 3.0 | 6.0 | 3.0 | 6.0 | 3.0 | 6.0 | 3.0 | 55.0 |
| REF-003* | 4.0 | 3.0 | 6.0 | 3.0 | 6.0 | 3.0 | 6.0 | 3.0 | 51.0 |
| REF-002A | 2.0 | 3.0 | 2.0 | 3.5 | — | — | — | — | 85.5 |

*represents a homogeneous reaction, the rest are heterogeneous reactions.

It can be seen from Table 2 that the compound of the present invention was used as a carrier to synthesize H-Glu-Met-Glu-Gln-Arg-Arg-NH$_2$ hexapeptide. Compared with the comparative carrier REF-001~003, in the synthesis by heterogeneous method, the condensation reaction time, the post-treatment time of condensation reaction, deprotection reaction time and the post-treatment time of deprotection reaction were significantly shortened. Among them, in Comparative Examples REF-001~003, the condensation reaction time was greater than 2 hours, the post-treatment time of condensation reaction was greater than 1 hour, the deprotection reaction time was greater than 2.5 hours, and the post-treatment time of deprotection reaction was greater than 2 hours. With the compound of the present invention as a carrier, the condensation reaction time was 0.5~1.5 hours, the post-treatment time of condensation reaction was 0.5~1.0 hours, the deprotection reaction time was 0.5~1.5 hours, and the post-treatment time of deprotection reaction was 0.5~1.0 hours, in addition, the difference of the time required for the insert step of each amino acid fragment was very small, the repeatability was good, while the difference of the time required for the insert step of each amino acid fragment in Comparative Examples REF-001~003 was very large. In addition, in Comparative Examples REF-001~003, the solubility was decreased rapidly during the synthesis of peptides, and a gelation phenomenon began to appear at AA$_4$, and solvent needs to be supplemented to maintain the solution state. However, the compound of the present invention had a relatively good solubility during the synthesis of peptides, there was no need to supplement solvent in the whole process. The compound of the present invention was used as a carrier to synthesize peptides, and the purity of the product was greater than 80%, while the purity of the product in Comparative Examples REF-001~003 was not higher than 70%. In addition, when the compound comprising a diphenylmethane structure of the present invention was DPA-002, DPA-006, DPA-018, DPA-022, DPA-024, DPA-027 or DPA-030, the condensation reaction time, the post-treatment time of condensation reaction, the deprotection reaction time and the post-treatment time of deprotection reaction for the peptide synthesis using the compound as a carrier were shorter, and the product purity was higher.

The data of the synthesis of H-Lys-Thr-Thr-Lys-Ser-OH (DPA-033 and REF-002A) by heterogeneous method also reached the same conclusion. In the stage of peptide chain elongation (AA$_2$~AA$_5$), when DPA-033 was used as a carrier, the condensation reaction time was 0.5~1.0 hours, the post-treatment time of condensation reaction was 0.5 hours, the deprotection reaction time was 0.5 hours, and the post-treatment time of deprotection reaction was 0.5 hours. The difference of the time required for the insert step of each amino acid fragment was very small, the repeatability was good, while the difference of the time required for the insert step of each amino acid fragment in Comparative Example REF-002A was very large.

In the synthesis of H-Phe-Ala-Leu-Gly-Arg-NH$_2$(DPA-008) by heterogeneous method, the condensation reaction time was 0.5~1.0 hours, the post-treatment time of condensation reaction was 0.5 hours, the deprotection reaction time was 0.5 hours, and the post-treatment time of deprotection reaction was 0.5 hours. The difference of the time required for the insert step of each amino acid fragment was very small, and the repeatability was good.

In the synthesis of H-Glu-Met-Glu-Gln-Arg-Arg-NH$_2$ hexapeptide by homogeneous method, compared with Comparative Examples (REF-001~003*), when the compound of the present invention was used as a carrier, the condensation reaction time was significantly shorten and the product purity was significantly improved.

In summary, in the case of using the compound of the present invention as a carrier to synthesize a peptide, it is suitable for both homogeneous and heterogeneous solvent systems, and compared with the case of using the comparative compound as a carrier, it has a better effects. At the same time, the synthesis of peptide using the compound of the present invention as a carrier has a better effect in a heterogeneous system, especially in a two-phase system (heterogeneous system) formed by a low-to-medium polarity solvent and amide solvent than in a homogeneous system, and the condensation reaction time, the post-treatment time of condensation reaction, the deprotection reaction time, and the post-treatment time of deprotection reaction may be significantly shorten, and finally a product with a higher purity is obtained.

At last, it should be noted that the above embodiments are only used to illustrate the technical solutions of the present invention and not to limit the protection scope of the present invention. Although the present invention has been described in detail with reference to the preferred embodiments, those of ordinary skill in the art should understand that, the technical solution of the present invention can be modified or equivalently replaced without departing from the essence and scope of the technical solution of the present invention.

The invention claimed is:

1. A compound containing a diphenylmethane structure, wherein a structure of the compound is as shown in General Formula (1):

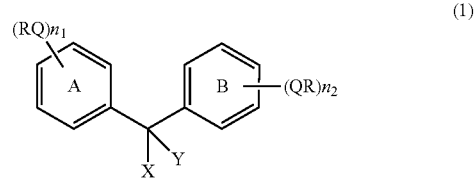

wherein,

X is selected from OH, halogen or NHR$_a$, and R$_a$ is selected from hydrogen, alkyl group or aralkyl group;

Y is selected from hydrogen, phenyl group or halogenated phenyl group;

ring A and ring B may contain a substituent selected from halogen atom, C$_1$-C$_5$ alkyl group substituted with halogen atom, C$_1$-C$_5$ alkyl group unsubstituted with halogen atom, C$_1$-C$_5$ alkoxy group substituted with halogen atom, or C$_1$-C$_5$ alkoxy group unsubstituted with halogen atom, in addition to the RQ substituent;

Q is independently selected from O, NH, NHCO, CO, CONH, S, SO or SO$_2$;

n$_1$ and n$_2$ represents an integer of 0-3, respectively, and n$_1$ and n$_2$ are not 0 at the same time;

R is independently selected from a group represented by General Formula (2):

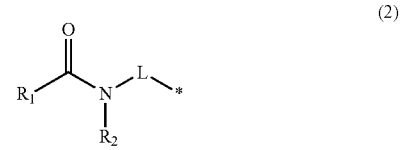

in the General Formula (2), * represents connected with Q;

$R_1$ is selected from a $C_1$-$C_{25}$ alkyl group or a group represented by General Formula (3):

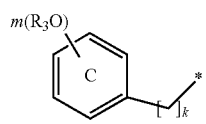
(3)

in the General Formula (3), * represents connected with carbonyl;

m represents an integer of 1-3;

$R_3$ is selected from $C_6$-$C_{25}$ alkyl group, and a total carbon number of m $R_3$ is not less than 8;

k represents an integer of 0-3;

ring C may contain a substituent selected from halogen atom, $C_1$-$C_5$ alkyl group substituted with halogen atom, $C_1$-$C_5$ alkyl group unsubstituted with halogen atom, $C_1$-$C_5$ alkoxy group substituted with halogen atom, $C_1$-$C_5$ alkoxy group unsubstituted with halogen atom, in addition to the m $R_3O$ substituents;

$R_2$ is selected from hydrogen, $C_1$-$C_{25}$ alkyl group or a group represented by General Formula (4):

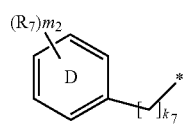
(4)

in the General Formula (4), * represents connected with N; $m_2$ represents an integer of 0-3;

$R_7$ is selected from $C_6$-$C_{25}$ alkyl group;

$k_7$ represents an integer of 1-6;

ring D may contain a substituent selected from halogen atom, $C_1$-$C_5$ alkyl group substituted with halogen atom, $C_1$-$C_5$ alkyl group unsubstituted with halogen atom, $C_1$-$C_5$ alkoxy group substituted with halogen atom, $C_1$-$C_{15}$ alkoxy group unsubstituted with halogen atom, in addition to the $m_2$ $R_7O$ substituents;

L is selected from $C_2$-$C_{15}$ organic chain group containing O, N or S heteroatoms, or $C_2$-$C_{15}$ organic chain group not containing O, N or S heteroatoms, and when L is selected from the $C_2$-$C_{15}$ organic chain group not containing O, N or S heteroatoms, $R_2 \neq H$.

2. The compound containing a diphenylmethane structure of claim 1, wherein X is selected from OH or $NHR_a$, and $R_a$ is selected from hydrogen, alkyl group or aralkyl group; Q is an oxygen atom.

3. The compound containing a diphenylmethane structure of claim 1, wherein R is independently selected from a group represented by General Formula (5):

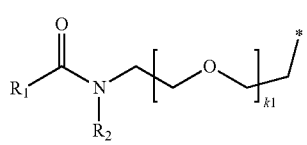
(5)

wherein,

* represents connected with Q;

k1 represents an integer of 0-3, and when k1=0, $R_2 \neq H$.

4. The compound containing a diphenylmethane structure of claim 1, wherein R is independently selected from a group represented by General Formula (6):

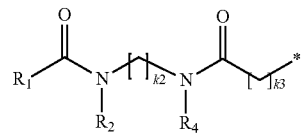
(6)

wherein,

* represents connected with Q;

$R_4$ is selected from hydrogen, $C_1$-$C_{25}$ alkyl group or the group represented by the General Formula (4) in claim 1;

k2 represents an integer of 1-4;

k3 represents an integer of 1-4.

5. The compound containing a diphenylmethane structure of claim 1, wherein R is independently selected from a group represented by General Formula (7):

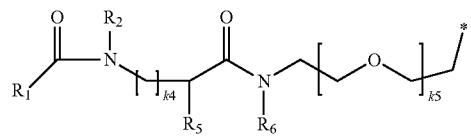
(7)

wherein,

* represents connected with Q;

$R_6$ is selected from hydrogen, $C_1$-$C_{25}$ alkyl group or the group represented by the General Formula (4) in claim 1;

k4 represents an integer of 0-3;

k5 represents an integer of 0-3;

$R_5$ is selected from hydrogen, a side chain group of a natural amino acid, an alkyl group or a group represented by General Formula (8):

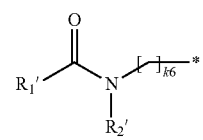
(8)

in the General Formula (8), k6 represents an integer of 1-4;

$R_{2'}$ is selected from hydrogen, $C_1$-$C_{25}$ alkyl group or the group represented by the General Formula (4) in claim 1;

$R_{1'}$ is selected from $C_1$-$C_{25}$ alkyl group or the group represented by the General Formula (3) in claim 1.

6. The compound containing a diphenylmethane structure of claim 1, wherein $R_1$ is selected from $C_1$-$C_{18}$ alkyl group or the group represented by the General Formula (3), and the total carbon number of m $R_3$ is 8-60.

7. The compound containing a diphenylmethane structure of claim 1, wherein $m_2$ is selected from 2 or 3, and the total carbon number of $m_2$ $R_7$ is 8-60.

8. The compound containing a diphenylmethane structure of claim 1, wherein $R_2$ is selected from hydrogen, methyl, ethyl, propyl, isopropyl, isooctyl, benzyl or 4-methoxybenzyl.

9. The compound containing a diphenylmethane structure of claim 1, wherein the compound has a structure selected from the following:

DPA-001
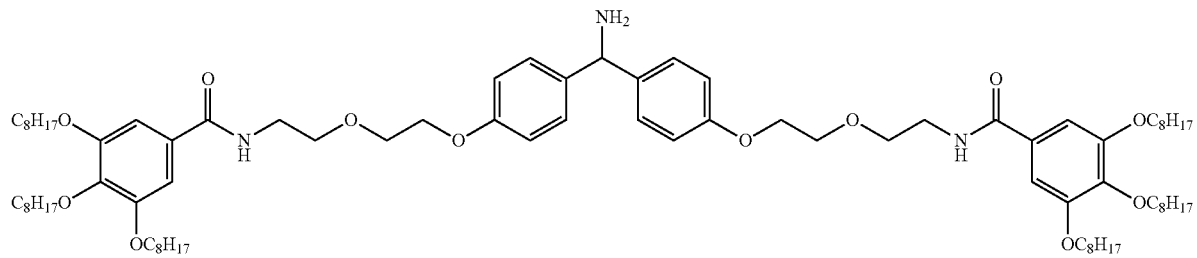

DPA-002
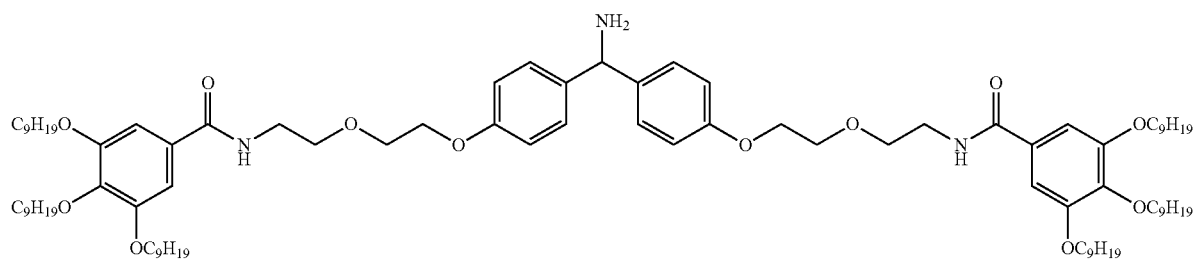

DPA-003
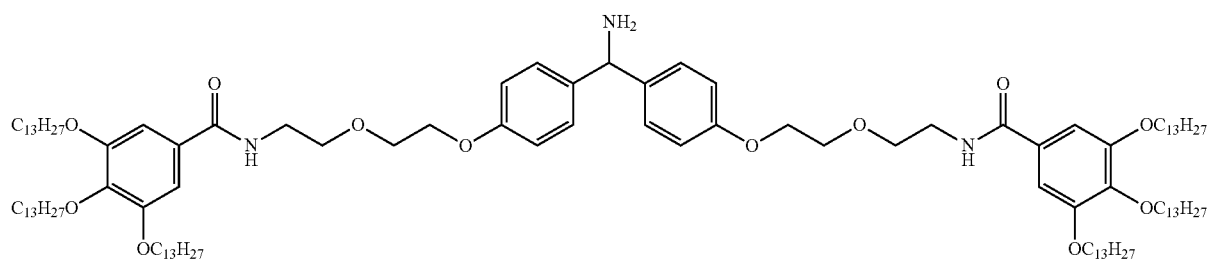

DPA-004
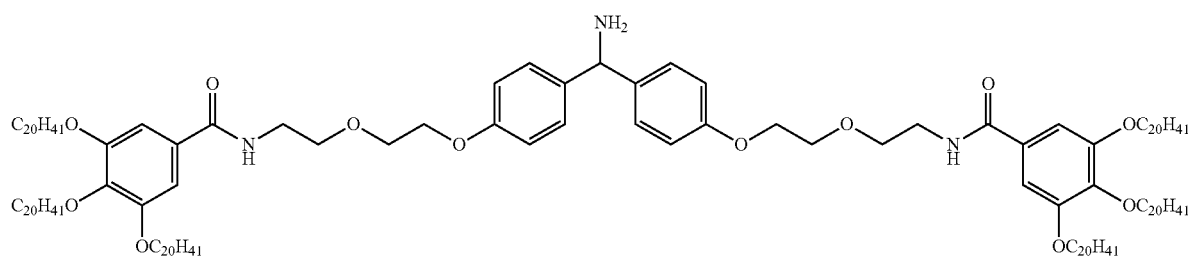

DPA-005
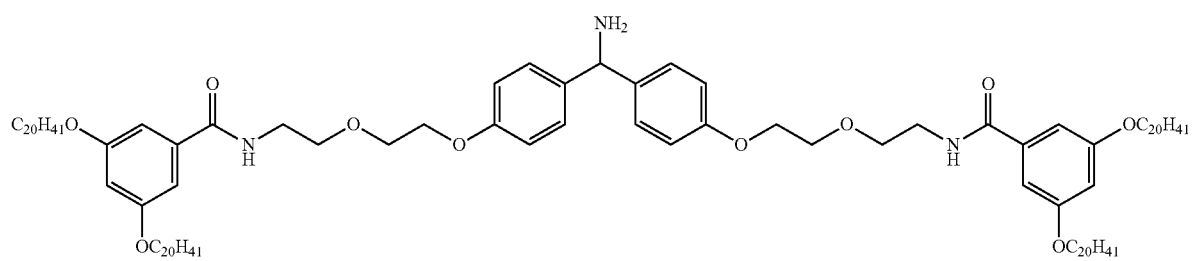

-continued
DPA-006
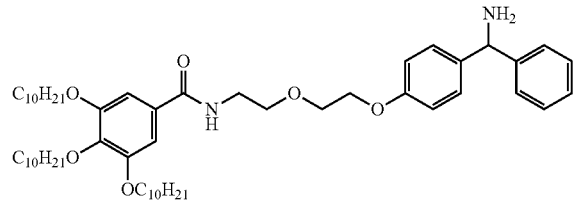
DPA-007
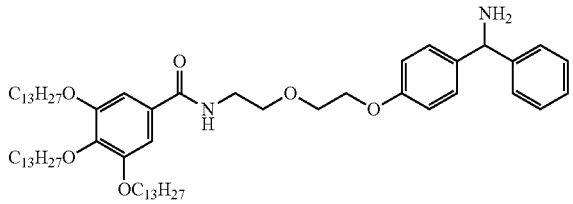
DPA-008
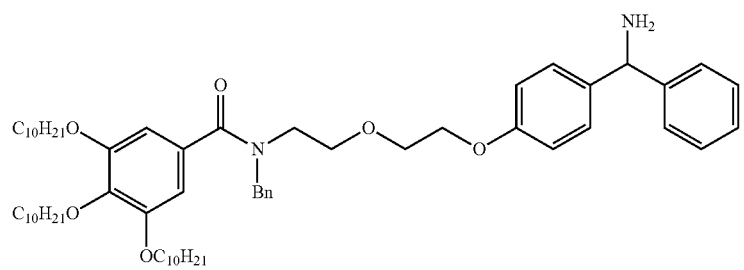
DPA-009
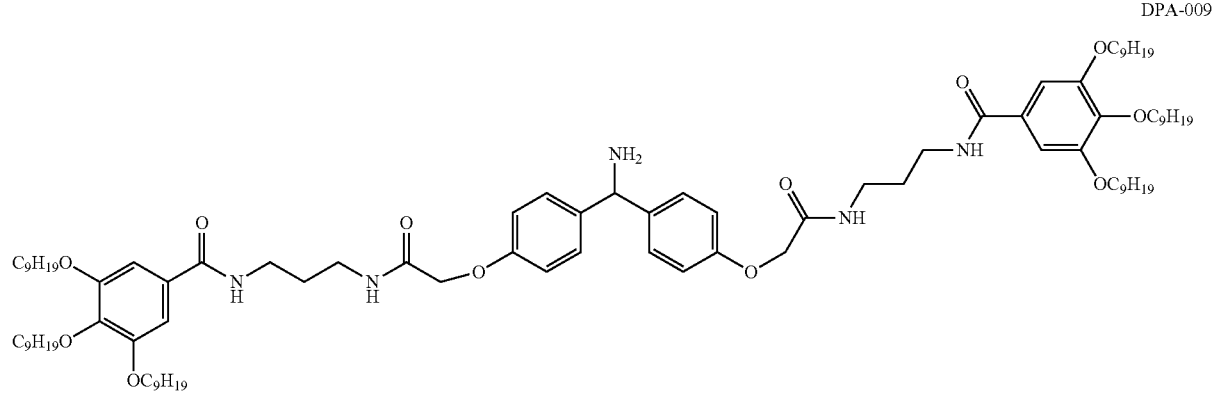
DPA-010
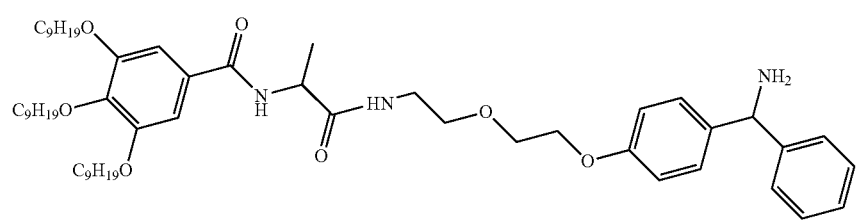
DPA-011
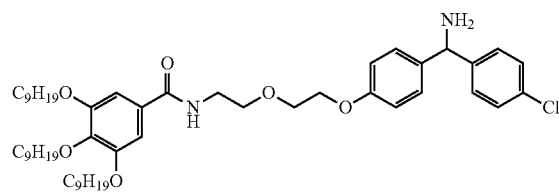
DPA-012
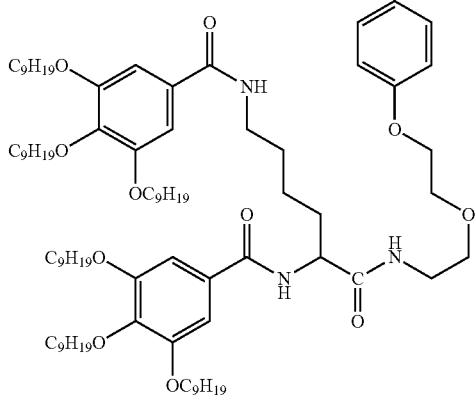

-continued
DPA-013
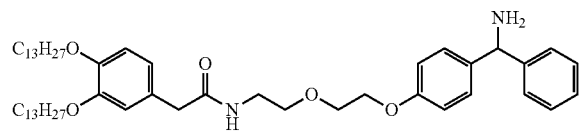
DPA-014
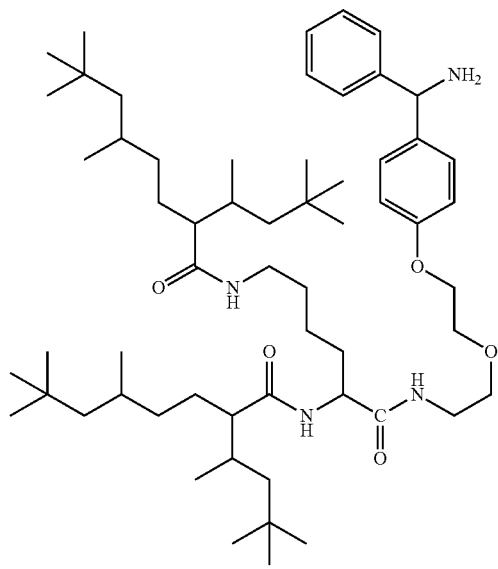
DPA-015
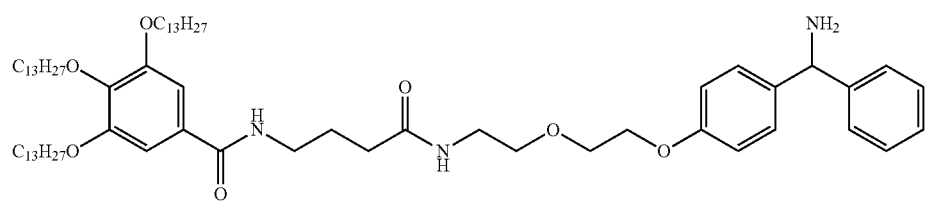
DPA-016
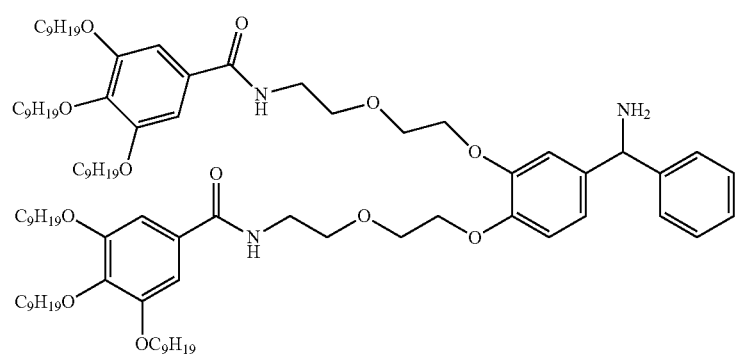
DPA-017
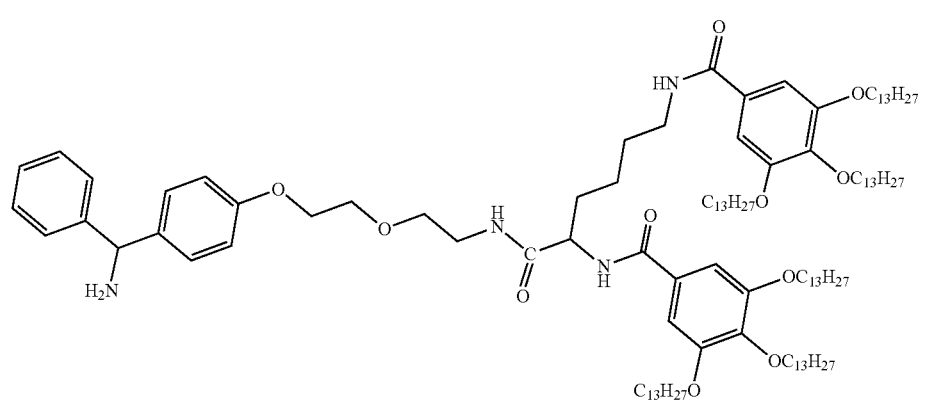

DPA-018
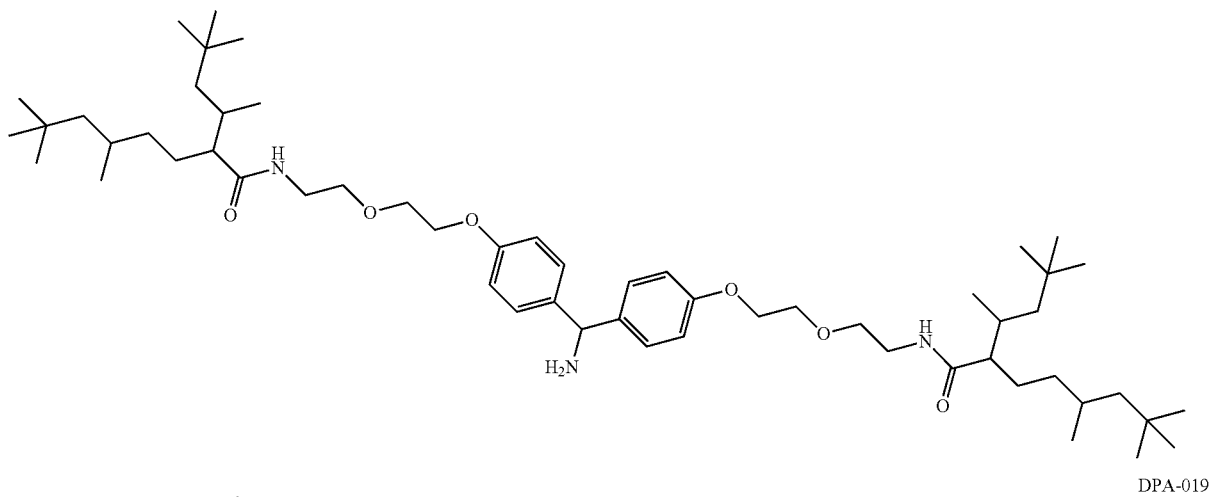
DPA-019
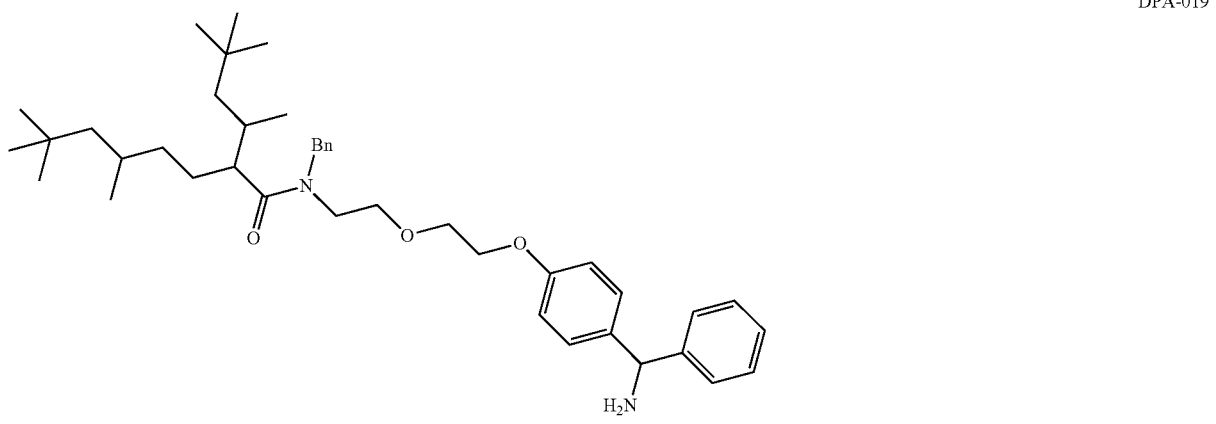
DPA-020
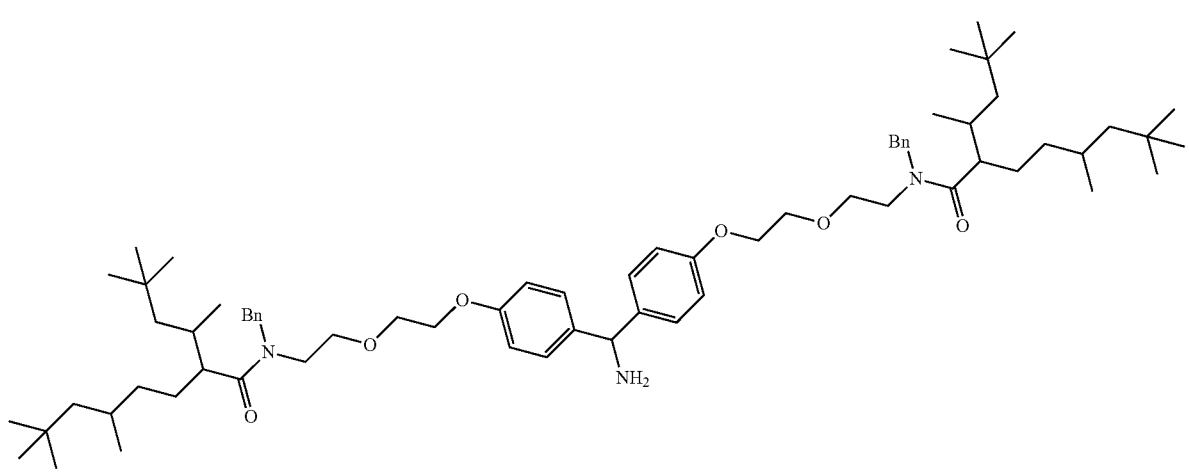
DPA-021
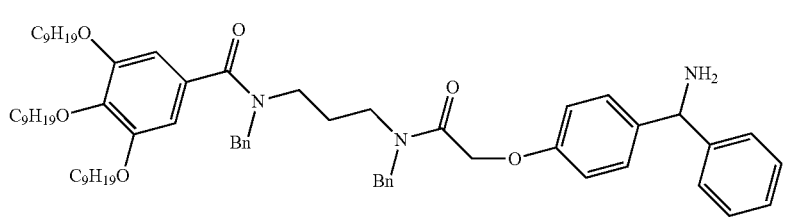

-continued
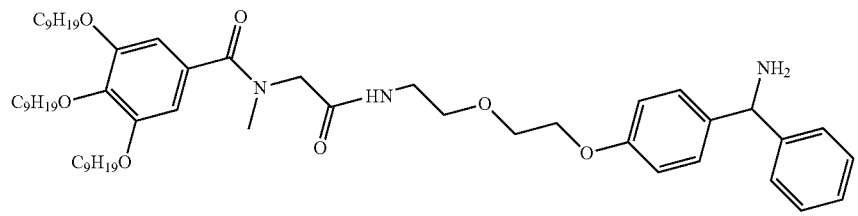
DPA-022
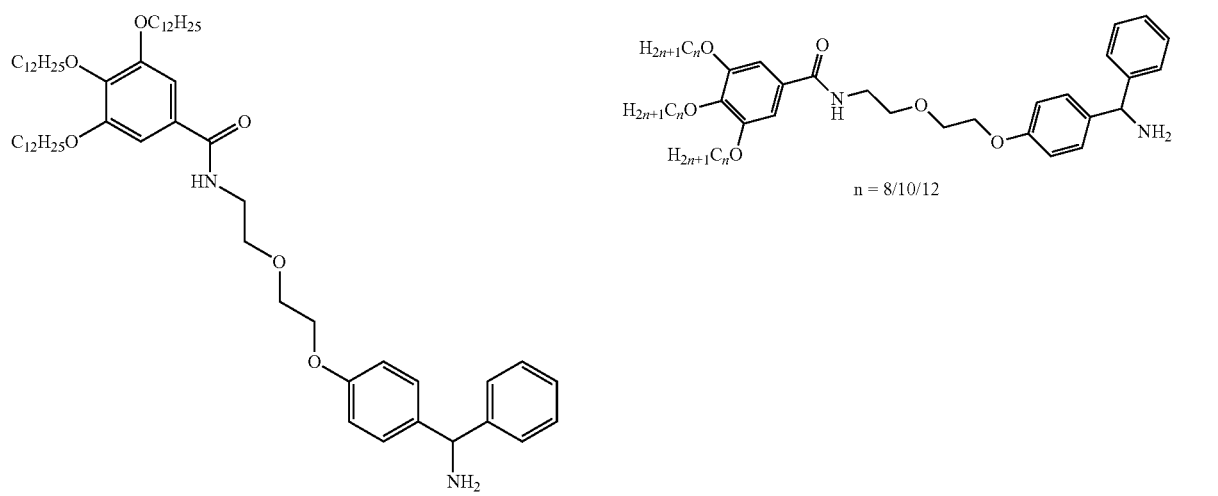
DPA-023
DPA-024
n = 8/10/12
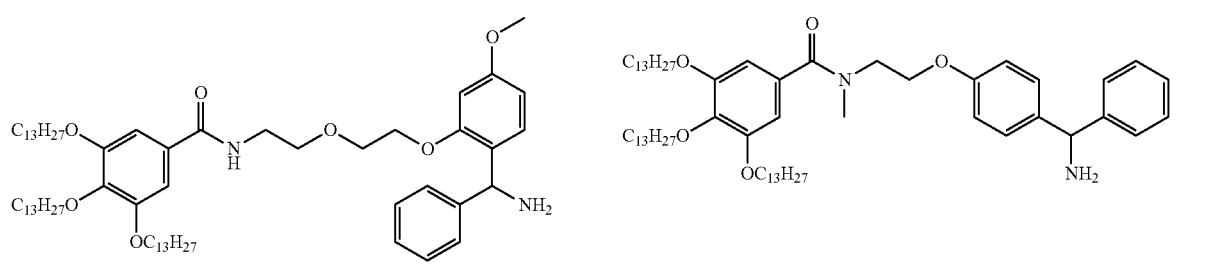
DPA-025
DPA-026
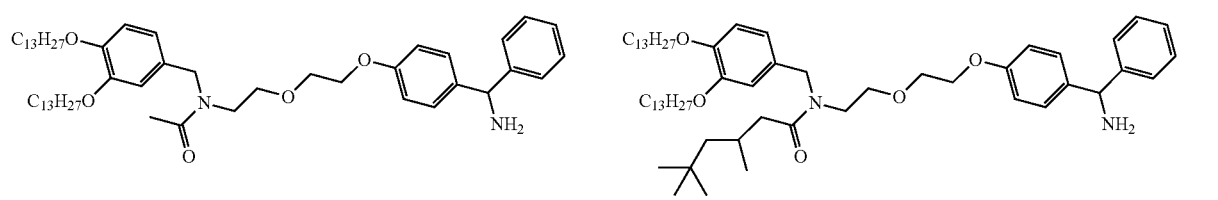
DPA-027
DPA-028
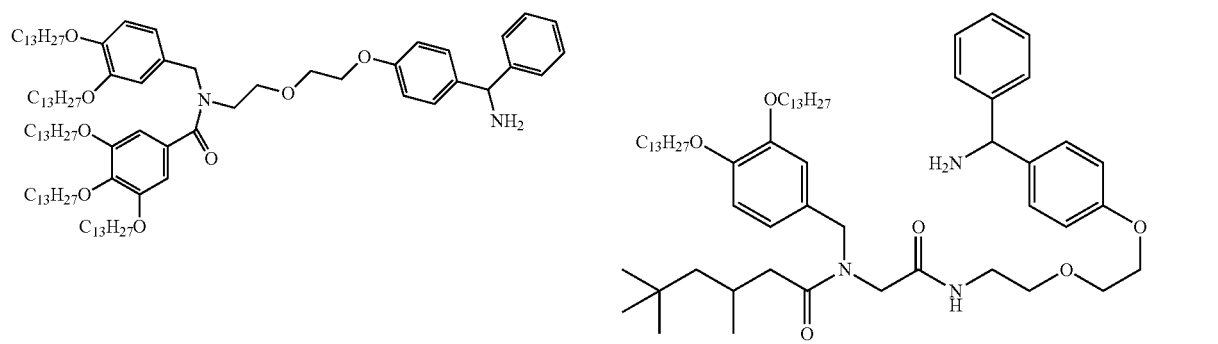
DPA-029
DPA-030

-continued

DPA-031

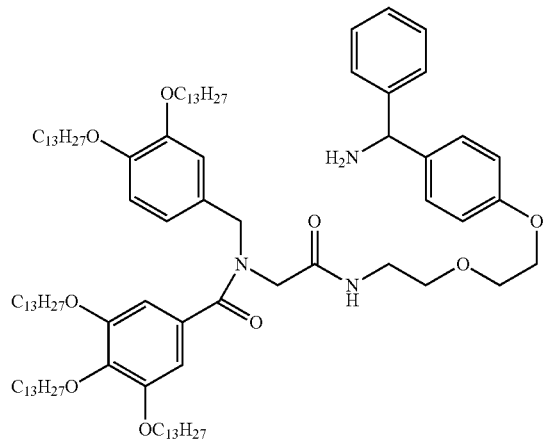

DPA-032

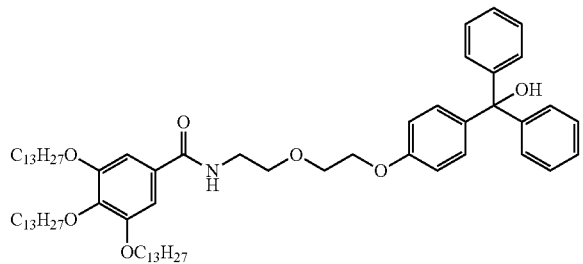

DPA-033

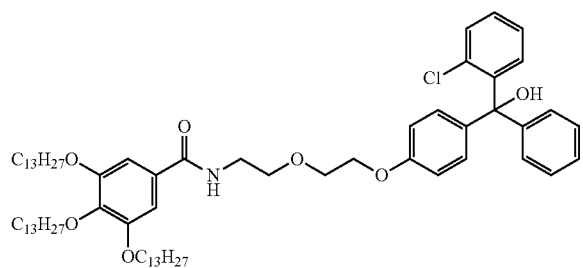

DPA-034

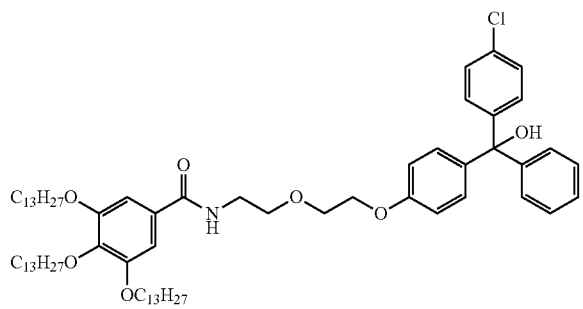

DPA-035

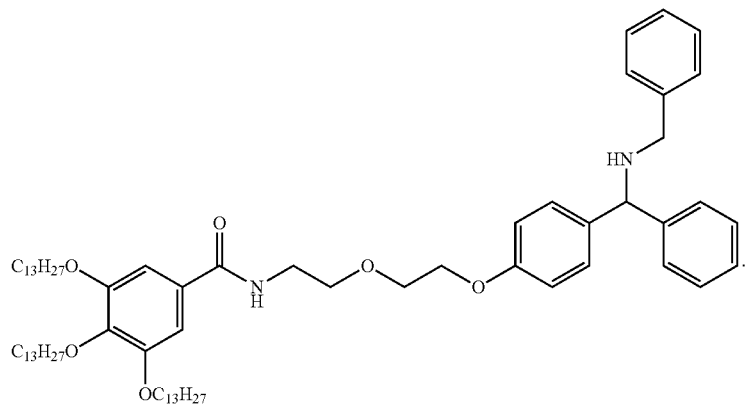

10. The compound containing a diphenylmethane structure of claim 1, wherein the compound containing a diphenylmethane structure is easily dissolved in at least one of hydrocarbon-based organic solvent, aromatic hydrocarbon-based organic solvent, ester-based organic solvent, ether-based organic solvent, and water-soluble aprotic-based polar organic solvent.

11. The compound containing a diphenylmethane structure of claim 10, wherein the solubility of the compound in N,N-dimethylformamide is greater than 1% at 25-30° C.

12. The compound containing a diphenylmethane structure of claim 6, wherein m is selected from 2 or 3.

13. The compound containing a diphenylmethane structure of claim 1, wherein $R_3$ is selected from $C_8$-$C_{22}$ alkyl group.

14. The compound containing a diphenylmethane structure of claim 1, wherein $R_7$ is selected from $C_8$-$C_{22}$ alkyl group.

15. The compound containing a diphenylmethane structure of claim 1, wherein the hydrocarbon-based organic solvent is selected from at least one of heptane, hexane, petroleum ether, cyclohexane, and methylcyclohexane.

16. The compound containing a diphenylmethane structure of claim 1, wherein the aromatic hydrocarbon-based organic solvent is selected from at least one of toluene, ethylbenzene, and xylene.

17. The compound containing a diphenylmethane structure of claim 1, wherein the ester-based organic solvent is selected from at least one of isopropyl acetate, tert-butyl acetate, and ethyl acetate.

18. The compound containing a diphenylmethane structure of claim 1, wherein the ether-based organic solvent is selected from at least one of ethyl ether, isopropyl ether, methyl tert-butyl ether, methyl cyclopentyl ether, and tetrahydrofuran.

19. The compound containing a diphenylmethane structure of claim 1, wherein the water-soluble aprotic-based polar organic solvent is selected from at least one of N,N-dimethylformamide, N,N-diethylformamide, N,N-dimethylacetamide, N-methyl-pyrrolidone, N-ethyl-pyrrolidone, dimethyl sulfoxide, sulfolane, 1,3-dimethylimidazolinone, 1,3-dimethyl-3,4,5,6-tetrahydro-2-pyrimidinone.

* * * * *